United States Patent [19]

McCall et al.

[11] Patent Number: 5,120,843

[45] Date of Patent: Jun. 9, 1992

[54] PHARMACEUTICALLY ACTIVE AMINES

[75] Inventors: John M. McCall; Donald E. Ayer, both of Kalamazoo; E. Jon Jacobsen, Plainwell; Frederick J. VanDoornik, Hamilton; John R. Palmer, Kalamazoo, all of Mich.

[73] Assignee: Upjohn, Kalamazoo, Mich.

[21] Appl. No.: 425,726

[22] Filed: Oct. 23, 1989

Related U.S. Application Data

[63] Continuation-in-part of Ser. No. 43,274, filed as PCT/US88/01212, Apr. 20, 1988, abandoned.

[51] Int. Cl.⁵ .............. C07D 211/10; C07D 241/04; C07D 239/26; C07D 213/24; C07D 251/24; C07D 253/065; C07D 207/20; C07D 223/04; C07D 239/34; C07D 241/12; C07D 233/20; C07D 249/02

[52] U.S. Cl. .................... 544/123; 546/227; 546/14; 546/22; 546/197; 546/210; 544/377; 544/370; 544/406; 544/372; 544/364; 544/365; 544/360; 544/357; 544/337; 544/229; 544/295; 544/69; 544/53; 544/54; 544/55; 544/57; 544/58.1; 544/58.4; 544/58.5; 544/58.6; 544/60; 544/62; 544/83; 544/96; 544/113; 544/82; 544/121; 544/205; 544/206; 544/207; 544/182; 544/208; 544/209; 544/211; 544/212; 544/194; 544/210; 544/213; 544/195; 544/214; 544/216; 544/217; 544/218; 544/219; 544/366; 544/376; 544/373; 544/368; 544/238; 544/232; 544/243; 544/316; 544/317; 544/318; 544/319; 544/320; 544/321; 544/324; 544/327; 544/328; 544/331; 544/333; 544/122; 544/405; 540/542; 540/604; 540/596; 540/608; 540/480; 540/481; 540/483; 540/450; 540/598; 536/23; 536/24; 536/31; 548/406; 548/413; 548/526; 548/535; 548/336; 548/112

[58] Field of Search .............. 540/542, 603, 596, 608, 540/480, 483, 481, 450; 536/23, 24; 548/406, 535, 413, 336; 546/14, 210, 22, 27; 544/377, 372, 360, 229, 53, 57, 58.5, 62, 113, 205, 182, 211, 210, 214, 218, 376, 238, 316, 319, 324, 331, 123, 370, 364, 357, 295, 54, 58.1, 586, 83, 82, 206, 208, 212, 213, 216, 219, 373, 232, 317, 320, 327, 333, 405, 406, 365, 337, 69, 55, 58.4, 60, 96, 121, 207, 209, 194, 195, 217, 366, 368, 243, 318, 321, 328, 122

[56] References Cited

U.S. PATENT DOCUMENTS

| | | | |
|---|---|---|---|
| 3,188,313 | 6/1965 | Archer | 260/268 |
| 3,472,855 | 10/1969 | Archer | 260/268 |
| 3,562,278 | 2/1971 | Archer | 260/268 |
| 3,947,474 | 3/1976 | Scott | 549/405 |
| 4,003,919 | 1/1977 | Scott | 549/405 |
| 4,018,799 | 4/1977 | Scott | 549/399 |
| 4,026,907 | 5/1977 | Scott | 549/407 |
| 4,153,612 | 5/1979 | McCall | 549/355 |
| 4,181,665 | 1/1980 | McCall | 549/331 |
| 4,302,589 | 11/1981 | Fanshawe | 546/201 |
| 4,681,890 | 7/1987 | Kanehira | 514/333 |
| 4,728,650 | 3/1988 | Eziri | 514/253 |

FOREIGN PATENT DOCUMENTS

| | | |
|---|---|---|
| 0202580 | 5/1986 | European Pat. Off. |
| 0199400 | 10/1986 | European Pat. Off. |
| 0244018 | 11/1987 | European Pat. Off. |
| 0345808 | 6/1989 | European Pat. Off. |
| 7124369 | 6/1967 | Japan |
| 61-254546 | 5/1985 | Japan |
| 947885 | 1/1964 | United Kingdom |
| 2127814 | 4/1984 | United Kingdom |
| WO87/01706 | 3/1987 | World Int. Prop. O. |

OTHER PUBLICATIONS

Chemical Abstracts–vol. 60,11991 (1964).

Primary Examiner—John M. Ford
Attorney, Agent, or Firm—Bruce Stein

[57] ABSTRACT

The aromatic amines (I), alkyl amines (II), bicyclic amines (III),

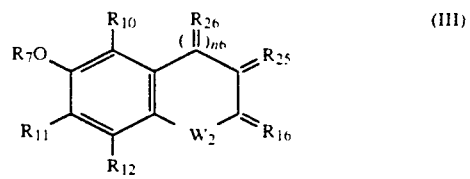

cycloalkyl amines (IV), aromatic bicyclic amines (V), hydroquinone amines (VI), quinone amines (VII), amino-ethers (VIII) and bicyclic amino ethers (IX) are useful as pharmaceutical agents for treating a number of conditions including spinal trauma, mild and/or moderate to severe head injury, etc. Also disclosed is a method of treatment using the 3,4-dihydrobenzopyrans (XI).

10 Claims, No Drawings

PHARMACEUTICALLY ACTIVE AMINES

CROSS-REFERENCE TO RELATED APPLICATIONS

The present patent application is a continuation-in-part patent application of PCT/U.S.88/01212, filed Apr. 20, 1988, which was a continuation-in-part patent application of U.S. patent application Ser. No. 043,274, filed Apr. 27, 1987 (now abandoned).

BACKGROUND OF THE INVENTION

1. Field of the Invention

Disclosed are aromatic, alkyl, bicyclic and cycloalkyl amines. These compounds are useful pharmaceutical agents in treating head injury, spinal cord trauma, stroke and a number of other related injuries and conditions.

2. Description of the Related Art

The non-amine portion of some of the aromatic amines (I) are known.

The non-amine portions of the alkyl amines (II) are known to those skilled in the art or can readily be prepared from known compounds by methods known to those skilled in the art.

The non-amine portions of the bicyclic amines (III) are known to those skilled in the art. See, in particular, U.S. Pat. Nos. 3,947,473, 4,003,919, 4,018,799, 4,026,907 and 4,681,890. See also British Patent 947,885 and Chem. Abst., 60, 11991 (1964). EP 202,580-A discloses 3,4-dihydrobenzopyran derivatives, similar to the non-amine portion of the bicyclic amines (III), which are attached to a 4-phenylmethyl-1-piperazinyl or a 4-(4-pyridinylmethyl)-1-piperazinyl group. While these compounds are similar to the bicyclic amines (III) of the present invention, the bicyclic amines (III) do not have a methylene group between the phenyl or 4-pyridinyl substituent and the piperazinyl group.

The non-amine portions of the cycloalkyl amines (IV) are known to those skilled in the art or can readily be prepared from known compounds by methods known to those skilled in the art.

The non-amine portions of the aromatic bicyclic amines (V) are known to those skilled in the art. See, in particular, U.S. Pat. Nos. 4,181,665 (isochromans—6 member heterocyclic ring) and 4,153,612 (2-benzoxepins—7 member heterocyclic ring). These patents also disclose the non-amine portion of the aromatic bicyclic amines (V), attached to various amines, but different amines than included within the present invention. Those amines were disclosed as possessing antihypertensive and tranquilization activity including antidepressant and antianxiety effects. The activity of the aromatic bicyclic amines (V) is quite different.

Published PCT patent application Ser. No. U.S. 86/01797, International Disclosure Number WO87/01706 (PCT 86/01797) discloses amino steroids where the amine portion includes acyclic, aromatic and heterocyclic amine functionality very similar to the amino substituents, where M is —NR$_A$R$_B$, of the present invention. In PCT 86/01797, the amino substituent was attached to the terminal carbon atom of the C$_{17}$ side chain of a steroid. The present invention differs from PCT 86/01797 in that the non-amine portion is not a steroid. PCT 86/01797 also disclosed numerous references involving various amines and amino substituents which are incorporated here by reference. PCT 86/01797 is the reference which discloses amino substituents most similar to those of the present invention.

The non-amine portion of the hydroquinones (VI) and quinones (VII) are well known to those skilled in the art. Great Britin patent 2,127,814A disloses aminoquinones containing a fused ring containing a nitrogen atom, the hydroquinones (VI) and quinones (VII) of the present patent do not contain a ring fused to the hydroquinone or quinone. J6 1,254,546A discolses acyclic amine quinone derivatives which contain only a simple nitrogen atom in a long side chain of carbon atoms. U.S. Patent discloses amino-quinones but of an indole type.

The non-amine portion of the amino ethers (VIII) are known to those skilled in the art. JA-7,124,369 discloses heptatrienes which are not similar to the bicyclic aromatic/7-member nitrogen-oxygen containing ring system of the amino ethers (VIII)

The non-amine portion of the bicyclic amino ethers (IX) are known to those skilled in the art. EP 244018-A discloses oxazoleamine derivatives but where the oxazole ring is not fused to a phenyl ring as in the present situation. EP 199400-A discloses a fused oxazole-phenyl ring system having a side chain containing nitrogen.

U.S. Pat. No. 4,728,650 (EP 202,580-A) discloses 3,4-dihydrobenzopyran derivatives which are similar to some of the bicyclic amines of formula (III). The activity (utility) of the compounds disclosed in U.S. Pat. No. 4,728,650 is anti-peptic ulcer, antitussive and/or expectorant. The utility claimed for these agents in the present patent application has nothing to do with gastritis caused by inflammation of the gastric mucosa.

Published PCT patent application Ser. No. JP87/00106, International Disclosure Number WO87/05020 (PCT 87/00106) discloses 3,4-dihydrobenzopyrans linked to nitrogen containing heterocyclic groups including 1-piperazinyl substituted in the 4-position with with a variety of nitrogen groups including 4-pyridinylcarbonyl (4-nicotinoyl), and 3-pyridinylmethyl which are similar to some of the bicyclic amines of formula (III).

SUMMARY OF INVENTION

Disclosed are aromatic amines of formula (I) where:
(I) R$_1$ or R$_2$ and R$_3$ taken together are —O—CH$_2$—O— and the other of R$_1$ or R$_2$ is —H;
R$_{22}$ is —H, —Cl or C$_1$-C$_3$ alkyl;
R$_{23}$ is —H, —Cl or C$_1$-C$_3$ alkyl;
(II) R$_1$ and R$_2$ are the same or different and are —H, C$_1$-C$_4$ alkyl, —F, —Cl and —Br, and R$_3$ is —H, —OH, C$_1$-C$_3$ alkoxy, —O—SO$_2$—CH$_3$, —O—CO—(C$_1$-C$_4$ alkyl) and —O—prodrug where prodrug is

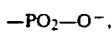—PO$_2$—O$^-$,

—CO—CH$_2$—CO—NH—CH$_2$—SO$_2$—O$^-$,

—CO—(CH$_2$)$_{n21}$—R$_{51}$ where n$_{21}$ is 1-7 and R$_{51}$ is —COO$^-$, —NR$_{51-1}$R$_{51-2}$ where R$_{51-1}$ and R$_{51-2}$ are the same or different and are —H or C$_1$-C$_3$ alkyl, —N$^+$R$_{51-1}$R$_{51-2}$R$_{51-3}$halide$^-$ where R$_{51-1}$R$_{51-2}$R$_{51-3}$ are the same or different and are —H or C$_1$-C$_3$ alkyl, and where halide is —Cl or —Br,

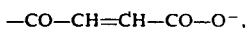—CO—CH=CH—CO—O$^-$,

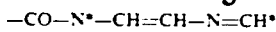

where the atoms marked with an asterisk (*) are bonded to each other resulting in the formation of a ring,

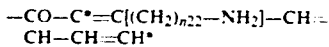

where $n_{22}$ is 1 or 2 and where the atoms marked with an asterisk (*) are bonded to each other resulting in the formation of a ring,

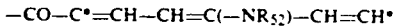

where $R_{52}$ is —H or $C_1$-$C_3$ alkyl and where the atoms marked with an asterisk (*) are bonded to each other resulting in the formation of a ring, —CO—(CH$_2$)$_{n21}$—CO—O—[C$_6$H$_{12}$O$_6$ sugars],

—CO—O—CH(CH$_2$—O—CO—R$_{53}$)$_2$ where the $R_{53}$'s are the same or different and are $C_1$-$C_{18}$,

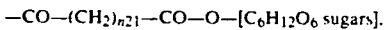
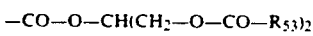

where cation$^-$ is sodium, potassium or trialkylammonium where alkyl is $C_1$-$C_3$, —CH$_2$—O—CO—(CH$_2$)$_{n21}$—NR$_{51-1}$R$_{51-2}$ where $n_{21}$, $R_{51-1}$ and $R_{51-2}$ are as defined above,

—CO—NH—C$_6$H$_4$—R$_{55}$ where $R_{55}$ is —H or $C_1$-$C_3$ alkyl, —NO$_2$, —NR$_{51-1}$R$_{51-2}$ where $R_{51-1}$ and $R_{51-2}$ are as defined above and $R_{22}$ is —H, —OH, —Cl, $C_1$-$C_3$ alkyl, —OCH$_3$ or —OC$_2$H$_5$;

$R_{23}$ is —H, —OH, —Cl, $C_1$-$C_3$ alkyl, —OCH$_3$ or —OC$_2$H$_5$; with the proviso that only two of $R_3$, $R_{22}$ and $R_{23}$ can have a variable substituent containing an oxygen atom attached to the benzene ring; where $X_1$ is —O—,

—CH$_2$—,

—C(CH$_3$)(CH$_3$)—,

—C(H)(R$_{24}$)— where $R_{24}$ is $C_1$-$C_3$ alkyl or phenyl optionally substituted with 1 or 2 —OH, —CH$_3$ or —OCH$_3$,

—C(OH)(R$_{13}$)

where $R_{13}$ is —H or $C_1$-$C_3$ alkyl, or phenyl optionally substituted with 1 or 2 —OH, —CH$_3$ or —OCH$_3$,

—S—,

—Si—,

—CO—,

—NH—CO— and

—NR$_4$— where $R_4$ is —H or $C_1$-$C_4$ alkyl;
$n_1$ is 0-10;
$R_8$ and $R_9$ are the same or different and are —H or $C_1$-$C_3$ alkyl;
$n_{13}$ is 0 or 1;
$n_{14}$ is 2-5;
M is
(I) —NR$_A$R$_B$ where:
(A) R$_A$ is
(1) —(CH$_2$)$_m$—NR$_{M-1}$-heteroaryl, where m is 2, 3 or 4, where R$_{M-1}$ is —H or $C_1$-$C_3$ alkyl, where heteroaryl is:
(a) pyridin-2-(F-1), 3-(F-2) or 4-yl (F-3) or the N-oxide thereof optionally substituted by 1 or 2 R$_{M-2}$, being the same or different, where R$_{M-2}$ is
(i) —F,
(ii) —Cl,
(iii) —Br,
(iv) $C_1$-$C_5$ alkyl,
(v) —CH$_2$—CH=CH$_2$,
(vi) -aryl, where aryl is phenyl optionally substituted with 1 through 2 —F, —Cl, —Br, $C_1$-$C_3$ alkoxy, —COOH, —NH$_2$, $C_1$-$C_3$ alkylamino, di($C_1$-$C_3$)alkylamino, where the alkyl groups are the same or different, 1-pyrrolidinyl-, 1-piperidinyl-, 1-hexamethylenimino-, 1-heptamethylenimino-, $C_2$-$C_4$ acylamino and —NH—CHO or with 1 —F or —CF$_3$;
(vii) —NR$_{M-3}$R$_{M-3}$ where the R$_{M-3}$s are the same or different and are —H, $C_1$-$C_3$ alkyl or —CH$_2$—CH=CH$_2$,
(viiiα) *CH$_2$—(CH$_2$)$_q$—CH$_2$—N*— where the atoms marked with an asterisk (*) are bonded to each other resulting in the formation of a ring, where q is 1 through 5,
(viiiβ) *CH$_2$—(CH$_2$)$_c$—G—(CH$_2$)$_d$—CH$_2$—N*— where the atoms marked with an asterisk (*) are bonded to each other resulting in the formation of a ring (F-4), where G is —O—, —S—, —SO—, —SO$_2$— or —NR$_{M-4}$—, where R$_{M-4}$ is —H, $C_1$-$C_3$ alkyl, or aryl as defined above, where c and d are the same or different and are 0 through 2 with the proviso that the total number of ring carbon atoms is 4, 5 or 6,
(ix) 3-pyrrolin-1-yl, (F-5)
(x) pyrrol-1-yl optionally substituted with $C_1$-$C_3$ alkyl, (F-6)
(xi) piperidin-1-yl optionally substituted with 1 or 2 $C_1$-$C_3$ alkyl, (F-7)
(xii) 1,2,3,6-tetrahydropyridin-1-yl, (F-8)
(xiii) 1-hexamethyleneimino containing a 3- or 4-double bond or 3- and 5-double bonds, (F-9)
(xiv) 1,4-dihydro-1-pyridinyl substituted in the 4 position by two $C_1$-$C_3$ alkyl being the same or different, (F-10)
(xv) —OH,
(xvi) $C_1$-$C_3$ alkoxy,
(xvii) —NR$_{M-7}$—(CH$_2$)$_e$—Q where Q is 2-pyridinyl where R$_{M-7}$ is —H or $C_1$-$C_3$ alkyl and e is 0 through 3,
(xviii) pyridin-2-, 3- or 4-yl,
(xix) —CF$_3$, (xx) —CCl₃,
(xxi) —SCH₃, (b) 1,3,5-triazin-2-yl or the N-oxide thereof optionally substituted at the 4- and/or 6-position with $R_{M\text{-}2}$ is as defined above, (F-11)

(c) pyrimidin-4-yl or the N-oxide thereof optionally substituted at the 2- and/or 6-, and 5- and/or 6-position with $R_{M\text{-}2}$ is as defined above, (F-12)

(d) pyrimidin-2-yl optionally substituted at 4- and/or 6-position with 1 or 2 $R_{M\text{-}2}$ as is defined above, (F-13)

(e) pyrazin-2-yl optionally substituted with 1 or 2 $R_{M\text{-}2}$ as is defined above, (F-14)

(f) imidazol-2-yl optionally substituted in the 1 position with $C_1$-$C_3$ alkyl or -aryl, where aryl is as defined above, and further optionally substituted with 1 or 2 $R_{M\text{-}2}$ as defined above, (F-15)

(g) 1,3,4-triazol-2-yl optionally substituted in the 1 position with $C_1$-$C_3$ alkyl or -aryl, where aryl is as defined above, and further optionally substituted with $R_{M\text{-}2}$ as defined above, (F-16)

(h) imidazol-4- or 5-yl optionally substituted in the 1 position with $C_1$-$C_3$ alkyl or -aryl, where aryl is as defined above, and further optionally substituted with 1 or 2 $R_{M\text{-}2}$ as defined above, (F-17)

(i) benzo[b]thien-2-yl, (F-18)

(j) indol-2-yl, (F-19)

(k) benzo[b]thiazol-2-yl, (F-20)

(l) benzimidazol-2-yl, (F-21)

(m) 4-[2-[4-[2,6-bis(1-pyrrolidinyl)-4-pyrimidinyl]-1-piperazinyl]ethyl], (F-22)

(n) 1,2,4-triazin-3-yl optionally substituted at the 5- and/or 6-position with $R_{M\text{-}2}$ as is defined above, (F-23)

(2) —$(CH_2)_2$-4-(1-piperazinyl) optionally substituted in the 4-position with -aryl or -heteroaryl as defined above, (F-24)

(3) -heteroaryl, as defined above, (4) —$(CH_2)_m$—$X_4$ where m is as defined above and where $X_4$ is (a) —O—$CH_2CH_2$—Y, where Y is $C_1$-$C_3$ alkyl-amino, di($C_1$-$C_3$)alkylamino where the alkyl groups are the same or different, $C_3$-$C_6$ alkyleneimino, optionally substituted with 1 or 2 $C_1$-$C_3$ alkyl, (b) —$NR_{M\text{-}5}CH_2CH_2$—Y, where $R_{M\text{-}5}$ is —H or $C_1$-$C_3$ alkyl and Y is as defined above, (c) —$(CH_2)_g$—$N(R_{M\text{-}5})$-heteroaryl, where g is 2, 3 or 4, and where $R_{M\text{-}5}$ and heteroaryl are as defined above, (5) —$(CH_2)_m$—$NR_{M\text{-}6}R_{M\text{-}8}$, where $R_{M\text{-}6}$ is —H or $C_1$-$C_3$ alkyl and $R_{M\text{-}8}$ is -aryl or -heteroaryl as defined above, or $R_{M\text{-}6}$ and $R_{M\text{-}8}$ are taken together with the attached nitrogen atom to form a saturated mono-nitrogen $C_3$-$C_6$ heterocyclic ring and where m is as defined above, (6) —$(CHCH_3)_b$—$(CH_2)_f$-aryl where b is 0 and f is 1 through 4 or b is 1 and f is 0 through 3, where aryl is as defined above, (7) —$(CH_2)_i$-heteroaryl, where i is 1 through 4 and heteroaryl is as defined above, (8) (1-piperazinyl)acetyl substituted in the 4-position by heteroaryl where heteroaryl is as defined above, (F-25)

(9) (1-piperazinyl)carbonylmethyl substituted in the 4-position by -heteroaryl where heteroaryl is as defined above, and (F-26)

(B) $R_B$ is (1) —H, (2) $C_1$-$C_3$ alkyl, (3) $C_5$-$C_7$ cycloalkyl, (4) —$(CH_2)_m$—$NR_{M\text{-}1}$-heteroaryl, where m, $R_{M\text{-}1}$ and heteroaryl are as defined above, (5) (1-piperazinyl)-($C_2$-$C_4$)alkyl optionally substituted in the 4-position with -aryl or -heteroaryl as defined above, (F-24)

(6) —$(CH_2)_m$—$X_4$, where m and $X_4$ are as defined above, (7) —$(CH_2)_m$—$NR_{M\text{-}6}R_{M\text{-}8}$, where m, $R_{M\text{-}6}$ and $R_{M\text{-}8}$ are as defined above, (8) —$(CHCH_3)_b$—$(CH_2)_f$—$R_{M\text{-}9}$, where b, f and $R_{M\text{-}9}$ are as defined above, (9) 2-pyridinylmethyl, (C) $R_A$ and $R_B$ are taken together with the attached nitrogen atom to form a heterocyclic ring selected from the group consisting of (1) 2-(carboxy)-1-pyrrolidinyl optionally as the $C_1$-$C_3$ alkyl ester or as a pharmaceutically acceptable salt, (F-27)

(2) 2-(carboxy)-1-piperidinyl optionally as the $C_1$-$C_3$ alkyl ester or as a pharmaceutically acceptable salt, (F-28)

(3) 2-(carboxy)-1-hexamethyleneimino optionally as the $C_1$-$C_3$ alkyl ester or as a pharmaceutically acceptable salt, (F-29)

(4) 2-(carboxy)-1-heptamethyleneimino optionally as the $C_1$-$C_3$ alkyl ester or as a pharmaceutically acceptable salt, (F-30)

(5) 1-piperazinyl optionally substituted in the 4-position with $R_{M\text{-}12}$—CO—$(CH_2)_j$— where $R_{M\text{-}12}$ is -aryl, -heteroaryl, —$NR_{M\text{-}13}$-heteroaryl and 2-furanyl, where $R_{M\text{-}13}$ is —H or $C_1$-$C_3$ alkyl, where j is 0 through 3, and aryl and heteroaryl are as defined above, (F-31)

(6) 1-piperazinyl substituted in the 4-position with heteroaryl—$(CH_2)_j$—, where heteroaryl and j are as defined above, (F-32)

(7) 1-piperazinyl substituted in the 4-position with aryl-$(CH_2)_j$—, where aryl and j are as defined above, (F-33)

(8) 4-hydroxy-1-piperidinyl substituted in the 4-position with aryl as defined above, (F-34)

(9) 1-piperazinyl substituted in the 4-position with heteroaryl—$NR_{M\text{-}13}$—CO—$(CH_2)_i$—, where heteroaryl, $R_{M\text{-}13}$ and i are as defined above; (F-35)

(10) 1-piperazinyl substituted in the 4-position with —$(CH_2)_j$—$C^*$=C(2-pyridinyl)—N=N—C(2-pyridinyl)=$C^*$H, where * and j are as defined above, (F-36)

(11) 1-piperazinyl substituted in the 4-position with —$(CH_2)_i$-[4-[2,6-bis(1-pyrrolidinyl)-4-pyrimidinyl]-1-piperazine] (F-37) or (II) —$C^*$=C(2-pyridinyl)—N=N—C(2-pyridinyl)=$C^*$H where * is as defined above and pharmaceutically acceptable salts thereof, and hydrates and solvates thereof.

Preferred are compounds where $X_1$ is —O—, —$CH_2$— or $X_1$ is —CO—; where $n_1$ is 0–6 more preferrably $n_1$ is 1–6; where $R_1$ and $R_2$ are the same and are —H, $C_1$ alkyl or $C_4$ alkyl; where $R_3$ is —OH or $C_1$-$C_3$ alkoxy; where $R_8$ and $R_9$ are both —H; where $n_{13}$ is 0 and the compounds of EXAMPLES 24-52, 56-59, 65, 69, 70, 72-74, 77 and 182.

Also disclosed are alkyl amines of the formula $X_2$—$(CH_2)_{n2}$—M (II) where:

$n_2$ is 4-14;

$X_2$ is —H, —OH, —O—CO—($C_1$-$C_4$ alkyl), —O—CO—H, —O—CO—O—($C_1$-$C_4$ alkyl), ($C_1$-$C_4$) alkoxycarbonyl, —O—CO—aryl where aryl is $\phi$ optionally substituted with

—OH,

—OCH$_3$,

—F,

—Cl,

—Br,

—CF$_3$,

—$C_1$-$C_3$ alkyl, and

—CO—R$_5$ where R$_5$ is

—OH,

—NH$_2$,

—NHR$_6$ where
R$_6$ is $\phi$ or $C_1$-$C_3$ alkyl, and —N(R$_{14}$)(R$_{15}$) where R$_{14}$ and R$_{15}$ are the same or different and are $C_1$-$C_3$ alkyl; M is (I) —NR$_A$R$_B$ where:
  (A) R$_A$ is
    (1) —(CH$_2$)$_m$—NR$_{M-1}$-heteroaryl, where m is 2, 3 or 4, where R$_{M-1}$ is —H or $C_1$-$C_3$ alkyl, where heteroaryl is:
      (a) pyridin-2- (F-1), 3- (F-2) or 4-yl (F-3) or the N-oxide thereof optionally substituted by 1 or 2 R$_{M-2}$, being the same or different, where R$_{M-2}$ is
        (i) —F,
        (ii) —Cl,
        (iii) —Br,
        (iv) $C_1$-$C_5$ alkyl,
        (v) —CH$_2$—CH=CH$_2$,
        (vi) -aryl, where aryl is phenyl optionally substituted with 1 through 2 —F, —Cl, —Br, $C_1$-$C_3$ alkoxy, —COOH, —NH$_2$, $C_1$-$C_3$ alkylamino, di($C_1$-$C_3$)alkylamino, where the alkyl groups are the same or different, 1-pyrrolidinyl-, 1-piperidinyl, 1-hexamethylenimino-, 1-heptamethylenimino-, $C_2$-$C_4$ acylamino and —NH—CHO or with 1 —F or —CF$_3$;
        (vii) —NR$_{M-3}$R$_{M-3}$ where the R$_{M-3}$s are the same or different and are —H, $C_1$-$C_3$ alkyl or —CH$_2$—CH=CH$_2$,
        (viiiα) *CH$_2$—(CH$_2$)$_q$—CH$_2$—N*— where the atoms marked with an asterisk (*) are bonded to each other resulting in the formation of a ring, where q is 1 through 5,
        (viiiβ) *CH$_2$—(CH$_2$)$_c$—G—(CH$_2$)$_d$—CH$_2$—N*—where the atoms marked with an asterisk (*) are bonded to each other resulting in the formation of a ring (F-4), where G is —O—, —S—, —SO—, —SO$_2$— or —NR$_{M-4}$—, where R$_{M-4}$ is —H, $C_1$-$C_3$ alkyl, or aryl as defined above, where c and d are the same or different and are 0 through 2 with the proviso that the total number of ring carbon atoms is 4, 5 or 6,
        (ix) 3-pyrrolin-1-yl,
        (x) pyrrol-1-yl optionally substituted with $C_1$-$C_3$ alkyl, (F-6)
        (xi) piperidin-1-yl optionally substituted with 1 or 2 $C_1$-$C_3$ alkyl, (F-7)
        (xii) 1,2,3,6-tetrahydropyridin-1-yl, (F-8)
        (xiii) 1-hexamethyleneimino containing a 3- or 4-double bond or 3- and 5-double bonds, (F-9)
        (xiv) 1,4-dihydro-1-pyridinyl substituted in the 4 position by two $C_1$-$C_3$ alkyl being the same or different, (F-10)
        (xv) —OH,
        (xvi) $C_1$-$C_3$ alkoxy,
        (xvii) —NR$_{M-7}$—(CH$_2$)$_e$—Q where Q is 2-pyridinyl where R$_{M-7}$ is —H or $C_1$-$C_3$ alkyl and e is 0 through 3,
        (xviii) pyridin-3- or 4-yl,
        (xix) —CF$_3$,
        (xx) —CCl$_3$,
        (xxi) —SCH$_3$,
      (b) 1,3,5-triazin-2-yl or the N-oxide thereof optionally substituted at the 4- and/or 6-position with R$_{M-2}$ is as defined above, (F-11)
      (c) pyrimidin-4-yl or the N-oxide thereof optionally substituted at the 2- and/or 6-, and 5- and/or 6-position with R$_{M-2}$ is as defined above, (F-12)
      (d) pyrimidin-2-yl optionally substituted at 4- and/or 6-position with 1 or 2 R$_{M-2}$ as is defined above, (F-13)
      (e) pyrazin-2-yl optionally substituted with 1 or 2 R$_{M-2}$ as is defined above, (F-14)
      (f) imidazol-2-yl optionally substituted in the 1 position with $C_1$-$C_3$ alkyl or -aryl, where aryl is as defined above, and further optionally substituted with 1 or 2 R$_{M-2}$ as defined above, (F-15)
      (g) 1,3,4-triazol-2-yl optionally substituted in the 1 position with $C_1$-$C_3$ alkyl or -aryl, where aryl is as defined above, and further optionally substituted with R$_{M-2}$ as defined above, (F-16)
      (h) imidazol-4- or 5-yl optionally substituted in the 1 position with $C_1$-$C_3$ alkyl or -aryl, where aryl is as defined above, and further optionally substituted with 1 or 2 R$_{M-2}$ as defined above, (F-17)
      (i) benzo[b]thien-2-yl, (F-18)
      (j) indol-2-yl, (F-19)
      (k) benzo[b]thiazol-2-yl, (F-20)
      (l) benzimidazol-2-yl, (F-21)
      (m) 4-[2-[4-[2,6-bis(1-pyrrolidinyl)-4-pyrimidinyl]-1-piperazinyl]ethyl], (F-22)

(n) 1,2,4-triazin-3-yl optionally substituted at the 5- and/or 6-position with $R_{M-2}$ as is defined above, (F-23)

(2) —$(CH_2)_{2-4}$—(1-piperazinyl) optionally substituted in the 4-position with -aryl or -heteroaryl as defined above, (F-24)

(3) -heteroaryl, as defined above, (4) —$(CH_2)_m$—$X_4$ where m is as defined above and where $X_4$ is (a) —O—$CH_2CH_2$—Y, where Y is $C_1$-$C_3$ alkylamino, di($C_1$-$C_3$)alkylamino where the alkyl groups are the same or different, $C_3$-$C_6$ alkyleneimino, optionally substituted with 1 or 2 $C_1$-$C_3$ alkyl, (b) —$NR_{M-5}CH_2CH_2$—Y, where $R_{M-5}$ is —H or $C_1$-$C_3$ alkyl and Y is as defined above, (c) —$(CH_2)_g$—$N(R_{M-5})$-heteroaryl, where g is 2, 3 or 4, and where $R_{M-5}$ and heteroaryl are as defined above, (5) —$(CH_2)_m$—$NR_{M-6}R_{M-8}$, where $R_{M-6}$ is —H or $C_1$-$C_3$ alkyl and $R_{M-8}$ is -aryl or -heteroaryl as defined above, or $R_{M-6}$ and $R_{M-8}$ are taken together with the attached nitrogen atom to form a saturated mono-nitrogen $C_3$-$C_6$ heterocyclic ring and where m is as defined above, (6) —$(CHCH_3)_b$—$(CH_2)_f$—aryl where b is 0 and f is 1 through 4 or b is 1 and f is 0 through 3, where aryl is as defined above, (7) —$(CH_2)_i$—heteroaryl, where i is 1 through 4 and heteroaryl is as defined above, (8) (1-piperazinyl)acetyl substituted in the 4-position by heteroaryl where heteroaryl is as defined above, (F-25)

(9) (1-piperazinyl)carbonylmethyl substituted in the 4-position by -heteroaryl where heteroaryl is as defined above, and (F-26)

(B) $R_B$ is (1) —H, (2) $C_1$-$C_3$ alkyl, (3) $C_5$-$C_7$ cycloalkyl, (4) —$(CH_2)_m$—$NR_{M-1}$-heteroaryl, where m, $R_{M-1}$ and heteroaryl are as defined above, (5) (1-piperazinyl)-$(C_2$-$C_4$)alkyl optionally substituted in the 4- position with -aryl or -heteroaryl as defined above, (F-24)

(6) —$(CH_2)_m$—$X_4$, where m and $X_4$ are as defined above, (7) —$(CH_2)_m$—$NR_{M-6}R_{M-8}$, where m, $R_{M-6}$ and $R_{M-8}$ are defined above, (8) —$(CHCH_3)_b$—$(CH_2)_f$—$R_{M-9}$, where b, f and $R_{M-9}$ are as defined above, (9) 2-pyridinylmethyl, (C) $R_A$ and $R_B$ are taken together with the attached nitrogen atom to form a heterocyclic ring selected from the group consisting of (1) 2-(carboxy)-1-pyrrolidinyl optionally as the $C_1$-$C_3$ alkyl ester or as a pharmaceutically acceptable salt, (F-27)

(2) 2-(carboxy)-1-piperidinyl optionally as the $C_1$-$C_3$ alkyl ester or as a pharmaceutically acceptable salt, (F-28)

(3) 2-(carboxy)-1-hexamethyleneimino optionally as the $C_1$-$C_3$ alkyl ester or as a pharmaceutically acceptable salt, (F-29)

(4) 2-(carboxy)-1-heptamethyleneimino optionally as the $C_1$-$C_3$ alkyl ester or as a pharmaceutically acceptable salt, (F-30)

(5) 1-piperazinyl optionally substituted in the 4-position with $R_{M-12}$—CO—$(CH_2)_j$— where $R_{M-12}$ is -aryl, -heteroaryl, —$NR_{M-13}$-heteroaryl and 2-furanyl, where $R_{M-13}$ is —H or $C_1$-$C_3$ alkyl, where j is 0 through 3, and aryl and heteroaryl are as defined above, (F-31)

(6) 1-piperazinyl substituted in the 4-position with heteroaryl—$(CH_2)_j$—, where heteroaryl and j are as defined above, (F-32)

(7) 1-piperazinyl substituted in the 4-position with aryl—$(CH_2)_j$—, where aryl and j are as defined above, (F-33)

(8) 4-hydroxy-1-piperidinyl substituted in the 4-position with aryl as defined above, (F-34)

(9) 1-piperazinyl substituted in the 4-position with heteroaryl—$NR_{M-13}$—CO—$(CH_2)_i$—, where heteroaryl, $R_{M-13}$ and i are as defined above; (F-35)

(10) 1-piperazinyl substituted in the 4-position with —$(CH_2)_j$—$C^*$=C(2-pyridinyl)—N=N—C(2-pyridinyl)=$C^*H$, where * and j are as defined above, (F-36)

(11) 1-piperazinyl substituted in the 4-position with —$(CH_2)_i$—[4-[2,6-bis(1-pyrrolidinyl)-4-pyrimidinyl]-1-piperazine](F-37) or (II) —$C^*$=C(2-pyridinyl)—N=N—C(2-pyridinyl)=$C^*H$ where * is as defined above, and pharmaceutically acceptable salts thereof, and hydrates and solvates thereof.

Preferred are compounds where $n_2$ is 4-8, more preferrably where $n_2$ is 6 and where $X_2$ is —H, —OH, —O—CO—($C_1$-$C_4$ alkyl) or —O—CO—aryl and the compounds of EXAMPLES 1-17.

Further disclosed are bicyclic amines of formula (III) where:

$W_2$ is —O—, —S—, —$NR_{54}$— where $R_{54}$ is —H or $C_1$-$C_3$ alkyl, $n_6$ is 0, 1 or 2, $R_7$ is —H or —$C_1$-$C_4$ alkyl, —CO—($C_1$-$C_4$ alkyl), —CO—φ or -prodrug where prodrug is

—$PO_2$—$O^-$,

—CO—$CH_2$—CO—NH—$CH_2$—$SO_2$—$O^-$,

—CO—$(CH_2)_{n21}$—$R_{51}$ where $n_{21}$ is 1-7 and $R_{51}$ is —$COO^-$, —$NR_{51-1}R_{51-2}$ where $R_{51-1}$ and $R_{51-2}$ are the same or different and are —H or $C_1$-$C_3$ alkyl, —$N^+R_{51-1}R_{51-2}R_{51-3}$halide$^-$ where $R_{51-1}R_{51-2}R_{51-3}$ are the same or different and are —H or $C_1$-$C_3$ alkyl, and where halide is —Cl or —Br,

—CO—CH=CH—CO—$O^-$,

—CO—$N^*$—CH=CH—N=$CH^*$ where the atoms marked with an asterisk (*) are bonded to each other resulting in the formation of a ring,

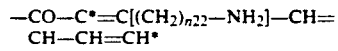

where $n_{22}$ is 1 or 2 and where the atoms marked with an asterisk (*) are bonded to each other resulting in the formation of a ring,

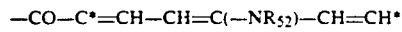

where $R_{52}$ is —H or $C_1$-$C_3$ alkyl and where the atoms marked with an asterisk (*) are bonded to each other resulting in the formation of a ring.

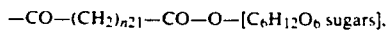

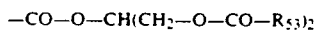

where the $R_{53}$'s are the same or different and are $C_1$-$C_{18}$.

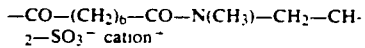

where cation⁺ is sodium, potassium or trialkylammonium where alkyl is $C_1$-$C_3$,

where $n_{21}$, $R_{51-1}$ and $R_{51-2}$ are as defined above,

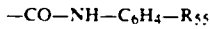

where $R_{55}$ is —H or $C_1$-$C_3$ alkyl. —$NO_2$, —$NR_{51-1}R_{51-2}$ where $R_{51-1}$ and $R_{51-2}$ are as defined above and $R_{10}$ is —H or —$CH_3$.
$R_{11}$ is —H or —$CH_3$.
$R_{12}$ is —H or —$CH_3$.
(18-1) $R_{16}$ is α-$R_{16-1}$:β-$R_{16-2}$ where one of $R_{16-1}$ and $R_{16-2}$ is —H, —$CH_3$, —$CH_2CH_3$ or —φ and the other is —$X_3$—M where $X_3$ is —CO—, —$(CH_2)_{n-16}$—CO— where $n_{16}$ is 1 or 2, —$(CH_2)_{n3}$— where $n_3$ is 1-6, or —CO—O—$(CH_2)_{n15}$— where $n_{15}$ is 2-6, $R_{25}$ and $R_{26}$ are —H:—H and where M is (I) —$NR_AR_B$ where:

(A) $R_A$ is (1) —$(CH_2)_m$—$NR_{M-1}$-heteroaryl, where m is 2, 3 or 4, where $R_{M-1}$ is —H or $C_1$-$C_3$ alkyl, where heteroaryl is:

(a) pyridin-2- (F-1), 3- (F-2) or 4-yl (F-3) or the N-oxide thereof optionally substituted by 1 or 2 $R_{M-2}$, being the same or different, where $R_{M-2}$ is
 (i) —F,
 (ii) —Cl,
 (iii) —Br,
 (iv) $C_1$-$C_5$ alkyl,
 (v) —$CH_2$—CH=$CH_2$,
 (vi) -aryl, where aryl is phenyl optionally substituted with 1 through 2 —F, —Cl, —Br, $C_1$-$C_3$ alkoxy, —COOH, —$NH_2$, $C_1$-$C_3$ alkylamino, di($C_1$-$C_3$)alkylamino, where the alkyl groups are the same or different, 1-pyrrolidinyl-, 1-piperidinyl, 1-hexamethylenimino-, 1-heptamethylenimino-, $C_2$-$C_4$ acylamino, —NH—CHO, with 1 —F or —$CF_3$ or with 3,4-methylenedioxy and 3,4-ethylenedioxy;
 (vii) —$NR_{M-3}R_{M-3}$ where the $R_{M-3}$s are the same or different and are —H, $C_1$-$C_3$ alkyl or —$CH_2$—CH=$CH_2$,
 (viiiα) *$CH_2$—$(CH_2)_q$—$CH_2$—N*— where the atoms marked with an asterisk (*) are bonded to each other resulting in the formation of a ring, where q is 1 through 5,
 (viiiβ) *$CH_2$—$(CH_2)_c$—G—$(CH_2)_d$—$CH_2$—N*— where the atoms marked with an asterisk (*) are bonded to each other resulting in the formation of a ring (F-4), where G is —O—, —S—, —SO—, —$SO_2$— or —$NR_{M-4}$—, where $R_{M-4}$ is —H, $C_1$-$C_3$ alkyl, or aryl as defined above, where c and d are the same or different and are 0 through 2 with the proviso that the total number of ring carbon atoms is 4, 5 or 6,
 (ix) 3-pyrrolin-1-yl, (F-5)
 (x) pyrrol-1-yl optionally substituted with $C_1$-$C_3$ alkyl, (F-6)
 (xi) piperidin-1-yl optionally substituted with 1 or 2 $C_1$-$C_3$ alkyl, (F-7)
 (xii) 1,2,3,6-tetrahydropyridin-1-yl, (F-8)
 (xiii) 1-hexamethyleneimino containing a 3- or 4-double bond or 3- and 5-double bonds, (F-9)
 (xiv) 1,4-dihydro-1-pyridinyl substituted in the 4 position by two $C_1$-$C_3$ alkyl being the same or different, (F-10)
 (xv) —OH,
 (xvi) $C_1$-$C_3$ alkoxy,
 (xvii) —$NR_{M-7}$—$(CH_2)_e$-Q where Q is 2-pyridinyl where $R_{M-7}$ is —H or $C_1$-$C_3$ alkyl and e is 0 through 3,
 (xviii) pyridin-2-, 3- or 4-yl,
 (xix) —$CF_3$,
 (xx) —$CCl_3$,
 (xxi) —$SCH_3$, (b) 1,3,5-triazin-2-yl or the N-oxide thereof optionally substituted at the 4- and/or 6-position with $R_{M-2}$ is as defined above, (F-11)

(c) pyrimidin-4-yl or the N-oxide thereof optionally substituted at the 2- and/or 6-, and 5- and/or 6-position with $R_{M-2}$ is as defined above, (F-12)

(d) pyrimidin-2-yl optionally substituted at 4- and/or 6-position with 1 or 2 $R_{M-2}$ as is defined above, (F-13)

(e) pyrazin-2-yl optionally substituted with 1 or 2 $R_{M-2}$ as is defined above, (F-14)

(f) imidazol-2-yl optionally substituted in the 1 position with $C_1$-$C_3$ alkyl or -aryl, where aryl is as defined above, and further optionally substituted with 1 or 2 $R_{M-2}$ as defined above, (F-15)

(g) 1,3,4-triazol-2-yl optionally substituted in the 1 position with $C_1$-$C_3$ alkyl or -aryl, where aryl is as defined above, and further optionally substituted with $R_{M-2}$ as defined above, (F-16)

(h) imidazol-4- or 5-yl optionally substituted in the 1 position with $C_1$-$C_3$ alkyl or -aryl, where aryl is as defined above, and further optionally substituted with 1 or 2 $R_{M-2}$ as defined above, (F-17)

(i) benzo[b]thien-2-yl, (F-18)

(j) indol-2-yl, (F-19)

(k) benzo[b]thiazol-2-yl, (F-20)

(l) benzimidazol-2-yl, (F-21)

(m) 4-[2-[4-[2,6-bis(1-pyrrolidinyl)-4-pyrimidinyl]-1-piperazinyl]ethyl], (F-22)

(n) 1,2,4-triazin-3-yl optionally substituted at the 5- and/or 6-position with $R_{M-2}$ as is defined above, (F-23)

(2) —$(CH_2)_{2-4}$—(1-piperazinyl) optionally substituted in the 4-position with -aryl or -heteroaryl as defined above, (F-24)

(3) -heteroaryl, as defined above, (4) —$(CH_2)_m$—$X_4$ where m is as defined above and where $X_4$ is
  (a) —O—$CH_2CH_2$—Y, where Y is $C_1$-$C_3$ alkylamino, di($C_1$-$C_3$)alkylamino where the alkyl groups are the same or different, $C_3$-$C_6$ alkyleneimino, optionally substituted with 1 or 2 $C_1$-$C_3$ alkyl,
  (b) —$NR_{M-5}CH_2CH_2$—Y, where $R_{M-5}$ is —H or $C_1$-$C_3$ alkyl and Y is as defined above,
  (c) —$(CH_2)_g$—$N(R_{M-5})$-heteroaryl, where g is 2, 3 or 4, and where $R_{M-5}$ and heteroaryl are as defined above,
(5) —$(CH_2)_m$—$NR_{M-6}R_{M-8}$, where $R_{M-6}$ is —H or $C_1$-$C_3$ alkyl and $R_{M-8}$ is -aryl or -heteroaryl as defined above, or $R_{M-6}$ and $R_{M-8}$ are taken together with the attached nitrogen atom to form a saturated mono-nitrogen $C_3$-$C_6$ heterocyclic ring and where m is as defined above,
(6) —$(CHCH_3)_b$—$(CH_2)_f$-aryl where b is 0 and f is 1 through 4 or b is 1 and f is 0 through 3, where aryl is as defined above,
(7) —$(CH_2)_i$-heteroaryl, where i is 1 through 4 and heteroaryl is as defined above,
(8) (1-piperazinyl)acetyl substituted in the 4-position by heteroaryl where heteroaryl is as defined above, (F-25)
(9) (1-piperazinyl)carbonylmethyl substituted in the 4-position by -heteroaryl where heteroaryl is as defined above, and (F-26) and
(B) $R_B$ is
 (1) —H,
 (2) $C_1$-$C_3$ alkyl,
 (3) $C_5$-$C_7$ cycloalkyl,
 (4) —$(CH_2)_m$—$NR_{M-1}$-heteroaryl, where m, $R_{M-1}$ and heteroaryl are as defined above,
 (5) (1-piperazinyl)-($C_2$-$C_4$)alkyl optionally substituted in the 4-position with -aryl or -heteroaryl as defined above, (F-24)
 (6) —$(CH_2)_m$—$X_4$, where m and $X_4$ are as defined above,
 (7) —$(CH_2)_m$—$NR_{M-6}R_{M-8}$, where m, $R_{M-6}$ and $R_{M-8}$ are as defined above,
 (8) —$(CHCH_3)_b$—$(CH_2)_f$—$R_{M-9}$, where b, f and $R_{M-9}$ are as defined above,
 (9) 2-pyridinylmethyl,
 (10) 2-phenylethyl,
(C) $R_A$ and $R_B$ are taken together with the attached nitrogen atom to form a heterocyclic ring selected from the group consisting of
 (1) 2-(carboxy)-1-pyrrolidinyl optionally as the $C_1$-$C_3$ alkyl ester or as a pharmaceutically acceptable salt, (F-27)
 (2) 2-(carboxy)-1-piperidinyl optionally as the $C_1$-$C_3$ alkyl ester or as a pharmaceutically acceptable salt, (F-28)
 (3) 2-(carboxy)-1-hexamethyleneimino optionally as the $C_1$-$C_3$ alkyl ester or as a pharmaceutically acceptable salt, (F-29)
 (4) 2-(carboxy)-1-heptamethyleneimino optionally as the $C_1$-$C_3$ alkyl ester or as a pharmaceutically acceptable salt, (F-30)
 (5) 1-piperazinyl optionally substituted in the 4-position with $R_{M-12}$—CO—$(CH_2)_j$— where $R_{M-12}$ is -aryl, -heteroaryl, —$NR_{M-13}$— heteroaryl and 2-furanyl, where $R_{M-13}$ is —H or $C_1$-$C_3$ alkyl, where j is 0 through 3, and aryl and heteroaryl are as defined above, (F-31)
 (6) 1-piperazinyl substituted in the 4-position with heteroaryl$(CH_2)_j$— where heteroaryl and j are as defined above, (F-32)
 (7) 1-piperazinyl substituted in the 4-position with aryl—$(CH_2)_j$—, where aryl and j are as defined above, (F-33)
 (8) 4-hydroxy-1-piperidinyl substituted in the 4-position with aryl as defined above, (F-34)
 (9) 1-piperazinyl substituted in the 4-position with heteroaryl—$NR_{M-13}$—CO-$(CH_2)_i$—, where heteroaryl, $R_{M-13}$ and i are as defined above; (F-35)
 (10) 1-piperazinyl substituted in the 4-position with —$(CH_2)_j$—$C^*$=C(2-pyridinyl)—N=N—C(2-pyridinyl)=$C^*$H, where * and j are as defined above, (F-36)
 (11) 1-piperazinyl substituted in the 4-position with —$(CH_2)_i$—[4-[2,6-bis(1-pyrrolidinyl)-4-pyrimidinyl]-1-piperazine] (F-37)
 (12) 1-piperazinyl substituted in the 4-position with $C_1$-$C_3$ alkyl optionally substituted with 1 or 2 aryl, or
(II)   —$C^*$=C(2-pyridinyl)—N=N—C(2-pyridinyl)=$C^*$H where * is as defined above
(18-2) $n_6$ is 0, $R_{16}$ is $R_{16-3}$:$R_{16-4}$ where one of $R_{16-3}$ and $R_{16-4}$ is taken together with $R_{25}$ to form a second bond between the carbon atoms to which $R_{16}$ and $R_{25}$ are attached and the other of $R_{16-3}$ and $R_{16-4}$ is —$X_3$—M where $X_3$ and M are as defined above,
(18-3) $n_6$ is 1, $R_{25}$ and $R_{26}$ are taken together to form a second bond between the carbon atoms to which $R_{25}$ and $R_{26}$ are attached and pharmaceutically acceptable salts thereof, and hydrates and solvates thereof.

A preferred embodiment of the bicyclic amines of formula (III) is where:

$W_2$ is —O—, —S—, —$NR_{54}$— where $R_{54}$ is —H or $C_1$-$C_3$ alkyl,
$n_6$ is 0, 1 or 2,
$R_7$ is —H, —CO—($C_1$-$C_4$ alkyl), —CO—φ or -prodrug where prodrug is —$PO_2$—$O^-$, —CO—$CH_2$—CO—NH—$CH_2$—$SO_2$—$O^-$,
—CO—$(CH_2)_{n21}$-$R_{51}$ where $n_{21}$ is 1-7 and $R_{51}$ is —COO$^-$, —$NR_{51-1}R_{51-2}$ where $R_{51-1}$ and $R_{51-2}$ are the same or different and are —H or $C_1$-$C_3$ alkyl, —$N^+R_{51-1}R_{51-2}R_{51-3}$halide$^-$ where $R_{51-1}R_{51-2}R_{51-3}$ are the same or different and are —H or $C_1$-$C_3$ alkyl, and where halide is —Cl or —Br,

—CO—CH=CH—CO—$O^-$,

—CO—$N^*$—CH=CH—N=$CH^*$ where the atoms marked with an asterisk (*) are bonded to each other resulting in the formation of a ring, —CO—$C^*$=C[$(CH_2)_{n22}$—$NH_2$]—CH=CH—CH=$CH^*$ where $n_{22}$ is 1 or 2 and where the atoms marked with an asterisk (*) are bonded to each other resulting in the formation of a ring,

—CO—$C^*$=CH—CH=C(—$NR_{52}$)—CH=$CH^*$ where $R_{52}$ is —H or $C_1$-$C_3$ alkyl and where the atoms marked with an asterisk (*) are bonded to each other resulting in the formation of a ring, —CO—(CH$_2$)$_{n21}$—CO—O—[C$_6$H$_{12}$O$_6$ sugars],

—CO—O—CH(CH$_2$—O—CO—R$_{53}$)$_2$ where the R$_{53}$'s are the same or different and are C$_1$-C$_{18}$, —CO—(CH$_2$)$_6$—CO—N(CH$_3$)—CH$_2$—CH$_2$—SO$_3^-$ cation$^+$ where cation$^+$ is sodium, potassium or trialkylammonium where alkyl is C$_1$-C$_3$, —CH$_2$—O—CO—(CH$_2$)$_{n21}$—NR$_{51-1}$R$_{51-2}$ where n$_{21}$, R$_{51-1}$ and R$_{51-2}$ are as defined above,

—CO—NH—C$_6$H$_4$—R$_{55}$ where R$_{55}$ is —H or C$_1$-C$_3$ alkyl, —NO$_2$, —NR$_{51-1}$R$_{51-2}$ where R$_{51-1}$ and R$_{51-2}$ are as defined above, and R$_{10}$ is —H or —CH$_3$,
R$_{11}$ is —H or —CH$_3$,
R$_{12}$ is —H or —CH$_3$, (18-1) R$_{16}$ is α-R$_{16-1}$:β-R$_{16-2}$ where one of R$_{16-1}$ and R$_{16-2}$ is —H, —CH$_3$, —CH$_2$CH$_3$ or —φ and the other is —X$_3$—M where X$_3$ is —CO—, —(CH$_2$)$_{n16}$—CO— where n$_{16}$ is 1 or 2, —(CH$_2$)$_{n3}$— where n$_3$ is 1-6, or —CO—O—(CH$_2$)$_{n15}$— where n$_{15}$ is 2-6, R$_{25}$ and R$_{26}$ are —H:—H and where M is (I) —NR$_A$R$_B$ where:

(A) R$_A$ is (1) —(CH$_2$)$_m$—NR$_{M-1}$—heteroaryl, where m is 2, 3 or 4, where R$_{M-1}$ is —H or C$_1$-C$_3$ alkyl, where heteroaryl is:

(a) pyridin-2- (F-1), 3- (F-2) or 4-yl (F-3) or the N-oxide thereof optionally substituted by 1 or 2 R$_{M-2}$, being the same or different, where R$_{M-2}$ is
  (i) —F,
  (ii) —Cl,
  (iii) —Br,
  (iv) C$_1$-C$_5$ alkyl,
  (v) —CH$_2$—CH=CH$_2$,
  (vi) -aryl, where aryl is phenyl optionally substituted with 1 through 2 —F, —Cl, —Br, C$_1$-C$_3$ alkoxy, —COOH, —NH$_2$, C$_1$-C$_3$ alkylamino, di(C$_1$-C$_3$)alkylamino, where the alkyl groups are the same or different, 1-pyrrolidinyl-, 1-piperidinyl, 1-hexamethylenimino-, 1-heptamethylenimino-, C$_2$-C$_4$ acylamino, —NH—CHO, with 1—F or —F$_3$ or with 3,4-methylenedioxy and 3,4-ethylenedioxy;
  (vii) —NR$_{M-3}$R$_{M-3}$ where the R$_{M-3}$s are the same or different and are —H, C$_1$-C$_3$ alkyl or —CH$_2$—CH=CH$_2$,
  (viiiα) *CH$_2$—(CH$_2$)$_q$—CH$_2$—N*— where the atoms marked with an asterisk (*) are bonded to each other resulting in the formation of a ring, where q is 1 through 5,
  (viiiβ) *CH$_2$—(CH$_2$)$_c$—G—(CH$_2$)$_d$—CH$_2$—N*—where the atoms marked with an asterisk (*) are bonded to each other resulting in the formation of a ring (F-4), where G is —O—, —S—, —SO—, —SO$_2$— or —NR$_{M-4}$—, where R$_{M-4}$ is —H, C$_1$-C$_3$ alkyl, or aryl as defined above, where c and d are the same or different and are 0 through 2 with the proviso that the total number of ring carbon atoms is 4, 5 or 6,
  (ix) 3-pyrrolin-1-yl, (F-5)
  (x) pyrrol-1-yl optionally substituted with C$_1$-C$_3$ alkyl, (F-6)
  (xi) piperidin-1-yl optionally substituted with 1 or 2 C$_1$-C$_3$ alkyl, (F-7)
  (xii) 1,2,3,6-tetrahydropyridin-1-yl, (F-8)
  (xiii) 1-hexamethyleneimino containing a 3- or 4-double bond or 3- and 5-double bonds, (F-9)
  (xiv) 1,4-dihydro-1-pyridinyl substituted in the 4-position by two C$_1$-C$_3$ alkyl being the same or different, (F-10)
  (xv) —OH,
  (xvi) C$_1$-C$_3$ alkoxy,
  (xvii) —NR$_{M-7}$—(CH$_2$)$_e$—Q where Q is 2-pyridinyl where R$_{M-7}$ is —H or C$_1$-C$_3$ alkyl and e is 0 through 3,
  (xviii) pyridin-2-, 3- or 4-yl,
  (xix) —CF$_3$,
  (xx) —CCl$_3$,
  (xxi) —SCH$_3$, (b) 1,3,5-triazin-2-yl or the N-oxide thereof optionally substituted at the 4- and/or 6-position with R$_{M-2}$ is as defined above, (F-11)

(c) pyrimidin-4-yl or the N-oxide thereof optionally substituted at the 2- and/or 6-, and 5- and/or 6-position with R$_{M-2}$ is as defined above, (F-12)

(d) pyrimidin-2-yl optionally substituted at 4- and/or 6-position with 1 or 2 R$_{M-2}$ as is defined above, (F-13)

(e) pyrazin-2-yl optionally substituted with 1 or 2 R$_{M-2}$ as is defined above, (F-14)

(f) imidazol-2-yl optionally substituted in the 1 position with C$_1$-C$_3$ alkyl or -aryl, where aryl is as defined above, and further optionally substituted with 1 or 2 R$_{M-2}$ as defined above, (F-15)

(g) 1,3,4-triazol-2-yl optionally substituted in the 1 position with C$_1$-C$_3$ alkyl or -aryl, where aryl is as defined above, and further optionally substituted with R$_{M-2}$ as defined above, (F-16)

(h) imidazol-4- or 5-yl optionally substituted in the 1 position with C$_1$-C$_3$ alkyl or -aryl, where aryl is as defined above, and further optionally substituted with 1 or 2 R$_{M-2}$ as defined above, (F-17)

(i) benzo[b]thien-2-yl, (F-18)
(j) indol-2-yl, (F-19)
(k) benzo[b]thiazol-2-yl, (F-20)
(l) benzimidazol-2-yl, (F-21)
(m) 4-[2-[4-[2,6-bis(1-pyrrolidinyl)-4-pyrimidinyl]-1-piperazinyl]ethyl], (F-22)
(n) 1,2,4-triazin-3-yl optionally substituted at the 5- and/or 6-position with R$_{M-2}$ as is defined above, (F-23)

(2) —(CH$_2$)$_{2-4}$-(1-piperazinyl) optionally substituted in the 4-position with -aryl or -heteroaryl as defined above, (F-24)

(3) -heteroaryl, as defined above, (4) —(CH$_2$)$_m$—X$_4$ where m is as defined above and where X$_4$ is
  (a) —O—CH$_2$CH$_2$—Y, where Y is C$_1$-C$_3$ alkylamino, di(C$_1$-C$_3$)alkylamino where the alkyl groups are the same or different, $C_3-C_6$ alkyleneimino, optionally substituted with 1 or 2 $C_1-C_3$ alkyl, (b) $-NR_{M-5}CH_2CH_2-Y$, where $R_{M-5}$ is $-H$ or $C_1-C_3$ alkyl and Y is as defined above, (c) $-(CH_2)_g-N(R_{M-5})$-heteroaryl, where g is 2, 3 or 4, and where $R_{M-5}$ and heteroaryl are as defined above.

(5) $-(CH_2)_m-NR_{M-6}R_{M-8}$, where $R_{M-6}$ is $-H$ or $C_1-C_3$ alkyl and $R_{M-8}$ is -aryl or -heteroaryl as defined above, or $R_{M-6}$ and $R_{M-8}$ are taken together with the attached nitrogen atom to form a saturated mono-nitrogen $C_3-C_6$ heterocyclic ring and where m is as defined above, (6) $-(CHCH_3)_b-(CH_2)_f$-aryl where b is 0 and f is 1 through 4 or b is 1 and f is 0 through 3, where aryl is as defined above, (7) $-(CH_2)_i$-heteroaryl, where is 1 through 4 and heteroaryl is as defined above, (8) (1-piperazinyl)acetyl substituted in the 4-position by heteroaryl where heteroaryl is as defined above, (F-25)

(9) (1-piperazinyl)carbonylmethyl substituted in the 4-position by -heteroaryl where heteroaryl is as defined above, and (F-26) and (B) $R_B$ is (1) $-H$, (2) $C_1-C_3$ alkyl, (3) $C_5-C_7$ cycloalkyl, (4) $-(CH_2)_m-NR_{M-1}$-heteroaryl, where m, $R_{M-1}$ and heteroaryl are as defined above, (5) (1-piperazinyl)-$(C_2-C_4)$alkyl optionally substituted in the 4-position with -aryl or -heteroaryl as defined above, (F-24)

(6) $-(CH_2)_m-X_4$, where m and $X_4$ are as defined above, (7) $-(CH_2)_m-NR_{M-6}R_{M-8}$, where m, $R_{M-6}$ and $R_{M-8}$ are as defined above, (8) $-(CHCH_3)_b-(CH_2)_f-R_{M-9}$, where b, f and $R_{M-9}$ are as defined above, (9) 2-pyridinylmethyl,

(10) 2-phenylethyl, (C) $R_A$ and $R_B$ are taken together with the attached nitrogen atom to form a heterocyclic ring selected from the group consisting of (1) 2-(carboxy)-1-pyrrolidinyl optionally as the $C_1-C_3$ alkyl ester or as a pharmaceutically acceptable salt, (F-27)

(2) 2-(carboxy)-1-piperidinyl optionally as the $C_1-C_3$ alkyl ester or as a pharmaceutically acceptable salt, (F-28)

(3) 2-(carboxy)-1-hexamethyleneimino optionally as the $C_1-C_3$ alkyl ester or as a pharmaceutically acceptable salt, (F-29)

(4) 2-(carboxy)-1-heptamethyleneimino optionally as the $C_1-C_3$ alkyl ester or as a pharmaceutically acceptable salt, (F-30)

(5) 1-piperazinyl optionally substituted in the 4-position with $R_{M-12}-CO-(CH_2)_j-$ where $R_{M-12}$ is -aryl, -heteroaryl, $-NR_{M-13}$-heteroaryl and 2-furanyl, where $R_{M-13}$ is $-H$ or $C_1-C_3$ alkyl, where j is 0 through 3, and aryl and heteroaryl are as defined above, (F-31)

(6) 1-piperazinyl substituted in the 4-position with heteroaryl$(CH_2)_j$- where heteroaryl and j are as defined above with the proviso that j is not 1 when heteroaryl is 4-pyridinyl or 4-pyridinyl substituted with $C_1-C_3$ alkoxy, optionally substituted at the 2-position with $-NR_{44}R_{45}$ where $R_{44}$ and $R_{45}$ are the same or different and are $-H$, $C_1-C_3$ alkyl and where $R_{44}$ and $R_{45}$ can be taken together with the attached nitrogen atom to form 1-pyrrolidinyl, 1-morpholinyl and 1-piperidinyl, (F-32)

(7) 1-piperazinyl substituted in the 4-position with aryl—$(CH_2)_j$—, where aryl and j are as defined above with the proviso that j is not 1, (F-33)

(8) 4-hydroxy-1-piperidinyl substituted in the 4-position with aryl as defined above, (F-34)

(9) 1-piperazinyl substituted in the 4-position with heteroaryl—$NR_{M-13}$—CO—$(CH_2)_i$—, where heteroaryl, $R_{M-13}$ and i are as defined above;

(10) 1-piperazinyl substituted in the 4-position with —$(CH_2)_j$—$C^*$=C(2-pyridinyl)—N=N—C(2-pyridinyl)=$C^*$H, where * and j are as defined above, (F-36)

(11) 1-piperazinyl substituted in the 4-position with —$(CH_2)_i$—[4-[2,6-bis(1-pyrrolidinyl)-4-pyrimidinyl]-1-piperazine](F-37)

(12) 1-piperazinyl substituted in the 4-position with $C_1-C_3$ alkyl optionally substituted with 1 or 2 aryl, or (II) $-C^*$=C(2-pyridinyl)—N=N—C(2-pyridinyl)=$C^*$H where * is as defined above (18-2) $n_6$ is 0, $R_{16}$ is $R_{16-3}$:$R_{16-4}$ and $R_{25}$ is $R_{25-3}$:$R_{25-4}$ where one of $R_{16-3}$ and $R_{16-4}$ is taken together with one of $R_{25-3}$ and $R_{25-4}$ to form a second bond between the carbon atoms to which $R_{16}$ and $R_{25}$ are attached and the other of $R_{16-3}$ and $R_{16-4}$ is —$X_3$—M where $X_3$ and M are as defined above and the other of $R_{25-3}$ and $R_{25-4}$ is —H, (18-3) $n_6$ is 1, $R_{25}$ is $R_{25-5}$ and $R_{25-6}$ and $R_{26}$ is $R_{26-5}$ and $R_{26-6}$ where one of $R_{25-5}$ and $R_{25-6}$ and one of $R_{26}$ is $R_{26-5}$ and $R_{26-6}$ are taken together to form a second bond between the carbon atoms to which $R_{25}$ and $R_{26}$ are attached and the other of $R_{25-5}$ and $R_{25-6}$ and $R_{26-5}$ and $R_{26-6}$ are —H, and pharmaceutically acceptable salts thereof, and hydrates and solvates thereof.

Another preferred embodiment of the bicyclic amines of formula (III) is where:

$W_2$ is —O—, —S—, —$NR_{54}$— where $R_{54}$ is —H or $C_1-C_3$ alkyl, $n_6$ is 0, 1 or 2, $R_7$ is —H, —CO—$(C_1-C_4$ alkyl), —CO—$\phi$ or -prodrug where prodrug is $-PO_2-O^-$, $-CO-CH_2-CO-NH-CH_2-SO_2-O^-$, $-CO-(CH_2)_{n21}-R_{51}$ where $n_{21}$ is 1-7 and $R_{51}$ is —COO$^-$, —$NR_{51-1}R_{51-2}$ and $R_{51-2}$ are the same or different and are —H or $C_1-C_3$ alkyl, —$N^+R_{51-1}R_{51-2}R_{51-3}$halide$^-$ where $R_{51-1}R_{51-2}R_{51-3}$ are the same or different and are —H or $C_1-C_3$ alkyl, and where halide is —Cl or —Br, $-CO-CH=CH-CO-O^-$, $-CO-N^*-CH=CH-N=CH^*$ where the atoms marked with an asterisk (*) are bonded to each other resulting in the formation of a ring, $$-CO-C^*=C[(CH_2)_{n22}-NH_2]-CH=CH-CH=CH^*$$

where $n_{22}$ is 1 or 2 and where the atoms marked with an asterisk (*) are bonded to each other resulting in the formation of a ring, $$-CO-C^*=CH-CH=C(-NR_{52})-CH=CH^*$$

where $R_{52}$ is —H or $C_1$-$C_3$ alkyl and where the atoms marked with an asterisk (*) are bonded to each other resulting in the formation of a ring, $$-CO-(CH_2)_{n21}-CO-O-[C_6H_{12}O_6\ sugars].$$

$$-CO-O-CH(CH_2-O-CO-R_{53})_2$$

where the $R_{53}$'s are the same or different and are $C_1$-$C_{18}$, $$-CO-(CH_2)_6-CO-N(CH_3)-CH_2-CH_2-SO_3^- cation^-$$

where cation⁻ is sodium, potassium or trialkylammonium where alkyl is $C_1$-$C_3$, $$-CH_2-O-CO-(CH_2)_{n21}-NR_{51-1}R_{51-2}$$

where $n_{21}$, $R_{51-1}$ and $R_{51-2}$ are as defined above, $$-CO-NH-C_6H_4-R_{55}$$

where $R_{55}$ is —H or $C_1$-$C_3$ alkyl, —NO$_2$, —NR$_{51-1}$R$_{51-2}$ where $R_{51-1}$ and $R_{51-2}$ are as defined above and $R_{10}$ is —H or —CH$_3$,
$R_{11}$ is —H or —CH$_3$,
$R_{12}$ is —H or —CH$_3$, (18-1) $R_{16}$ is $\alpha$-$R_{16-1}$:$\beta$-$R_{16-2}$ is —H, —CH$_3$, —CH$_2$CH$_3$ or —$\phi$ and the other is —X$_3$—M where X$_3$ is —CO—, —(CH$_2$)$_{n16}$—CO— where $n_{16}$ is 1 or 2, —(CH$_2$)$_{n3}$— where $n_3$ is 1-6, or —CO—O—(CH$_2$)$_{n15}$— where $n_{15}$ is 2-6, $R_{25}$ and $R_{26}$ are —H:—H and where M is (I) —NR$_A$R$_B$ where:

(A) $R_A$ is (1) —(CH$_2$)$_m$—NR$_{M-1}$-heteroaryl, where m is 2, 3 or 4, where $R_{M-1}$ is —H or $C_1$-$C_3$ alkyl, where heteroaryl is:

(a) pyridin-2-(F-1), 3- (F-2) or 4-yl (F-3) or the N-oxide thereof optionally substituted by 1 or 2 $R_{M-2}$, being the same or different, where $R_{M-2}$ is
  (i) —F,
  (ii) —Cl,
  (iii) —Br,
  (iv) $C_1$-$C_5$ alkyl,
  (v) —CH$_2$—CH=CH$_2$,
  (vi) -aryl, where aryl is phenyl optionally substituted with 1 through 2 —F, —Cl, —Br, $C_1$-$C_3$ alkoxy, —COOH, —NH$_2$, $C_1$-$C_3$ alkylamino, di($C_1$-$C_3$)alkylamino, where the alkyl groups are the same or different, 1-pyrrolidinyl-, 1-piperidinyl, 1-hexamethylenimino-, 1-heptamethylenimino-, $C_2$-$C_4$ acylamino, —NH—CHO, with 1—F or —CF$_3$ or with 3,4-methylenedioxy and 3,4-ethylenedioxy;
  (vii) —NR$_{M-3}$R$_{M-3}$ where the $R_{M-3}$s are the same or different and are —H, $C_1$-$C_3$ alkyl or —CH$_2$—CH=CH$_2$,
  (viiiα) *CH$_2$—(CH$_2$)$_q$—CH$_2$—N*— where the atoms marked with an asterisk (*) are bonded to each other resulting in the formation of a ring, where q is 1 through 5,
  (viiiβ) *CH$_2$—(CH$_2$)$_c$—G—(CH$_2$)$_d$—CH$_2$—N*— where the atoms marked with an asterisk (*) are bonded to each other resulting in the formation of a ring (F-4), where G is —O—, —S—, —SO—, —SO$_2$— or —NR$_{M-4}$—, where $R_{M-4}$ is —H, $C_1$-$C_3$ alkyl, or aryl as defined above, where c and d are the same or different and are 0 through 2 with the proviso that the total number of ring carbon atoms is 4, 5 or 6,
  (ix) 3-pyrrolin-1-yl, (F-5)
  (x) pyrrol-1-yl optionally substituted with $C_1$-$C_3$ alkyl, (F-6)
  (xi) piperidin-1-yl optionally substituted with 1 or 2 $C_1$-$C_3$ alkyl, (F-7)
  (xii) 1,2,3,6-tetrahydropyridin-1-yl, (F-8)
  (xiii) 1-hexamethyleneimino containing a 3- or 4-double bond or 3- and 5-double bonds, (F-9)
  (xiv) 1,4-dihydro-1-pyridinyl substituted in the 4 position by two $C_1$-$C_3$ alkyl being the same or different, (F-10)
  (xv) —OH,
  (xvi) $C_1$-$C_3$ alkoxy,
  (xvii) —NR$_{M-7}$—(CH$_2$)$_e$—Q where is 2-pyridinyl where $R_{M-7}$ is —H or $C_1$-$C_3$ alkyl and e is 0 through 3,
  (xviii) pyridin-2-, 3- or 4-yl,
  (xix) —CF$_3$,
  (xx) —CCl$_3$,
  (xxi) —SCH$_3$,
 (b) 1,3,5-triazin-2-yl or the N-oxide thereof optionally substituted at the 4- and/or 6-position with $R_{M-2}$ is as defined above, (F-11)
 (c) pyrimidin-4-yl or the N-oxide thereof optionally substituted at the 2- and/or 6-, and 5- and/or 6-position with $R_{M-2}$ is as defined above, (F-12)
 (d) pyrimidin-2-yl optionally substituted at 4- and/or 6-position with 1 or 2 $R_{M-2}$ as defined above, (F-13)
 (e) pyrazin-2-yl optionally substituted with 1 or 2 $R_{M-2}$ as is defined above, (F-14)
 (f) imidazol-2-yl optionally substituted in the 1 position with $C_1$-$C_3$ alkyl or -aryl, where aryl is as defined above, and further optionally substituted with 1 or 2 $R_{M-2}$ as defined above, (F-15)
 (g) 1,3,4-triazol-2-yl optionally substituted in the 1 position with $C_1$-$C_3$ alkyl or -aryl, where aryl is as defined above, and further optionally substituted with $R_{M-2}$ as defined above, (F-16)
 (h) imidazol-4- or 5-yl optionally substituted in the 1 position with $C_1$-$C_3$ alkyl or -aryl, where aryl is as defined above, and further optionally substituted with 1 or 2 $R_{M-2}$ as defined above, (F-17)
 (i) benzo[b]thien-2-yl, (F-18)
 (j) indol-2-yl, (F-19)

(k) benzo[b]thiazol-2-yl, (F-20)
(l) benzimidazol-2-yl, (F-21)
(m)   4-[2-[4-[2,6-bis(1-pyrrolidinyl)-4-pyrimidinyl]-1-piperazinyl]ethyl], (F-22)
(n) 1,2,4-triazin-3-yl optionally substituted at the 5- and/or 6-position with $R_{M-2}$ as is defined above, (F-23)

(2) —$(CH_2)_{2-4}$-(1-piperazinyl) optionally substituted in the 4-position with -aryl or -heteroaryl as defined above, (F-24)

(3) -heteroaryl, as defined above, (4) —$(CH_2)_m$—$X_4$ where m is as defined above and where $X_4$ is
  (a) —$O$—$CH_2CH_2$—Y, where Y is $C_1$-$C_3$ alkylamino, di($C_1$-$C_3$)alkylamino where the alkyl groups are the same or different, $C_3$-$C_6$ alkyleneimino, optionally substituted with 1 or 2 $C_1$-$C_3$ alkyl,
  (b) —$NR_{M-5}CH_2CH_2$—Y, where $R_{M-5}$ is —H or $C_1$-$C_3$ alkyl and Y is as defined above,
  (c) —$(CH_2)_g$—$N(R_{M-5})$-heteroaryl, where g is 2, 3 or 4, and where $R_{M-5}$ and heteroaryl are as defined above, (5) —$(CH_2)_m$—$NR_{M-6}R_{M-8}$, where $R_{M-6}$ is —H or $C_1$-$C_3$ alkyl and $R_{M-8}$ is -aryl or -heteroaryl as defined above, or $R_{M-6}$ and $R_{M-8}$ are taken together with the attached nitrogen atom to form a saturated mono-nitrogen $C_3$-$C_6$ heterocyclic ring and where m is as defined above, (6) —$(CHCH_3)_b$—$(CH_2)_f$—aryl where b is 0 and f is 1 through 4 or b is 1 and f is 0 through 3, where aryl is as defined above, (7) —$(CH_2)_i$—heteroaryl, where i is 1 through 4 and heteroaryl is as defined above, (8) (1-piperazinyl)acetyl substituted in the 4-position by heteroaryl where heteroaryl is as defined above, (F-25)

(9) (1-piperazinyl)carbonylmethyl substituted in the 4-position by -heteroaryl where heteroaryl is as defined above, and (F-26) and (B) $R_B$ is
(1) —H,
(2) $C_1$-$C_3$ alkyl,
(3) $C_5$-$C_7$ cycloalkyl,
(4) —$(CH_2)_m$—$NR_{M-1}$-heteroaryl, where m, $R_{M-1}$ and heteroaryl are as defined above,
(5) (1-piperazinyl)-($C_2$-$C_4$)alkyl optionally substituted in the 4-position with -aryl or -heteroaryl as defined above, (F-24)
(6) —$(CH_2)_m$—$X_4$, where m and $X_4$ are as defined above,
(7) —$(CH_2)_m$—$NR_{M-6}R_{M-8}$, where m, $R_{M-6}$ and $R_{M-8}$ are as defined above,
(8) —$(CHCH_3)_b$—$(CH_2)_f$—$R_{M-9}$, where b, f and $R_{M-9}$ are as defined above,
(9) 2-pyridinylmethyl,
(10) 2-phenylethyl, (C) $R_A$ and $R_B$ are taken together with the attached nitrogen atom to form a heterocyclic ring selected from the group consisting of
(1) 2-(carboxy)-1-pyrrolidinyl optionally as the $C_1$-$C_3$ alkyl ester or as a pharmaceutically acceptable salt, (F-27)
(2) 2-(carboxy)-1-piperidinyl optionally as the $C_1$-$C_3$ alkyl ester or as a pharmaceutically acceptable salt, (F-28)
(3) 2-(carboxy)-1-hexamethyleneimino optionally as the $C_1$-$C_3$ alkyl ester or as a pharmaceutically acceptable salt, (F-29)
(4) 2-(carboxy)-1-heptamethyleneimino optionally as the $C_1$-$C_3$ alkyl ester or as a pharmaceutically acceptable salt, (F-30)
(5) 1-piperazinyl optionally substituted in the 4-position with $R_{M-12}$—$CO$—$(CH_2)_j$— where $R_{M-12}$ is -aryl, -heteroaryl, —$NR_{M-13}$-heteroaryl and 2-furanyl, where $R_{M-13}$ is —H or $C_1$-$C_3$ alkyl, where j is 0 through 3, and aryl and heteroaryl are as defined above, (F-31)
(6) 1-piperazinyl substituted in the 4-position with heteroaryl$(CH_2)_j$—where heteroaryl and j are as defined above, (F-32)
(7) 1-piperazinyl substituted in the 4-position with aryl—$(CH_2)_j$—, where aryl and j are as defined above, (F-33)
(8) 4-hydroxy-1-piperidinyl substituted in the 4-position with aryl as defined above, (F-34)
(9) 1-piperazinyl substituted in the 4-position with heteroaryl—$NR_{M-13}$—$CO$—$(CH_2)_i$—, where heteroaryl, $R_{M-13}$ and i are as defined above; (F-35)
(10) 1-piperazinyl substituted in the 4-position with —$(CH_2)_j$—$C^*$=$C$(2-pyridinyl)—$N$=$N$—$C$(2-pyridinyl)=$C^*H$, where * and j are as defined above, (F-36)
(11) 1piperazinyl substituted in the 4-position with —$(CH_2)_i$—[4-[2,6-bis(1-pyrrolidinyl)-4-pyrimidinyl]-1-piperazine] (F-37)
(12) 1-piperazinyl substituted in the 4-position with $C_1$-$C_3$ alkyl optionally substituted with 1 or 2 aryl, or (II)   —$C^*$=$C$(2-pyridinyl)—$N$=$N$—$C$(2-pyridinyl)=$C^*H$ where * is as defined above (18-2) $n_6$ is 0, $R_{16}$ is $R_{16-3}$:$R_{16-4}$ and $R_{25}$ is $R_{25-3}$:$R_{25-4}$ where one of $R_{16-3}$ and $R_{16-4}$ is taken together with one of $R_{25-3}$ and $R_{25-4}$ to form a second bond between the carbon atoms to which $R_{16}$ and $R_{25}$ are attached and the other of $R_{16-3}$ and $R_{16-4}$ is —$X_3$—M where $X_3$ and M are as defined above and the other of $R_{25-3}$ and $R_{25-4}$ is —H, (18-3) $n_6$ is 1, $R_{25}$ is $R_{25-5}$ and $R_{25-6}$ and $R_{26}$ is $R_{26-5}$ and $R_{26-6}$ where one of $R_{25-5}$ and $R_{25-6}$ and one of $R_{26}$ is $R_{26-5}$ and $R_{26-6}$ are taken together to form a second bond between the carbon atoms to which $R_{25}$ and $R_{26}$ are attached and the other of $R_{25-5}$ and $R_{25-6}$ and $R_{26-5}$ and $R_{26-6}$ are —H, and pharmaceutically acceptable salts thereof, and hydrates and solvates thereof.

Preferred compounds are where $R_7$ is —H; where $R_{10}$, $R_{11}$ and $R_{12}$ are all —$CH_3$; where $n_6$ is 1; where one of $R_{16-1}$ or $R_{16-2}$ is —$CH_3$; where $X_3$ is —CO— or —$CH_2$—; where $W_2$ is —O— and the compounds of EXAMPLES 18-23, 66-68, 75, 78-82, 84-94, 96, 99-124, 129-143, 145-164 and 178-181.

Disclosed are the cycloalkene amines of formula (IV) where:
  $n_4$ is 1-14,
  $n_5$ is 1-3 and where
  M is as defined above for the aromatic amines (I) and pharmaceutically acceptable salts thereof, and hydrates and solvates thereof. Preferred compounds are where $n_5$ is 2; and where $n_4$ is 3-6 and the compounds of EXAMPLES 60-64.

Also disclosed are the aromatic bicyclic amines of formula (V) where $n_8$ is 1 or 2.

$R_{18}$, $R_{19}$, $R_{20}$ and $R_{21}$ are the same or different and are —H, —OH, —Cl, —Br, -$C_1$-$C_3$ alkyl, $C_1$-$C_3$ alkoxy, and where any two adjacent groups are be taken together to form o-methylenedioxy, where one of $R_{18}$, $R_{19}$, $R_{20}$ and $R_{21}$ is —OH, alkoxy or o-methylenedioxy, $R_{17}$ is $\alpha$—$R_{17\text{-}1}$:$\beta$—$R_{17\text{-}2}$ where one of $R_{17\text{-}1}$ and $R_{17\text{-}2}$ is —H or —$CH_3$ and the other is (I-$R_{17}$) —$(CH_2)_{n9}$—$W_1$ where $n_9$ is 1, 2 or 3 and $W_1$ is selected from the group consisting of 2,6-bis(1-pyrrolidinyl)-4-(1-piperazinyl)-pyrimidine, 3-(ethylamino)-2-(1-piperazinyl)pyridine, 2,6-bis(2-pyridinyl)-4-(1-piperazinyl)pyridine, 3,6-bis(2-pyridinyl)-4-(methyl-[1-piperazinyl])-pyridazine, 6-methoxy-2-morpholino-4-(1-piperazinyl)-pyrimidine (II-$R_{17}$) —$(CH_2)_{n10}$—O—$(CH_2)_{n11}$—O—$(CH_2)_{n12}$—$W_1$ where $n_{10}$ is 1 or 2, $n_{11}$ is 1, 2 or 3 and $n_{12}$ is 1 or 2 and where $W_1$ is as defined above and pharmaceutically acceptable salts thereof, and hydrates and solvates thereof. Preferred are compounds where $R_{17\text{-}1}$ or $R_{17\text{-}2}$ is —$(CH_2)_{n9}$—$W_1$ and the compounds of EXAMPLES 53–55.

Disclosed are the hydroquinone (VI) and corresponding quinone (VII) amines where $R_{27}$ and $R_{28}$ are the same or different and are —H, $C_1$-$C_3$ alkyl, $C_1$-$C_4$ acyl, —CO—$\phi$ where $\phi$ is optionally substituted with —F, —Cl, —Br, —OH, $C_1$-$C_3$ alkoxy, —$NO_2$, —$N(CH_3)_2$, —$CH_2$—$\phi$ and —$Si(CH_3)_2$—$C(CH_3)_3$ and -prodrug where prodrug is as defined for the aromatic amines (I) and $R_{29}$, $R_{30}$ and $R_{31}$ are the same or different and are —H, -$C_1$-$C_4$ alkyl and $C_1$-$C_3$ alkoxy, $n_{18}$ is 1–20, M is as defined for the aromatic amines (I) and pharmaceutically acceptable salts thereof, and hydrates and solvates thereof. Preferred are the compounds where $n_{18}$ is 1–4, $R_{27}$ and $R_{28}$ are —H or $C_1$-$C_4$ acyl, and $R_{29}$, $R_{30}$ and $R_{31}$ are —$CH_3$ and the compounds of EXAMPLES 165–174.

Also disclosed are the amino-ethers (VIII) where $R_{32}$ is =O or —H:—H, $R_{33}$ and $R_{34}$ are the same or different and are —H or $C_1$-$C_3$ alkyl, $R_{35}$, $R_{36}$ and $R_{38}$ are the same or different and are —H, -$C_1$-$C_4$ alkyl and $C_1$-$C_3$ alkoxy, $R_{37}$ is —H, $C_1$-$C_3$ alkyl, $C_1$-$C_4$ acyl, —CO—$\phi$ where $\phi$ is optionally substituted with —Cl, —Br, —OH, $C_1$-$C_3$ alkoxy, —$NO_2$, —$N(CH_3)_2$, —$CH_2$—$\phi$, —$Si(CH_3)_2$—$C(CH_3)_3$ and -prodrug where prodrug and $R_4$ are as defined for the aromatic amines (I) and pharmaceutically acceptable salts thereof, and hydrates and solvates thereof. Preferred amino-ethers are wherr $R_{33}$ and $R_{34}$ are the same and are —H:—H or —$CH_3$:—$CH_3$, $R_{35}$, $R_{36}$ and $R_{38}$ are —$CH_3$ or t-butyl, $R_{37}$ is —H or $C_1$-$C_4$ acyl and the compounds of EXAMPLES 175–177.

Further disclosed are the bicyclic amino ether amines (IX which includes IXA and IXB) where where $A_1$ and $A_2$ taken together are —O—$(CH_2)_{n20}$—C(=$R_{50}$)—N($R_4$)— and

—N($R_4$)—C(=$R_{50}$)—$(CH_2)_{n20}$—O— where $n_{20}$ is 0–3, $R_{50}$ is =O or —H:—H and $R_{47}$ is —H or -prodrug where prodrug and $R_4$ are as defined for the aromatic amines (I) and pharmaceutically acceptable salts thereof, and hydrates and solvents thereof. Preferred are the compounds where $R_{47}$ is —H and where $R_{46}$, $R_{48}$ and $R_{49}$ are —H, —$CH_3$ or t-butyl and the compounds of EXAMPLES 185–188.

Disclosed is a method of treating spinal trauma, mild and/or moderate to severe head injury, subarachnoid hemorrhage and subsequent cerebral vasospasm, ischemic (thromboembolic) stroke, excess mucous secretion, asthma, muscular dystrophy, adriamycin-induced cardiac toxicity, Parkinsonism, Alzheimer's disease, other degenerative neurological disorders, multiple sclerosis, organ damage during reperfusion after transplant, skin graft rejection, hemorrhagic, traumatic and septic shock, and conditions such as severe burns, ARDS, inflammatory diseases such as osteo- or rheumatoid arthritis, nepthrotic syndrome (immunological), systemic lupus erythematosis, allergic reactions, atherosclerosis, inflammation (for example dermatological, inflammatory and psoriasis conditions), emphysema, stress induced ulcers, cluster headaches, complications from brain tumors (e.g. peritumoral edema), radiation damage (for example during reaiation treatment or from accidental exposure to radiation), damage after MI, pre-birth infant strangulation and infant hypoxia syndrome, such opthalmic disorders as uveitis and optic neuritis, and malignant hperthermia as well as preventing damage following cardiopulmonary resuscitation, neurological or cardiovascular surgery and from cardiac infarction which comprises administering an effective amount of a 3,4-dihydrobenzopyran of formula (XI) where $R_{39}$ is —H or —$CH_3$, $R_{40}$ is —H, $C_1$-$C_4$ alkyl, $C_1$-$C_4$ alkenyloxy, $R_{41}$ is —H or —$CH_3$, $R_{42}$ is —H or —$CH_3$, $R_{43}$ is $\alpha$—$R_{43\text{-}1}$:$\beta$—$R_{43\text{-}2}$ where one of $R_{43\text{-}1}$ and $R_{43\text{-}2}$ is —H, —$CH_3$, —$CH_2CH_3$ or —$\phi$ and the other is —$(CH_2)_{n17}$-(1-piperazinyl substituted in the 4 position with —$CH_2$—$\phi$ or 4-pyridinylmethyl where each can be optionally substituted with 1–4 $C_1$-$C_3$ alkoxy) where $n_{17}$ is 1–3 or —$(CH_2)_{n18}$—CO—(1-piperazinyl substituted in the 4 position with with —$CH_2$—$\phi$ or 4-pyridinylmethyl where each can be optionally substituted with 1–4 $C_1$-$C_3$ alkoxy) where $n_{18}$ is 0–2 pharmaceutically acceptable salts thereof, and hydrates and solvates thereof to a human who is in need of such treatment. It is preferred that the treatment be treating spinal trauma, mild and/or moderate to severe head injury, asthma and damage after MI. It is preferred that the effective amount is from about 0.05 to about 10 mg/kg/day IV or about 0.5 to about 50 mg/kg/day, one to four times daily by mouth. It is preferred that the compounds of EXAMPLES 83, 95, 125, 183 and 184 be used in the treatment.

DETAILED DESCRIPTION OF THE INVENTION

The aromatic amines (I) are produced by condensing the amine corresponding to the desired aromatic amine (I) with the non-amine portion corresponding to the desired aromatic amine (I). With regard to the non-amine portion, when $R_1$ and $R_2$ are not —H, and $R_3$ is —OH, $C_1$-$C_3$ alkoxy or —O—CO—($C_1$-$C_4$ alkyl) the non-amine portion is produced by starting with the desired aromatic ring such as the phenol and alkylating it with the appropriate unsaturated halide, such as allyl bromide (for $n_1=2$) to form the unsaturated phenolic ether. This compound is then rearranged to give the unsaturated group para to the $R_3$ group by the procedure of Tarbell & Kincaid see, J. Am. Chem. Soc., 62, 728 (1940). The terminal unsaturated group is then transformed to the alcohol by known methods, which is then converted to a good leaving group such as chloride, bromide, iodide, mesylate, tosylate, etc and this compound is then condensed with the appropriate amine by the procedures disclosed in PCT 86/01797. Suitable solvents include acetonitrile, THF and DMF; acetonitrile is preferred. Suitable bases include carbonate, bicarbonate and TEA; preferred is carbonate. While not necessary, it is preferred, to add a catalytic amount of iodide ion when reacting the non-amine and amine portion to produce the desired aromatic amine (I). When $R_3$ is —H, it is preferred to start with the appropriate substituted benzoic acid or benzaldehyde derivative. Here again the side chain is built up to the desired length, a good leaving group added and then condensed with the appropriate amine. The compounds where $X_1$ is —CH$_2$— and $n_1$ is 0 are preferred by reducing Ar—CHO or Ar—COOH (Ar refers to φ with the appropriate variable substituents as defined in the claims for the aromatic amines (I)) with lithium aluminum hydride to Ar—CH$_2$—OH. The mesylate or tosylate of the alcohol is prepared in the usual way (using mesyl or tosyl chloride and triethylamine in methylene chloride) and it is then reacted with the appropriate amine (except A-55 which is generated in situ, this exception will be understood to apply in all cases) to yield the desired product. Alternatively, one can react Ar—H and chloromethylate with paraformaldehyde and concentrated hydrochloric acid. This reaction works best if the aromatic ring is activated by one or more alkoxy groups. The product, ArCH2Cl, is then reacted with the appropriate amine. When $X_1$ is —CH$_2$— and $n_1$ is 1, the above procedure can be followed starting with the corresponding Ar—CH$_2$—CHO or Ar—CH$_2$—COOH. Alternatively, one can begin with a phenol which is unsubstituted at either the ortho or para positions. The allyl ether is prepared in the usual way from allyl chloride and the phenol. Next the allyl ether is thermally rearranged in a Claissen Rearrangement. If the phenol is substituted at C-2 and C-6 positions, the rearrangement will give a 4—CH$_2$CH=CH$_2$ substituent. This can be cleaved by ozone and reduced to the 4—CH$_2$CH$_2$OH group. The chloride/bromide/iodide/mesylate/tosylate is prepared from this alcohol in the usual way and reacted with the appropriate amine. Where $X_1$ is —CH$_2$— and $n_1$ is 2, the above method produces a phenol having a —CH$_2$CH=CH$_2$ group. This olefin is reacted with diborane in the usual way to form the organoborane which is then oxidized with hydrogen peroxide and base to the terminal alcohol- CH$_2$CH$_2$CH$_2$OH. The leaving group and reaction with the appropriate amine are performed in the usual manner. Alternatively, one can begin with Ar—CHO, which is reacted with malonic acid and a weak base to form Ar—CH=CHCOOH which can be hydrogenated and reduced with lithium aluminum hydride to Ar—CH$_2$CH$_2$CH$_2$OH [J. Med. Chem., 751, (1980)] which can be converted in the usual way to the aromatic amine (I). When $X_1$ is —CH$_2$— and $n_1$ is 3, it is preferred to begin with a substituted anisole which is unsubstituted at C-2 or C-4. This is reacted with succinic anhydride and aluminum chloride in benzene or toluene. The product, Ar—COCH$_2$CH$_2$COOH, is reduced with diborane in THF, followed sometimes by hydrogenation over Palladium on carbon in acetic acid, to the desired Ar—CH$_2$CH$_2$CH$_2$CH$_2$OH which is converted to the aromatic amine (I). When $X_1$ is —CH$_2$— and $n_1$ is 4, 5 or 6, it is preferred to first prepare a Grignard reagent from Ar-Br. The Grignard reagent is reacted with the appropriate 5-7 membered cyclic ketone. The alcohol product is oxidized and cleaved to the keto-acid which is reduced with boron hydride to the alcohol Ar—(CH2)$_{4-6}$CH$_2$OH which is converted to the aromatic amine in the usual way.

The aromatic amines (I) where $X_1$ is —CR(CH$_3$)— and $n_1$ is 1 are prepared by reacting the amine M with a haloketone such as chloroacetone. The adduct, CH$_3$COCH$_2$—M, is reacted with a Grignard such as Ar—MgBr. The product has the above structure when R is —OH. The alcohol can be acetylated and reduced to give R=—H. The aromatic amines (I) where $X_1$ is —O— are prepared by begining with the corresponding phenol. This is reacted with the dibromide Br(CH$_2$)$_{n1}$—Br (or the corresponding dichloride) where $n_1$ is 4, 5, 6 in the presence of hydroxide and in an alcoholic solvent such as ethanol. The product, Ar—O—(CH$_2$)$_{n1}$—Br, is reacted with the amine M in a solvent such as acetonitrile in the presence of a base such as carbonate to yield the desired product. Alternatively, starting with the same phenol, it is reacted with chloroethanol in an alcoholic solvent in the presence of hydroxide to give Ar—O—CH$_2$CH$_2$OH, which is converted to the aromatic amine (I) is the usual manner. For aromatic amines (I) where $X_1$ is —CO— it is preferred to start with the known compounds where Ar—CO—(CH$_2$)$_{n1}$—halogen. The halide is then reacted with the appropriate amine in the ususal manner to produce the aromatic amine (I). Where $X_1$ is —CH(OH)—, one starts with product above ($X_1$ is —CO—) and reduces it with a reducing agent such as sodium borohydride in ethanol. For the aromatic amines (I) where $X_1$ is —C(OH)(R$_{13}$)— where R$_{13}$ is C$_1$-C$_3$ alkyl or phenyl (optionally substituted) these compounds are prepared by reaction of the compounds where $X_1$ is —CO— with the appropriate Grignard reagent (R$_{13}$—Mg—X). For the aromatic amines (I), where $X_1$ is —N(R$_4$)—, known anilines are the starting materials. The corresponding amides are formed by reaction of the aniline with an acid chloride (R$_4$—COCl) or anhydride R$_4$—CO$_3$C—R$_4$ in the presence of a base such as triethylamine in a solvent such as methylene chloride. The resulting amides are reduced with lithium aluminum hydride to Ar—NH(R$_4$). These compounds are reacted with the dibromide Br(CH2)$_{n1}$Br or analogous dichloride or diiodide where n=4, 5, 6 in the presence of hydroxide and in an alcoholic solvent such as ethanol. The product, Ar—N(R$_4$)(CH$_2$)$_{n1}$Br, is reacted with the amine, M, in acetonitrile in the presence of carbonate to give the aromatic amine (I).

For the aromatic amines (I) where $n_{13}$ is 1, Ar—X$_1$—C$_{n1}$(R$_8$)(R$_9$)—O—(CH$_2$)$_{n14}$, where $x_1$ is not —NH—CO— or —NR$_4$— and $n_1$ is 2 or more it is preferred to begin with the compound Ar—X$_1$—C$_{n1}$(R$_8$)(R$_9$)—OH and convert it to the halide, mesylate or tosylate in the usual way. This is reacted with HO—(CH$_2$)$_{n14}$—O—Protecting group where the protecting group is tetrahydropyranyl or trimethylsilyl in the presence of a base such as sodium hydride or potassium t-butoxide. Next the protecting group is removed to give Ar—X-

1—$C_{n1}(R_8)(R_9)$—O—$(CH_2)_{n14}$—OH. The terminal alcohol is converted to the mesylate, tosylate, or halide and reacted with the appropriate amine in the usual way to obtain the desired product.

With regard to isolation, the compounds are generally isolated by extraction between sodium bicarbonate and methylene chloride. The organic phase is washed and dried in the usual manner and concentrated. When necessary, the products are purified by silica gel chromatography eluting with either methanol and methylene chloride or ethyl acetate and hexane.

The alkyl amines (II) are produced by condensing the amine corresponding to the desired alkyl amine (II) with the non-amine portion corresponding to the desired alkyl amine (II) by the proceedures disclosed in PCT 86/01797. The non-amine portion should have a good leaving group such as mesylate, tosylate, —Br, etc. While not necessary it is preferred to add a catalytic amount of iodide ion, see EXAMPLE 1. In the case of certain 3,6-bis(2-pyridinyl)pyridazines (A-55) the amine is not preformed and then attached to the non-amine portion; the amine is formed in situ, see EXAMPLE 17.

The bicyclic amines (III) are prepared from the corresponding amine and bicyclic portions by means well known to those skilled in the art. The bicyclic portions where the terminal group is —COOH are known or can readily be produced from known compounds, see U.S. Pat. Nos. 3,947,473, 4,003,919, 4,018,799, 4,026,907 and 4,681,890. The acid can be activated with an agent such as 1,1'-carbonyldiimidazole or 1,3-dicyclohexylcarbodiimide in a solvent such as THF, ether or methylene chloride following which it is contacted with the desired amine to form the desired bicyclic amine where $X_3$ is —CO—. Alternatively, the related acid chlorides can be used to react with the desired amine, see EXAMPLE 68. In the cases where $X_3$ is —$(CH_2)_{n3}$—, the methylene compounds are formed by first forming the amide as above then reducing it with a reducing agent such as lithium aluminum hydride or borane dimethylsulfide. Alternatively, though less preferrably, the —COOH group can be reduced to the corresponding —$CH_2$—OH which can then be transformed to a good leaving group such as mesylate, tosylate or bromide and then reacted with the desired amine to form the desired corresponding bicyclic amine (III). In the case where $X_3$ is —CO—O—, the phenol acetate (or other ester) of 6-hydroxy-2,5,7,8-tetramethychroman-2-carboxylic acid is activated with oxalyl chloride in a solvent such as acetonitrile, see Helv. Chim. Acta 61, 1675 (1978). A solution of the requisite aminoalcohol in pyridine or pyridine/acetonitrile is added. The reaction mixture is allowed to stand several hours at 20°-20°, followed by workup. The reaction mixture is partitioned between methylene chloride and aqueous sodium bicarbonate. The phases are separated, the organic phase is dried, concentrated, chromatographed, if needed, over silica gel to give the bicyclic amine (III) where $X_3$ is —CO—O—. See EXAMPLES 161 and 162.

A general procedure for synthesis of the amide type ($X_3$ is —CO—) bicyclic amines (III) is as follows. 1,1'-Carbonyldiimidazole (1.1 equivalents) is added to a stirred solution of non-amine portion of the starting material (6-hydroxy-2,5,7,8-tetramethylchroman-2-carboxylic acid) about 4-8 mmol in THF (10-12 ml). The mixture is stirred at 20°-25° for 30-60 min. and the appropriate amine (1.0-1.1 equivalents) in THF or methylene chloride (10-20 ml) is added dropwise and the mixture stirred at 20°-25° for 4-18 hr (monitored by TLC). When the reaction is complete the mixture is concentrated under reduced pressure and partitioned between ether (100-150 ml) and water (100-150 ml). The ether phase is washed with water, saline, dried over sodium sulfate and the solvent removed under reduced pressure. If purification is necessary, column chromatography is performed as needed on silica gel. In some cases the products containing basic nitrogen atoms are converted to acid addition salts.

A general procedure for reduction of the amide type ($X_3$ is —CO—) to the reduced type ($X_3$ is —$CH_2$—) of bicyclic amine (III) is as follows. To a stirred suspension of lithium aluminum hydride (LAH, 4 molar equivalents) in dry THF (20-25 ml), maintained at 0°-50° depending on the nature of the particular compound, is added dropwise over 10-15 min a solution of the appropriate amide (4-8 mmol) in dry THF (25-50 ml). The mixture is stirred at the appropriate temperature for 30-120 min and then cooled in an ice-water bath. To the reaction mixture is carefully added dropwise water (1 ml/g of LAH), followed by aqueous sodium hydroxide (15%, 1 ml/g of LAH) and finally water (3 ml/g of LAH). The mixture is stirred for 30 min and filtered through celite. The filtered solids are washed with ether (50-100 ml, 2 times). The combined washes and filtrate were extracted with aqueous hydrogen chloride (10%, 50-75 ml, 2 times). The pH of the combined acidic extracts is raised to approximately 12 with aqueous sodium hydroxide (50%) with ice bath cooling and the basic mixture is extracted with chloroform (50-100 ml, 2 times). The combined chloroform extracts are dried over sodium sulfate, the solvent removed at reduced pressure and the crude product flash chromatographed on silica gel. In some cases the products were converted to acid addition salts.

The cycloalkyl amines (IV) are prepared by methods well known to those skilled in the art. It is preferred to start with a 3-alkoxy-cyclopent-2-en-1-one, 3-alkoxycyclohex-2-en-1-one or 3-alkoxycyclohept-2-en-1-one depending on whether $n_5$ is 1, 2 or 3. It is preferred that the alkoxy group be ethoxy. Grignard reaction with X—M-g—$(CH_2)_{n4}$—O—magnesium to the $\alpha,\beta$-unsaturated ketone followed by acid hydrolysis gives the desired 3-substituted cycloalkyl-2-en-1-one. The terminal hydroxyl group is then oxidized with an oxidizing agent such pyridinium dichromate to the corresponding aldehyde which is then contacted with the amine corresponding to the amino portion of the desired cycloalkyl amine (IV). It is preferred to contact the amine with the non-amine portion in the presence of sodium cyanoborohydride. When $n_4$ is 3 it is preferred to use X—M-g—$(CH_2)_2$—C*(H)—O—$(CH_2)_2$—O* [where the atoms marked with an asterisk (*) are bonded to each other resulting in the formation of a ring] as the Grignard reagent.

The non-amine portions of the aromatic bicyclic amines (V) are known to those skilled in the art. See, in particular, U.S. Pat. Nos. 4,181,665 and 4,153,612. The aromatic bicyclic amines (V) of the present invention are made by the same method as the amines of U.S. Pat. Nos. 4,181,665 and 4,153,612.

The hydroquinones (VI) and quinones (VII) are readily interchangable as is well known to those skilled in the art. It is realized that with the hydroquinones (VI) when $R_{27}$ and $R_{28}$ are other than —H, that these groups are lost in the conversion to the corresponding quinone (VII). A hydroquinone (VI) and its corresponding quinone (VII) are both useful in the same manner and same way and therefore when the term hydroquinone (VI) is used it means and includes the corresponding quinone (VII) for purposes of this patent.

The hydroquinones (VI) are prepared by reaction of the aldehyde group of the non-amine portion of the hydroquinone starting material with the desired amine. The reaction is performed in the presence of an agent such as sodium cyanoborohydride in a polar solvent such as methanol or acetonitrile at about 20°-25°, preferred is methanol. Several of the non-amine starting materials are known, see for example, Hel. Chem. Acta 46, 650 (1963) and Chem. Pharm. Bull. 30, 2797 (1982). Starting materials with the desired chain length are synthesized by known chemical reactions. The free hydroquinone or hydroxyprotected non-amine portion of the hydroquinone (VI) can be used. In the later case, the hydroxy-protecting groups, usually esters such as acetate or ethers such as t-butyldimethylsilyl, are removed by means well known to those skilled in the art, for example, hydroxide/water/acetone followed by acidification or tetra-N-butyl ammonium chloride. The hydroquinones (VI) can readily be transformed into the corresponding quinones (VII) by means known to those skilled in the art, for example ferric chloride/ethyl acetate. Alternatively, using means known to those skilled in the art, one can start with the non-amine portion of a quinone, see Chem. Pharm. Bull. 30, 2797 (1982), transform it to the corresponding hydroquinone, and react it with the appropriate amine to produce the desired hydroquinone (VI).

The amino ethers (VIII) are prepared by contacting the hydroxyl protected (or unprotected) aldehyde group of the non-amine portion of the amino water (VIII) with the desired amine in the presence of a reducing agent such as sodium cyanoborohydride in a polar solvent such as methanol. Alternatively the appropriate aldehyde and amine can be contacted in a non-polar solvent such as toluene at about 50°-116° and removing the solvent. The resultant imine can then be contacted with a reducing agent such as sodium borohydride in a polar solvent such as methanol. The non-amine portion of the amino ether (VII) starting materials are known to those skilled in the art, see for example, Hel. Chem. Acta 46, 650 (1963) and Chem. Pharm. Bull. 30, 2797 (1982). If present the hydroxy protecting groups can be removed at this time. The hydroquinone-amine intermediate is then reacted with an agent such as chloroacetylchloride in the presence of a base, such as pyridine or triethylamine at about 0°-30° in a solvent such as ether to provide the appropriate chloroacetamide. Final cyclization can be effected by treatment of the acetamide with base, such as potassium carbonate, in a polar solvent, such as acetone at about 0°-50°. If desired the cyclic amide can be reduced with a reducing agent such as lithium aluminum hydride in an aprotic solvent such as ether to the corresponding amine. The protected hydroquinones can be prepared by standard methods, see for example J. Am. Chem. Soc. 94, 6190 (1972) from known hydroquinone carboxaldehydes.

The amino ethers (IX) are of two types, ones with the nitrogen atom "up" (IXA) and with the nitrogen atom "down" (IXB). The amino ethers (IXB) are prepared by reacting the appropriate 4-aminoresorcinol with chloracetyl chloride (or an equivalent reagent) in the presence of a base, such as pyridine or triethylamine at 0°-30° in an aprotic solvent such as ether. The resorcinol starting materials are known to those skilled in the art or can readily be prepared from known compounds by known methods. Cyclization is effected by treatment with a base such as potassium or sodium carbonate in a polar solvent such as acetone. Alkylation of the sodium or potassium salt of the cyclic amide (hydroxy protected) with the appropriate reagent, $R_4$-leaving group where leaving group is —Br, Cl or —O—tosyl at about $-78°$ to about 25° in a solvent such as ether, provides the amide product. The amide can be reduced, if desired, by reaction with a reducing agent such as lithium aluminum hydride or borane at about 0°-50° to provide the cyclic amine. Alternatively, the cyclic amide can be reduced with lithium aluminum hydride or borane and the cyclic amine reacted with $R_4$-leaving group or with $R_4$—CHO in the presence of a base such as potassium carbonate or sodium cyanoborohydride respectively. The amino ethers (IXA) are prepared in a similar manner. The starting materials are known, see Synthesis 69 (1982) and Can. J. Chem. 44, 1874 (1966).

Prodrugs of the aromatic amines (I), bicyclic amines (III), hydroquinones (VI), amino ether amines (VIII) and bicyclic amino either amines (IX) are prepared in general by reacting the phenol or salt of the phenol with the appropriate prodrug substituent such as carboxylic acid, isocyanate, anhydride, etc. More specifically, for the prodrug —$PO_2$—$O^-$ the phenol is reacted with phosphorous oxychloride and this intermediate compound is then reacted with water. For —CO—$(CH_2)_{n-21}$—$R_{51}$ where $R_{51}$ is —N(alkyl)$_2$, and —CO—C*=CH—CH=C(—$NR_{52}$)—CH=CH* (where $R_{52}$ is —H or $C_1$-$C_3$ alkyl and where the atoms marked with an asterisk (*) are bonded to each other resulting in the formation of a ring), the prodrugs are prepared from the phenol and the carboxylic acid in the presence of 1,3-dicyclohexycarbodiimide in a polar aprotic solvent such as methylene chloride. When $R_{51}$ is —$NH_2$, the t-butyl carbamate of the prodrug is prepared as above, followed by cleavage of the carbamate by reaction with an acid such as hydrochloric acid in methanol or trifluoroc acetic acid about 0°-25°. The compounds with the prodrug of the formula —O—$CH_2$—O—CO—$(CH_2)_{n21}$—$NR_{51-1}R_{51-2}$ are prepared by reaction of the salt of the phenol with the appropriate chloromethyl ether in a solvent such as tetrahydrofuran. The chloromethyl ethers can be prepared by the procedure of J. Org. Chem. 48, 5280 (1983). Prodrugs of —CO—CH=CH—CO—$O^-$ or —CO—$(CH_2)_{n-21}$—$COO^-$ are prepared by reaction of the (sodium) salt of the phenol with the anhydride at about 0°-60°. Alternatively, the phenol may be coupled with the diacid utilizing 1,3-dicyclohexylcarbodiimide and the resulting acid exposed to a base such as sodium carbonate to form the desired salt. Other prodrugs are prepared by known procedures.

The aromatic amines (I), alkyl amines (II), bicyclic amines (III), cycloalkyl amines (IV), aromatic bicyclic amines (V), hydroquinone amines (VI), quinone amines (VII), amino ether amines (VIII) and bicyclic amino ether amines (IX) collectively are referred to as amines (X), of the present invention are reacted with acids to form amine salts by methods known to those skilled in the art and the resulting salts are more water solulbe and therefore preferable to use when an aqueous formulation is desired such as a solution for IV use. Generally the amines (X) possess one or more basic nitrogen atoms. Because of this they can be converted to an acid addition pharmaceutically acceptable salt. The pharmaceutically acceptable salt forms of the amines (X) are generally preferred over the free base form since the salts have greater water solubility and form crystals more suitable for pharmaceutical purposes. An acid addition salt of the amines (X) can be converted to the free base, which can be converted to any desired pharmaceutically acceptable acid addition salt by methods known to those skilled in the art. It is preferred that the acid addition salt be prepared by reacting the free base of the amines (X) with an approximately stoichiometric amount of an acid, such as hydrochloric, hydrobromic, hydroiodic, sulfuric, phosphoric, acetic, lactic, citric, succinic, benzoic, salicyclic, pamoic, cyclohexanesulfamic, methanesulfonic, naphthalenesulfonic, p-toluenesulfonic, maleic, fumaric, oxalic acid and the like. It is preferred that the acid be selected from the group consisting of hydrochloric, maleic, methanesulfonic and fumaric acids.

The amines (X) and acid addition salts thereof can be isolated as hydrates or solvates, and such forms are regared as equivalent to the corresponding amines (X) not containing water or solvent.

It is preferred that the amine (X) be an aromatic amine (I), alkyl amine (II) or bicyclic amine (III). It is more preferred that the amine (X) be an alkyl amine (II) or bicyclic amine (III); most preferably bicyclic amine (III). It is preferred that the amine portion be a 1-piperazine substituted in the 4- position with $-(CH_2)_j$-heteroaryl where j is preferrably 0 and heteroaryl is preferrably (a) pyrimidin-4-yl substituted in the 2- and-/or 6-position with 4-morpholinyl, 1-pyrollidinyl or (b) pyridinyl substituted in the 3-position with $-NR_{M-3}R_{M-3}$. It is more preferred that the amine be A-22 (PREPARATION A-22) or A-47 (PREPARATION A-47). It is preferred that the amine (X) is 2-[[4-(2,6-bis-(1-pyrrolidinyl)-4-pyrimidinyl)-1-piperazinyl]methyl]-3,4-dihydro-2,5,7,8-tetramethyl-2H-1-benzopyran-6-ol (EXAMPLE 21) or 2-[[4-[3-(ethylamino)-2-pyridinyl]-1-piperazinyl]methyl]-3,4-dihydro-2,5,7,8-tetramethyl-benzopyran-6-ol (EXAMPLE 22); more preferred is 2-[[4-(2,6-bis-(1-pyrrolidinyl)-4-pyrimidinyl)-1-piperazinyl]methyl]-3,4-dihydro-2,5,7,8-tetramethyl-2H-1-benzopyran-6-ol.

With the aromatic amines (I), it is preferred that $X_1$ be $-O-$, $-CH_2-$ or $-CO-$. It is preferred that $n_1$ be 0-6, it is more preferred that $n_1$ be 1-6. It is preferred that $R_3$ be $-OH$ or $C_1-C_3$ alkoxy. It is preferred that $R_8$ and $R_9$ be $-H$. It is preferred that $R_{22}$ and $R_{23}$ are $-H$. It is preferred that $R_1$ and $R_2$ are the same and are $-H$, $-CH_3$ or t-butyl.

With the alkyl amines (II) it is preferred that $n_2$ is 4-8, more preferrably 6. It is preferred that $X_2$ be $-H$, $-OH$, $-O-CO-(C_1-C_4)$ or $-O-CO-$aryl.

For the bicyclic amines (III) it is preferred that $R_{16-1}$ or $R_{16-2}$ is $-CH_3$. It is preferred that $R_7$ is $-H$. It is also preferred that $R_{10}$, $R_{11}$ and $R_{12}$ are all $-CH_3$. It is preferred that $n_6$ is 1. It is preferred that $X_3$ is $-CO-$ or $-CH_2-$ and that $W_2$ is $-O-$.

For the cycloalkyl amines (IV) it is preferred that $n_4$ is 3-6 and $n_5$ is 2.

With the aromatic bicyclic amines (V) it is preferred that $R_{17}$ is $-(CH_2)_{n9}-W_1$.

The amines (X) of the present invention are useful pharmaceutical agents in treating a number of different medical conditions in humans and useful warm blooded animals. The 3,4-dihydrobenzopyran compounds (XI) are known, see EP 202,580-A. These compounds are used in the same way for the same purposes as the amines (X) of the present invention.

In humans, the amines (X) of the present invention are useful in treating spinal trauma, mild and/or moderate to severe head injury, subarachnoid hemorrhage and subsequent cerebral vasospasm, ischemic (thromboembolic) stroke, global ischemia, resuscitation (CPR), excess mucous secretion, asthma, muscular dystrophy, adriamycin-induced cardiac toxicity, brain tumor (neuroprotective), Parkinsonism, Alzheimer's disease, Bells Palsy, other degenerative neurological disorders, multiple sclerosis, organ damage during reperfusion after transplant, skin graft rejection, hepatic necrosis (e.g. from viral hepatitis, hemorrhagic, traumatic and septic shock, and conditions such as severe burns, ARDS, inflammatory diseases such as osteo- or rheumatoid arthritis, nephrotic syndrome (immunological), systemic lupus erythematosis, allergic reactions, atherosclerosis, inflammation (for example dermatological, inflammatory and psoriasis conditions), emphysema, stress induced ulcers, migrane cluster headaches, complications from brain tumors, some forms of radiation damage (for example during reaiation treatment or from accidental exposure to radiation), damage after MI, pre-birth infant strangulation and infant hypoxia syndrome, such opthalmic disorders as uveitis and optic neuritis, malignant hyperthermia and ischemic bowel syndrome.

In humans, the amines (X) are useful in preventing damage following cardiopulmonary resuscitation, neurological or cardiovascular surgery and from cardiac infarction, occular damage after opthalmic surgery (e.g. catratic surgery).

The aromatic amines (I) are also useful in treating AIDS (active against the HIV virus).

Generally, the amines (X) are used like the glucocorticoid pharmaceuticals for the treatment of the above human conditions as well as the animal conditions listed below. While the amines (X) are useful in both humans and animals in treating many of the same conditions and preventing damage from the same problems as the glucocorticoids, the amines (X) are useful in treating a number of conditions and preventing damage from conditions where the glucocorticoids are not useful. The amines (X) have no gulcocorticoid activity and therefore, unlike the glucocorticoids, they can be given daily for long periods of time (used chronically) without the side effects associated with the glucocorticoids. This is a distinct advantage.

It is to be understood that each of the amines (X) is useful to a different degree for treating each of the conditions above. However, as is known to those skilled in the art, some of the amines (X) are better for treating some conditions and others are better for treating other conditions. In order to determine which compounds are better than others for a particular condition one can utilize known tests that do not require expermentation but only routine analysis.

For example, the fertile egg or chich embryo assay of Folkman, Nature 288, 551 (1980) or Science 221, 719 (1983), discloses an assay to determine antiangiogenic activity which is indicative of inhibition of tumor growth and anti-cancer utility. Because of the ability of the compounds which are active in the Folkman embryo test to inhibit tumor growth, they are useful in the treatment of various diseases and conditions, especially various forms of cancer. Accordingly, they are administered to animals and humans to prolong survival or reduce pain and/or discomfort secondary to tumor growth and the alike. Further, the arachidonic acid $LD_{50}$ test of Kohler, Thrombosis Res., 9, 67 (1976), identifies compounds which are antioxidants, which inhibit lipid peroxidation, and/or which inhibit the prostaglandin cascade and are useful in treating spinal trauma, mild and/or moderate to severe head injury, degenerative neurological disorders, etc. Another method useful for determining which particular compounds inhibit lipid peroxidation and which are therefore useful in treating spinal trauma, mild and/or moderate to severe head injury, degenerative neurological disorders, etc. is described by Pryor in Methods of Enzymology 105, 293 (1984). Further, the mouse head injury assay of Hall, J. Neurosurg., 62, 882 (1980) discloses an assay from which one skilled in the art can readily determine which particular amines (VI) are useful in the acute treatment of spinal trauma or mild and/or moderate to severe head injury. Additionally, the cat 48 hr. motor nerve degeneration model of Hall et al, Exp. Neurol., 79, 488 (1983) discloses a routine assay from which one skilled in the art can readily determine which particular amines (VI) are useful in treating chronic degenerative neurological disorders such as Parkinsonism, Alzheimer's disease etc. H. Johnson in Int. Arch. Allergy Appl. Immunol., 70, 169 (1983) has described the ascarias sensitized rhesus monkey assay for anti-asthma drugs.

The standard contitions for treatment are to give the amines (VI) orally or parenterally, e.g. IV (that is by injection, infusion or continuous drip) or IM, with a standard dose of about 0.05 to about 10 mg/kg/day IV or about 0.5 to about 50 mg/kg/day, one to four times daily by mouth.

For treating spinal trauma, mild and moderate to severe head injury, damage following cardiopulmonary resuscitation, cardiac infarction, organ damage during reperfusion after transplant, hemorrhagic, traumatic and septic shock, severe burns, ARDS, and nephrotic syndrome and preventing skin graft rejection, the standard conditions are used. Typical treatment will involve an initial loading dose, e.g. an IV dose of 0.01 mg to 2 mg/kg followed by maintenance dosing e.g. IV infusion for a day to a week depending on the particular condition of the patient and the particular compound used. This may be supplemented with IM or oral dosing for days, weeks or months to prevent delayed neuronal degeneration in neurological applications (e.g. spinal trauma, head injury).

In treating subarachnoid hemorrhage and subsequent cerebral vasospasm or ischemic (thromboembolic) stroke the standard conditions are used and patients at risk are pre-treated orally.

In treating excess mucous secretion and asthma, the amines (X) are administered orally, IV and by inhalation in the standard dose. In treating excess mucous secretions the oral dose of the amines (X) used is from about 0.5 to about 50 mg/kg/day. The frequency of administration is one through 4 times daily. The oral administration of the amines (X) to treat excess mucous secretions may go on for months or even years. The susceptible individuals can be pre-treated a few hours before an expected problem. The IV dose is about 0.05 to about 20 mg/kg/day. The aerosol formulation contains about 0.05 to about 1.0% of the amines (X) and is administered or used about four times daily as needed.

In treating muscular dystrophy, Parkensonism, Alzheimer's disease and other degenerative neurological disorders (amyotrophic lateral sclerosis; multiple sclerosis) amines (X) are administered orally using a dose of about 0.5 to about 50 mg/kg/day, administered or used one to four times a day. The treatment may go on for years.

In addition, utility in disorders or physiological phenomena dependent on angiogensis or neovascularization such as embryo implantation (antifertility), arthritis, and atherosclerosis is exhibited with the amines (X) with or without co-administered oral heparin or systemic heparin fragments, see Science 221, 719 (1983).

In treating adriamycin-induced cardiac toxicity, the amines (X) are administered orally or IV using a dose of about 0.05 to about 50 mg/kg/day, preferrably about 0.5 to about 10 mg/kg/day. The amines (X) are preferably given concomitantly with IV adriamycin or the individual is pre-treated with the amines (X).

For prophylaxis prior to and preventing damage after neurological or cardiovascular surgery the amines (X) are used according to the standard conditions. The patient can be pretreated with a single IV or IM dose just prior to surgery or orally before and after surgery.

In treating osteo- or rheumatoid arthritis and other inflammatory diseases, the amines (X) are given orally or IM in doses of about 0.5 to about 50 mg/kg/day, one to four times daily. Orally the drug will be given over a period of months or years alone or with other steriodal or nonsteroidal antiinflammatory agents. The initial dose with some severe rheumatoid patients may be given IV and followed with an IV drip for up to 24 hr or more. In addition, intra-arterial administration may be employed.

In treating drug allergic reactions, the amines (X) are given in a dose of about 0.5 to 50 mg/kd/day, administered one to four times daily orally and IV. Typical treatment would be an initial IV loading dose followed by oral dosing for a few days or more.

In treating atherosclerosis and emphysema, the amines (X) are given orally in a dose of about 0.5 to about 50 mg/kg/day, one to four times daily for months or years.

In treating dermatological inflammatory conditions including psoriasis, the amines (x) are given orally in a dose of about 0.5 to about 50 mg/kg/day, one to four times daily or applied topically as a cream, ointment or lotion or equivalent dosage form in a concentration of about 0.5 to about 5% as long as needed. In treating these conditions the amines (X) can be used with steroidal agents.

The amines (X) are useful in the prevention and treatment of stress ulcers and of gastric intolerance caused by drugs such as nonsteroidal anti-inflammatory compounds (NOSAC). Stress ulcers are ulcers that develop after exposure to severe conditions such as trauma, burns, sepsis, extensive surgery, acute illnesses, and the like. Patients in intensive care units are particularly prone to develop stress ulcers. Stress ulcers also include lesions that can lead to upper gastrointestinal bleeding; such bleeding is likely to be prevented by these compounds. NOSAC includes drugs such as ibuprofen, aspirin, indomethacin, naproxen, piroxicam and the like that are usually taken for analgesia, and that are often associated with gastrointestinal intolerance characterized by pain and lesions that may lead to bleeding. The amines (X) will be administered preferentially by the oral route either as tablets, capsules or liquids, in doses ranging from about 5 to about 500 mg, two to four times a day. The treatment would be either preventive, i.e., starting before ulcers have formed in patients at risk of developing such lesions, or therapeutic, i.e., once the ulcers have formed. In patients whose cliinical condition precludes swallowing the oral dosage forms, the amines (X) would be given either through a nasogastric tube. or parenterally, i.e., IV or IM. The parenteral doses would range from about 1 to about 100 mg and be administered one to four times a day by IV.

In dogs, the amines (X) are useful in treating trauma, intervertebral diseases (slipped disk), traumatic shock, flea bite and other allergies.

In horses, the amines (X) are useful in treating endotoxic or septic shock which follows colic, pretreatment before surgery for colic and treatment of Founder (laminitis).

In cattle, the amines (X) are useful in treating acute coliform mastitis, bovine mastitis, acute allergic reaction to feed lot vaccination and shipping fever.

In pigs, the amines (X) are useful in treating porcine stress syndrome and thermal stress syndrome.

The term treatment or treating as used in this patent is used broadly and includes both treatment of an existing condition as well as preventing the same condition from occurring where such is possible as is well known to those skilled in the art. For example, the amines (X) can be used to treat existing asthma conditions and to prevent future ones from occurring. For example, the amines (X) treat spinal trauma and prevent rejection of skin grafts.

The amines (X) can be used with other pharmaceutical agents in treatment of the conditions listed above as is known to those skilled in the art.

The exact dosage and frequency of administration depends on the particular amines (X) used, the particular condition being treated, the severity of the condition being treated, the age, weight, general physical condition of the particular patient, other medication the individual may be taking as is well known to those skilled in the art and can be more accurately determined by measuring the blood level or concentration of the amines (X) in the patient's blood and/or the patients response to the particular condition being treated.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3-C(=Z_1)H$. Groups $R_i$ and $R_j$ would represent monovalent variable substituents if attached to the formula $CH_3-CH_2-C(R_i)(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3-O-CH_2-CH(R_i)-CH_3$ represents a 2-substituted-1-methoxypropane compound. In a similar fashion, the symbol "=" represents a double bond, e.g., $CH_2=C(R_i)-O-CH_3$, and the symbol "≡" represents a triple bond, e.g., $HC≡C-CH(R_1)-CH_2-CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by $N^*=C(CH_3)-CH=CCl-CH=C^*H$ with the convention that the atoms marked with an asterisk (*) are bonded to each other resulting in the formation of a ring. Likewise, the cyclic molecular fragment, 4-(ethyl)-1-piperazinyl can be represented by $-N^*-(CH_2)_2-N(C_2H_5)-CH_2-C^*H_2$.

A cyclic (ring) structure for any compound herein defines an orientation with respect to the plane of the ring for substituents attached to each carbon atom of the cyclic compound. In formulas depicting such compounds, a substituent attached to a carbon atom below the plane of the ring is identified as being in the alpha ($\alpha$) configuration and is indicated by a broken, dashed or dotted line attachment to the carbon atom, i.e., by the symbol "- - -" or ". . .". The corresponding substituent attached above the plane of the ring is identified as being in the beta ($\beta$) configuration. When a variable substituent is bivalent, the valences may be taken together or separately or both in the definition of the variable. For example, a variable $R_i$ attached to a carbon atom as $-C(=R_i)-$ might be bivalent and be defined as oxo or keto (thus forming a carbonyl group (—CO—) or as two separately attached monovalent variable substituents $\alpha-R_{i-j}$ and $\beta-R_{i-k}$. When a bivalent variable, $R_i$, is defined to consist of two monovalent variable substituents, the convention used to define the bivalent variable is of the form "$\alpha-R_{i-j}:\beta-R_{i-k}$" or some variant thereof. In such a case both $\alpha-R_{i-j}$ and $\beta-R_{i-k}$ are attached to the carbon atom to yield $-C(\alpha-R_{i-j})(\beta-R_{i-k})-$. For example, when the bivalent variable $R_6$, $-C(=R_6)-$ is defined to consist of two monovalent variable substituents, two monovalent variable substituents are $\alpha-R_{6-1}:\beta-R_{6-2}$, . . . $\alpha-R_{6-9}:\beta-R_{6-10}$, etc. yielding $-C(\alpha-R_{6-1})(\beta-R_{6-2})-$, . . . $-C(\alpha-R_{6-9})(\beta-R_{6-10})-$, etc. Likewise, for the bivalent variable $R_{11}$, $-C(=R_{11})-$, two monovalent variable substituents are $\alpha-R_{11-1}:\beta-R_{11-2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the α and β designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form —$CH_2$—$CH_2$—O—CO—. . ." means a lactone in which the carbonyl is bonded to $C_2$. However, when designated ". . . $R_j$ and $R_i$ are taken together to form —$CH_2$—$CH_2$—O—CO— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—$(CH_2)_n$—0—CO— where n is zero, one or 2. By the second method the carbon atom content of only each portion of the definition is indicated separately by enclosing the "Ci-Cj" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.
TLC refers to thin-layer chromatography.
THF refers to tetrahydrofuran.
TEA refers to triethylamine.
DMF refers to dimethylformamide.
Saline refers to an aqueous saturated sodium chloride solution.
IR refers to infrared spectroscopy.
NMR refers to nuclear (proton) magnetic resonance spectroscopy, chemical shifts are reported in ppm (δ) downfield from tetramethylsilane.

φ refers to phenyl ($C_6H_5$).

Ar refers to φ with the appropriate variable substituents as defined in the claims for the aromatic amines (I).

MS refers to mass spectrometry expressed as m/e or mass/charge unit. $M^+$ refers to the positive ion of a parent. $[M+H]^+$ refers to the positive ion of a parent plus a hydrogen atom. EI refers to electron impact. CI refers to chemical ionization. FAB refers to fast atom bombardment. HR refers to high resolution.

Ether refers to diethyl ether.

When solvent pairs are used, the ratios of solvents used are volume/volume (v/v).

PCT 86/01797 refers to published PCT patent application No. U.S. 86/01797, International Publication No. WO87/01706.

Suleptanate ester refers to the (sulfonylethyl-N-methylamido)-suberic acid (ester) R—O—CO—$(CH_2)_6$—CO—N($CH_3$)—$CH_2CH_2$—$SO_2$—$O^H$.

The term "amines (X)" refers to all the amines of the nine different types, the aromatic amines (I), the alkyl amines (II), the bicyclic amines (III), the cycloalkyl amines (IV), the aromatic bicyclic amines (V), the hydroquinone amines (VI), the quinone amines (VII), the amino ether amines (VIII) and the bicyclic amino ether amines (IX), see CHART A.

Pharmaceutically acceptable refers to those properties and/or substances which are acceptable to the patient from a pharmacological/toxicological point of view including bioavailability and patient acceptance or to the manufacturing chemist from a physical-chemical point of view regarding composition, formulation, stability and isolatability.

NNNNNN-NN-N refers to Chemical Abstracts Service (CAS, Columbus, Ohio) registry numbers where each "N" is an integer from 0 thru 9, but deleting leading zeros in the 6-digit portion of the number. Registry numbers are assigned to a particular chemical compound by CAS criteria, that the compound has been found to exist and it has been characterized in some way. Compounds published from approximately 1967 to the present are registered publicly and the registry number is the key to finding references in the CAS data base for such a registered compound. The CAS data base is publicly available from several database vendors such as STN International, System Development Corporation (SDC) Orbit Search Service, Lockheed Dialog, Bibliographic Retrieval Systems, Questrel, etc. CAS registry numbers are included in the EXAMPLES for some of the compounds which have been registered.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION A-1

Methyl[2-(methyl-2-pyridinylamino)ethyl]amine

A mixture of N,N'-dimethylethylene-diamine (25 g) and 2-chloropyridine (1.3 g) is warmed at 85° with stirring for 18 h. The excess dimethylethylenediamine is removed by distillation at reduced pressure. The distillation residue is distributed between ethyl acetate (150 ml) and water (100 ml). The organic phase is separated, dried over sodium sulfate and the organic solvent removed under reduced pressure to give the title compound.

PREPARATION A-2

2-Carboxy-1-piperidine

[535-75-1], see Aldrich item P4, 585-0.

PREPARATION A-3

4-(2-Furonylcarbonyl)piperazine

See Example 6B.

PREPARATION A-6

4-(2-Pyridinyl)piperazine

[34803-66-2], see French Patent 7253 M.

PREPARATION A-7

4-(2-Pyridinylmethyl)piperazine

[55579-01-6], see European Patent application 49,683.

PREPARATION A-8

4-(6-Methoxy-2-pyridinyl)piperazine

[51047-54-2], see Canadian Patent 979,894.

PREPARATION A-9

4-[(3-Hydroxy-2-pyridinyl)methyl]piperazine

A mixture of t-butyloxycarbonylpiperazine (2.3 g), 3-hydroxypyridine (0.98 g), formaldehyde (37%, 2.0 ml) and absolute ethanol (25 ml) are heated at 78° for 44 hr. The ethanol is removed under reduced pressure and the residue distributed between chloroform (150 ml) and sodium carbonate (0.1N, 100 ml). The aqueous phase is extracted with chloroform (100 ml). The organic phases are combined and washed with saline, dried over sodium sulfate and concentrated to a solid. The solid is dissolved in chloroform and chromatographed on a flash column using silica gel (150 g) eluting with ethyl acetate/methanol/ammonium hydroxide (9.9/0.8/0.2). The appropriate fractions are pooled and concentrated to give 4-[(3-hydroxy-2-pyridinyl)methyl]-1-piperazinecarboxylic acid t-butyloxy ester. This material is dissolved in methylene chloride (10 ml), cooled to 0° in an ice/water bath. Trifluoroacetic acid (10 ml) is added over 3 min. The mixture is stirred at 0° for 30 min and then allowed to warm to 20°-25° for 1 hr. The solvents are removed under reduced pressure and the residue is distributed between chloroform (100 ml) and saturated sodium bicarbonate (100 ml). The aqueous phase is extracted (2×) with chloroform (75 ml). The organic phases are combined, dried over sodium sulfate and concentrated to an oil. The aqueous bicarbonate phase is extracted with ethyl acetate for 48 hr. The ethyl acetate is removed under reduced pressure to leave an oil. These oils are combined to give the title compound, m.p. 254°; MS 193 (electron impact) m/e.

PREPARATION A-10

4-[6-(1-Pyrrolidinyl)-2-pyridinyl]piperazine

A solution of 2,6-dichloropyridine (10 g) and piperazine (25 g) in pyridine (30 ml) is stirred at 65° for 3 h and at 20°-25° overnight. The reaction mixture is concentrated, the residue is partitioned between ether and aqueous potassium carbonate. The organic phase is separated, washed with saline, dried over sodium sulfate and concentrated. The residue is added to pyrrolidine (15 g), pyridine (100 ml) and heated at 100° for 6 days. The reaction mixture is concentrated. The residue is partitioned between methylene chloride and aqueous sodium bicarbonate. The organic phase is separated, dried and concentrated. The residue is chromatographed on silica gel, eluting with methanol/ammonium hydroxide/methylene chloride (15/1/84). The appropriate fractions are pooled and concentrated to give the title compound, NMR (CDCl$_3$) 1.9, 2.9, 3.4, 5.75, 6.5, 7.3 δ.

PREPARATION A-11

4-[3-Amino-6-(diethylamino)-2-pyridinyl]piperazine

Diethylamine (3.29 ml) is added dropwise over 1 hr to a mixture of 2,6-dichloro-3-nitropyridine (6.13 g), acetonitrile (100 ml) and potassium carbonate (5.2 g) precooled to 0°. The resulting mixture is allowed to slowly warm to 20°-25° and is stirred for 16 hr. The mixture is filtered, the filtrate combined with piperazine (12.2 g) and potassium carbonate (6.0 g). The resulting mixture is heated at reflux for 24 hr and allowed to cool to 20°-25°. Aqueous workup (methylene chloride, water wash of organic layers and potassium carbonate) and purification by flash chromatography over silica gel eluting with methylene chloride/methanol (20/1 to 5/1), pooling and concentration of the appropriate fractions gives 6-N,N-diethylamino-3-nitro-2-(1-piperazinyl)piperidine.

A mixture of 6-N,N-diethylamino-3-nitro-2-(1-piperazinyl)piperidine (21.8 g), ethanol (275 ml), hydrochloric acid (1.2N, 27 ml) and palladium on charcoal (10%, 5.25 g) is exposed to hydrogen at 50 psi in a Parr flask. After 16 h the residue is filtered through celite, concentrated and partitioned between chloroform and 5% sodium hydroxide. The organic phase is separated, dried over potassium carbonate, concentrated and the residue passed through a plug of silica gel eluting with chloroform/methanol/ammonium hydroxide (4/1/0.25). The appropriate fractions are pooled and concentrated to give the title compound, IR (nujol) 3309, 2967, 2828, 1581, 1474, 1451, 1258 and 803 cm$^{-1}$; NMR (CDCl$_3$) 1.05, 2.9–3.1, 3.2, 3.2–3.4, 6.25 and 6.94 δ; MS (electron impact) 2.49, 2.20, 207, 193, 177 and 163.

PREPARATION A-13

4-[6-(Diethylamino)-3-(dimethylamino)-2-pyridinyl]piperazine

Sodium cyanoborohydride (0.5 g) is added to a mixture of 3-amino-6-N,N-diethylamino-2-((4-t-butylcarbamate)piperazin-1-yl)-piperidine (1.1 g), formalyn (37%, 11 ml) and acetonitrile (33 ml). The mixture is stirred for 24 h at 20°-25°, basic workup (chloroform, sodium carbonate, sodium sulfate) and flash chromatography over silica gel eluting with hexane/ethyl acetate (4/1) provides the protected form of the title compound. The protected amine (967 ml), ethyl acetate (20 ml) and hydrochloric acid (3.0N, 50 ml) are stirred for 3 h at 20°–25°. Basic workup (chloroform, 10% sodium hydroxide, sodium carbonate) gives the title compound, IR (nujol) 3289, 2935, 2820, 1589, 1566, 1479, 1445, 1429, 1373, 1263, 1236 and 940 cm$^{-1}$; NMR (CDCl$_3$) 2.9–3.1, 3.3–3.5, 3.51, 6.06 and 7.10 δ.

PREPARATION A-14

4-[4,6-Bis(2-propenylamino)-1,3,5-triazin-2-yl]-piperazine

A solution of 2-chloro-4,6-bis(2-propenylamino)-1,3,5-triazine (10.44 g) and 15.95 g of piperazine in 150 ml of DMF is heated under reflux for about 18 hours. The reaction mixture is cooled and stored at 5° and crystals are deposited. The soluble fraction is concentrated and the residue is extracted with ethyl acetate. The extracts are washed with aqueous potassium carbonate, and then 50% saline and dried over magnesium sulfate and concentrated to give a gum. Chromatography on silica gel (400 g) and elution (200 ml fractions) with 20% acetone-methylene chloride gives the formamide. The formamide (9.2 g) in 200 ml of methanol is heated to reflux, then cooled under nitrogen and mixed with 4 ml of 45% potassium hydroxide solution. The mixture is heated under reflux for about 20 hours, then cooled and concentrated. The residue is partitioned between ethyl acetate and water. The organic extracts are washed with water and saline, dried over magnesium sulfate and concentrated to give a gum. Crystallization from 50 ml of carbon tetrachloride gives the title compound, mp 93°–94.5°.

PREPARATION A-15

4-[2,6-Bis(diethylamino)-4-pyrimidinyl]piperazine

See Internation Publication No. 87/01706.

PREPARATION A-16

4-[6-Amino-4-(diethylamino)-2-pyrimidinylpiperazine

Dry piperazine (3.59 g) and 2-amino-4-diethylamino-6-chloropyrimidine (1.55 g) are heated at 100° in ethylene glycol (20 ml) for 4 h. The mixture is partitioned between methylene chloride and aqueous sodium bicarbonate. The phases are separated, the organic phase is dried with sodium sulfate and concentrated. The residue is chromatographed on silica gel eluting with ethyl acetate to 1% methanol/ethyl acetate to 20% methanol/1% ammonia/ethyl acetate. The appropriate fractions are pooled and concentrated to give the title compound, TLC (ethyl acetate/0.5% ammonium hydroxide) R$_f$=0.7.

PREPARATION A-17

4-[2,6-Bis(dimethylamino)-4-pyrimidinyl]piperazine

A mixture of dimethylamine (16.6 g, 25% in water), triethylamine (20 g) and 1,3,5-trichloropyrimidine (8.3 g) in ethanol (100 ml) is stirred at 20°–25° for 2 h. The mixture is stored at 0° overnight. Additional dimethylamine solution (2 g) is added and the reaction is stirred at 20°–25° for 2 h. The mixture is partitioned between methylene chloride and aqueous sodium bicarbonate. The organic phase is dried over sodium sulfate and concentrated. The residue is chromatographed over silica gel eluting with 10% ethyl acetate/hexane to give pure 2,4-bis[dimethylamino]-6-chloropyrimidine. This bis-adduct is heated with piperazine (2.6 g) in ethanol (100 ml) for 1 h. The mixture is partitioned between methylene chloride and aqueous sodium bicarbonate. The phases are separated, the organic phase is dried over sodium sulfate and concentrated. The residue is crystallized from ether and hexane to give the title compound, NMR (CDCl$_3$) 2.05, 3.0, 3.75 and 5.7 δ.

PREPARATION A-18

4-[2-(Diethylamino)-6-(1-pyrrolidinyl)-pyrimidinyl]piperazine

A solution of 2-diethylamino-4-piperazino-6-chloropyrimidine (4.10 g) in pyrrolidine (4.10 g) is heated at 100° for 12 h. The mixture is concentrated and the residue is partitioned between aqueous sodium bicarbonate and methylene chloride. The phases are separated and the organic phase is dried and concentrated to give the title compound, NMR (CDCl$_3$) 1.15, 1.90, 2.90, 3.45, 3.70 and 4.75 δ.

PREPARATION A-19

4-[2,6-Bis(4-methyl-1-piperazinyl)-4-pyrimidinyl]piperazine

Trichloropyrimidine is added in portions to an ice cool solution of N-methylpiperazine (40 g) in ethanol (200 ml). The mixture is then heated at 60° for 2 h. The mixture is concentrated and chromatographed on silica gel with 2–5% methanol and methylene chloride to give 2,4-bis[4-methylpiperazino]-6-chloropyrimidine. This material is heated at 130° in water (30 ml) with piperazine (32 g) in a Parr bomb for 20 h. The product is partitioned between methylene chloride and aqueous sodium carbonate. The phases are separated and the organic phase is dried over sodium sulfate and concentrated to give the title compound, TLC (methylene chloride/methanol/ammonium hydroxide-91.5/8/0.5) R$_f$=0.3.

PREPARATION A-20

4-[2-(Diethylamino)-6-(4-methyl-1-piperazinyl)-4-pyrimidinyl]piperazine

2-Diethylamino-4,6-dichloropyrimidine (10 g) is reacted with piperazine (14.45 g) in ethanol (200 ml) at reflux for 2 hr. The mixture is concentrated and the product isolated by silica gel chromatography giving 2-diethylamino-4-piperazino-6-chloropyrimidine. The 2-diethylamino-4-piperazino-6-chloropyrimidine (8 g) and N-methylpiperazine (8 g) is heated neat at 70° for 16 hr. Then water (2.5 ml) is added and the mixture is heated at 100° for 50 hr. The mixture is chromatographed on silica gel, the appropriate fractions are pooled and concentrated to give the title compound, NMR (CDCl$_3$) 1.15, 2.80, 2.85, 2.90, 3.30, 3.70 and 4.95 δ.

PREPARATION A-21

4-[2-(Diethylamino)-6-(1-piperidinyl)-4-pyrimidinyl]-piperazine

A solution of 2-diethylamino-4,6-dichloropyrimidine (4 g) in piperidine (6 g) is heated at 80° for 20 min. The mixture is stirred at 20°–25° for 15 h and then partitioned between methylene chloride and aqueous sodium carbonate. The phases are separated, the organic phase is dried over sodium sulfate and concentrated. The residue and piperazine (8 g) are refluxed in pyridine (100 ml) for 6 h. The reaction is partitioned between methylene chloride and aqueous potassium carbonate. The organic phase is dried over sodium sulfate, concentrated to a residue which is chromatographed on silica gel eluting with methylene chloride to 6% methanol/1% ammonium hydroxide/methylene chloride. The appropriate fractions are pooled and concentrated to give the title compound, NMR (CDCl$_3$) 1.15, 1.53, 2.90, 3.45 and 4.95 δ.

PREPARATION A-22

4-[2,6-Bis(1-pyrrolidinyl)-4-pyrimidinyl]piperazine

A solution of pyrrolidine (80 g) in THF (500 ml) is chilled in an ice water bath and stirred mechanically under nitrogen. With a syringe pump of 2,4,6-trichloropyrimidine (50 g) is added over 35 minutes. The reaction is stirred in the ice bath for 1 hour and is then warmed to 20°-25° over 4 h. Pyridine (100 ml) is added to the reaction and the mixture stirred at 20°-25° overnight. The reaction is concentrated. The residue is partitioned between methylene chloride and aqueous sodium bicarbonate. The organic phase is concentrated and the residue chromatographed on silica gel (10% ethyl acetate/hexane) to yield 51 g of crystalline 2,4-bis[pyrrolidino]-6-chloropyrimidine. Immediately after the initial addition of reagents, two spots are seen with 25% ethyl acetate on a silica gel plate. These are th 2- and the 4-adducts. The bis product forms over time. It moves between these first two spots. The 51 g of product is reacted with piperazine (40 g) in 100 ml of dry pyridine at 100° for 50 h. The reaction is concentrated. The residue is partitioned between methylene chloride and sodium bicarbonate solution. The organic phase is dried and concentrated. The residue is chromatographed on silica gel eluting with methylene chloride to 10% methanol/1% ammonia/methylene chloride to give the title compound, NMR (CDCl$_3$) 1,90, 2.9, 3.35 and 4.80 δ.

PREPARATION A-23

4-[2,6-Bis(morpholino)-4-pyrimidinyl]piperazine

A solution of 160 g of morpholine in 1000 ml of methylene chloride is treated dropwise with 100 g of 2,4,6-trichloropyrimidine. The reaction is immersed in an ice water bath. After 1 h, 300 ml of pyridine is added. The reaction is stirred for two days and concentrated. The residue is partitioned between methylene chloride and aqueous sodium bicarbonate. The residue is chromatographed on silica gel (10% ethyl acetate/hexane to 25% to methylene chloride) to give 2,4-[bis(morpholino)]-6-chloropyrimidine. A solution of 40 g of 2,4-[bis-morpholino]-6-chloropyrimidine and 34 g of piperazine in 60 g of pyridine is heated at 100° for 24 h. The mixture is partitioned between methylene chloride and aqueous potassium carbonate. The organic phase is filtered through sodium sulfate and concentrated. The residue is chromatographed (methylene chloride to 4% methanol/1% ammonium hydroxide/methylene chloride) to give the title compound, NMR (CDCl$_3$) 2.90, 3.50, 3.75, 3.80 and 5.10 δ.

PREPARATION A-24

4-[2,6-Bis(allylamino)-4-pyrimidinyl]piperazine

Following the general procedure for PREPARATION A-22, and making non-critical variation but substituting allylamine for pyrrolidine the title compound is obtained.

PREPARATION A-25

4-(2-Pyrimidinyl)piperazine [20980-22-7]

See U.S. Pat. No. 4,409,223.

PREPARATION A-26

4-[4,6-Bis(diethylamino)-2pyrimidinyl]piperazine

Diethylamine (80 g) is reacted with trichloropyrimidine (50 g) in THF. The reaction after chromatography yields a mixture of the mono- and di-adduct. This material is dissolved in pyridine (58 g) and reacted with diethylamine (35 g) at 50° for 3 h. The reaction is concentrated to a residue. The residue is partitioned between methylene chloride and aqueous sodium bicarbonate. The organic phase is separated and concentrated. The residue is chromatographed on silica gel, eluting with ethyl acetate/hexane (10/90). The appropriate fractions are pooled and concentrated to give 2,4-bis[diethylamino]-6-chloropyrimidine. This material is dissolved in pyridine (100 g) and reacted with piperazine (40 g) at 100° for 50 h. Following the above workup procedure the title compound is obtained, NMR (CDCl$_3$) 1.15, 2.90, 3.45 and 4.9 δ.

PREPARATION A-27

4-(3,6-Dimethylpyrazinyl)piperazine [59215-42-8]

See Canadian Patent 979,894.

PREPARATION A-28

4-[(5-Methyl)-4-phenyl-4H-1,2,4-triazol-3-yl]piperazine

A mixture of 3-bromo-5-methyl-4-phenyl-4H-1,2,4-triazole (4.16 g), 15.07 g of piperazine and 20 ml of pyridine is stirred at 100° under nitrogen for 22 h. The reaction is monitored by TLC (8% methanol/methylene chloride) and after this period of time no change occurs. The mixture is subsequently placed in a Parr bomb and heated in an oil bath at 180° for 24 h. Bomb pressure increases by 40 psi. The mixture is worked up by partitioning between chloroform and water. The organic phase is washed with saturated aqueous sodium bicarbonate (2×) and with saline (2×), dried over sodium sulfate and concentrated to a solid, the product is recrystallized in ethyl acetate, MS [M+H]+ 243.1484

PREPARATION A-29

4(Benzo[b]thien-2-yl)piperazine

2-Chlorobenzothiazole (5g) is heated in ethanol (75 ml) with piperazine (3.05 g) for 20 h. The mixture is partitioned between methylene chloride/ether and aqueous sodium bicarbonate. The organic phase is separated, dried with sodium sulfate and concentrated to give the title compound.

PREPARATION A-30

4-(2-Methoxyphenyl)piperazine

[35386-24-4], see Aldrich item M2,260-1.

PREPARATION A-31

4-(4-Methoxyphenyl)piperazine

[70849-64-8], see Aldrich item M2,300-4.

PREPARATION A-32

4-[(3,4-Dimethoxyphenyl)methyl]piperazine

See French Patent 7031 M.

PREPARATION A-33

4-(4-Fluorophenyl)piperazine

[2252-63-3], see Aldrich item 19,133-7.

PREPARATION A-34

4-[2-Amino-5-(1-pyrrolidinyl)phenyl]piperazine

Pyrrolidine (2.0 ml) is added to a mixture of 2,4-dichloronitrobenzene (4.50 g), acetonitrile (25 ml) and potassium carbonate 4.90 g). After stirring for 48 hr at 20°-25° basic workup gives 1-nitro-2-piperazinyl-4-pyrrolidinylbenzene.

A mixture of 1-nitro-2-piperazinyl-4-pyrrolidinylbenzene (4.57 g), ethanol (110 ml), hydrochloric acid (1.2N, 6 ml) and palladium on carbon (10%, 1 g) is exposed to hydrogen 51 psi at 20°-25° in a Parr flask. After 16 h (49 psi total uptake) the mixture is filtered. Basic workup (chloroform, potassium carbonate) and column chromatography silica gel (50 g) eluting with chloroform/methanol (4/1) gives the title compound as an oil, IR (nujol) 3315, 2947, 2816, 1512, 1258, 1001 and 753 cm$^{-1}$; NMR (CDCl$_3$) 1.8-2.0, 2.9-3.2, 6.52 and 6.6-6.8 δ; MS (electron impact) 246, 204 and 189.

PREPARATION A-35

4-[[4-(Dimethylamino)phenyl]methyl]piperazine

See U.S. Pat. No. 4,421,753.

PREPARATION A-36

4-Hydroxy-4-[4-(trifluoromethyl)phenyl]piperidine

[39757-71-6], see U.S. Pat. No. 3,936,464.

PREPARATION A-37

(2-Diethylaminoethyl)amine

[111-74-0], see Aldrich item 12,642-2.

PREPARATION A-38

[2-(3,4-Dimethoxyphenyl)ethyl]amine

[120-20-7], see Aldrich item D13,620-4.

PREPARATION A-39

[2-(2,4-Dimethoxyphenyl)-1-methylethyl]amine

See J. Pharm. Sci. 60, 1232 (1971).

PREPARATION A-40

[2-(3,4-Dimethoxyphenyl)ethyl][3,4,5-trimethoxyphenyl)-methyl]amine

A mixture of 3,4-dimethoxyphenylamine (2.87 g), 3,4,5-trimethoxybenzaldehyde (3.15 g), benzene (100 ml) and p-TSA (276 ml) is heated at reflux in a Dean Stark apparatus. After 16 hours, the mixture is allowed to cool to 20°-25°. Basic workup (methylene chloride, sodium bicarbonate, magnesium sulfate) gives an imine. Sodium borohydride (1.2 g) is added in several portions over 2 hours to the imine in methanol (65 ml) and hydrochloric acid (1.2N, 7.4 ml). After 3 hours, acidic workup (ether, chloroform, sodium carbonate) gives the title compound as an oil, IR (Nujol) 2939, 1591, 1516, 1463, 1420, 1236 and 1128 cm$^{-1}$; NMR (CDCl$_3$) 2.7-3.0, 3.7-4.0 and 6.5-6.9 δ; MS (chemical ionization) [M+H]$^+$ 360, 199, 182, 181.

PREPARATION A-41

[2-(3,4-Dimethoxyphenyl)ethyl][[4-(dimethylamino)-phenyl]mehtyl]amine

[13159-97-2], see Chem. Abst. 65:7001f.

PREPARATION A-42

[(3,4-Dihydroxyphenyl)methyl][2-(3,4-dimethoxyphenyl)-ethyl]amine

A mixture of 3,4-dihydroxybenzaldehyde (1.25 g) t-butyldimethylsilyl chloride (3.5 g), dimethylformamide (10 ml) and imidazole (1.54 g) is stirred for 18 h at 20°-25°. The mixture is diluted with ether and washed successively with dilute hydrochloric acid and dilute sodium bicarbonate. The organic phase is separated and dried over magnesium sulfate and concentrated to give an oil homogeneous by TLC. The oil (3.3 g), 3,4-dimethoxyethylamine (1.77 g) toluene (50 ml) and p-TSA (150 ml) are heated at reflux in a Dean Stark apparatus for 24 h. Afterwards the solution is permitted to cool to 20°-25°, methanol (35 ml), hydrochloric acid (1.2N, 4.2 ml) and sodium borohydride (1 g) are added. After 2 h the mixture is concentrated, basic workup (chloroform, sodium carbonate, sodium sulfate) gives a compound which is purified by flash chromatography over silica gel diluting with chloroform/methanol (30/1). The appropriate fractions are pooled and concentrated to give the title compound as an oil, IR (nujol) 2931, 2858, 1511, 1297, 1259, 909, 840 and 782 cm$^{-1}$; NMR (CDCl$_3$) 0.19, 0.99, 2.7-2.9, 3.68, 3.87, and 6.6-6.9 δ; MS (chemical ionization) [M+H]$^+$ 532, 386, 351.

PREPARATION A-43

(2-Pyridinyl)methylamine

[3731-51-9], see Aldrich item A6,520-4.

PREPARATION A-44

4-[2-[4-[2,6-Bis(1-pyrrolidinyl)-4-pyrimidinyl]-1-piperazinyl]ethyl]piperazine

Several batches of di-t-butyl dicarbonate (17.7 g) is added to a stirred mixture of 2-hydroxyethylpiperazine (10.6 g) in ether (300 ml). The mixture is stirred at 20°-25° for 1.5 hr and then washed with sodium hydroxide (5%, 200 ml), saline (200 ml), dried over sodium sulfate, and filtered. The organic solvent is removed under reduced pressure to give an oil. The oil is flash chromatographed on silica gel (100 g), eluting with ethyl acetate/methanol/ammonium hydroxide (9.5/0.4/0.1). The appropriate fractions are pooled and concentrated to give the N-protected 2-hydroxyethylpiperazine.

The N-protected 2-hydroxyethylpiperazine (3.0 g), triethylamine (1.42 g) and methylene chloride (30 ml) is cooled to 0° in an ice bath under nitrogen. A mixture of methanesulfonyl chloride (1.64 g) in methylene chloride (30 ml) is added dropwise over 10 min. The cooling bath is removed and the mixture allowed to warm to 20°-25° for 30 min. The mixture is then washed with water (60 ml), dried over sodium sulfate and the solvent removed to give crude mesylate. 4-[2,6-Bis(1-pyrrolidinyl)-4-pyrimidinyl]piperazine (4.23 g), potassium carbonate (1.93 g) and acetonitrile (150 ml) are added to the crude mesylate. The mixture is heated at reflux for 18 hr. The acetonitrile is removed under reduced pressure and the residue distributed between chloroform (200 ml) and water (200 ml). The phases are separated, the organic phase is washed with saline, dried over sodium sulfate and the solvent removed under reduced pressure to give an oil. The oil is flash chromatographed on silica gel (200 g) with ethyl acetate/methanol/ammonium hydroxide (9.5/0.4/0.1). The appropriate fractions are pooled and concentrated to give the N-protected form of the title compound as a solid, mp 148°–149°.

This solid (0.75 g) in methylene chloride (10 ml) is stirred and cooled to 0° in an ice/water bath. Trifluoroacetic acid (10 ml) is added dropwise over 5 min. The cooling bath is removed and the mixture is stirred at 20°–25° for 1 hr. The organic solvent is removed under reduced pressure and the residue is distributed between methylene chloride (50 ml) and sodium hydroxide (10%, 50 ml). The organic phase is separated, and dried over sodium sulfate. The solvent is removed to give the title compound.

PREPARATION A-45

4-[4,6-Bis(1-pyrrolidinyl)-1,3,5-triazin-2-yl]-1-piperazine

Pyrrolidine (28.5 g) is cooled with an ice bath. 1,3,5-Trichlorotriazine (18.4 g) is added with vigorous stirring. After 1–1.5 h the mixture is permitted to warm to 20°–25°. The solid is filtered and rinsed several times with water and dried under reduced pressure to give the monochloro-bis(1-pyrrolininyl)triazine.

This material (23.18 g) in piperazine (31.55 g) and DMF (295 ml) is refluxed under nitrogen. When the reaction is complete (TLC) the solvent is removed under reduced pressure. The mixture is transferred to a separatory funnel containing ethyl acetate (100 ml) and potassium carbonate (100 ml). The layers are separated, the organic layer is washed with saline (100 ml) and back-washed with ethyl acetate (2×100 ml). The organic layers are combined, dried over magnesium sulfate at room temperature, filtered and concentrated under reduced pressure. This material is chromatographed on a silica gel column (500 g) eluting with acetone/methylene chloride (5/95). The appropriate fractions (500 ml) are pooled and concentrated to give a solid.

The solid (10.13 g) is refluxed in methanol (200 ml) and cooled under nitrogen. Potassium hydroxide (45% aqueous, 4 ml) is added, the mixture degassed with nitrogen and heated to reflux. After 8 h the mixture is cooled to room temperature and concentrated under reduced pressure. The solid is transferred to a separatory funnel containing ethyl acetate (200 ml) and water (100 ml). The phases are separated, the organic layer is washed with water (2×100 ml) and 50% brine (100 ml) followed by brine (2×100 ml). The aqueous washes are back-washed with 200 ml of ethyl acetate, the organic phases are combined, dried over magnesium sulfate, filtered, concentrated under reduced pressure to give the title compound, m.p. 162.5°–166°.

PREPARATION A-46

4-[5,6-Bis(diethylamino)-2-pyridinyl]piperazine

Diethylamine (3.29 ml) is added dropwise over 1 h to a mixture of 2,6-dichloro-3-nitropyridine (6.13 g), acetonitrile (100 ml) and potassium carbonate (5.2 g) precooled to 0°. The mixture is allowed slowly to warm to 20°–25° and is stirred for 16 h. The mixture is filtered, the filtrate combined with piperazine (12.2 g) and potassium carbonate (6 g). The resulting mixture is heated at reflux for 24 h and then permitted to cool to 20°–25°. Aqueous workup (methylene chloride, water washed over organic layers, potassium carbonate) and purification by flash chromatography (silica gel) eluting with chloroform/methanol (20:1→5:1) gives 2-N,N-diethylamino-3-nitro-6-(1-piperazinyl)pyridine.

This material (21.8 g), ethanol (275 ml), hydrochloric acid (1.2N, 27 ml) and 10% palladium on charcoal (5.25 g) is exposed to hydrogen at 50 pounds per square inch in a Parr flask. After 16 h the residue is filtered through celite, concentrated and partitioned between chloroform and sodium hydroxide (5%). The organic layers are separated, dried using potassium carbonate and concentrated. The concentrate is passed through a plug of silica gel, eluting with chloroform/methanol/ammonium hydroxide (4/1/0.25) to give 3-amino-2-N,N-diethylamino-6-(1-piperazinyl)pyridine.

A solution of di t-butyl dicarbonate (11.8 g) and methylene chloride (25 ml) is added dropwise over 30 min to a mixture of 3-amino-2-N,N-diethylamino-6-(1-piperazinyl)pyridine (13.5 g), triethylamine (8.33 ml) and methylene chloride (400 ml) precooled to 0°. The resulting mixture is allowed to slowly warm to 20°–25°. After 16 h using basic workup (methylene chloride, sodium bicarbonate, potassium carbonate) the t-butyl carbamate as a solid is obtained.

The protected piperazinyl pyridine (4 g), acetaldehyde (12.8 ml), acetonitrile (80 ml) is mixed. Sodium cyanoborohydride (1.73 g) is added to the pyridine mixture. The resultant solution is stirred for 48 h at 20°–25°. After 24 h additional sodium cyanoborohydride (0.5 g) and acetaldehyde (5 ml) are added. Basic workup (chloroform/potassium carbonate, potassium carbonate) and purification by flash chromatography using silica gel and eluting with hexane ethyl acetate (5/1) gives an oil. The oil (2.36 g), ethyl acetate (50 ml), and hydrochloric acid (3.0N, 37.5 ml) are stirred for 16 h at 20°–25°. Basic workup (chloroform, 10% sodium hydroxide, potassium carbonate) gives the title compound, MS (electron impact) 305.

PREPARATION A-47

4-[3-(Ethylamino)-2-pyridinyl]piperazine 2-(1-piperazinyl)-3-nitropyridine (24.50 g), ethanol (445 ml) and hydrochloric acid (1.2N, 44 ml) are combined and hydrogenated overnight at 40 psi in a Parr bomb, refilling when necessary. The mixture is filtered through celite, washed with ethanol, chloroform, ethanol and water. The organic solvents are removed with reduced pressure. The remaining material is partitioned between methylene chloride (3×250 ml) and sodium bicarbonate. The organic layers are combined, dried over potassium carbonate, filtered and concentrated under reduced pressure to give an oil which slowly solidified upon standing to give 3-amino-2-(1-piperazinyl)pyridine.

3-Amino-2-(1-piperazinyl)pyridine (19.58 g), methylene chloride 600 ml), triethylamine (17.2 ml) are combined and cooled to 0°. Di-t-butyl-dicarbonate (24.34 g) in methylene chloride (50 ml) is added to the pyridine mixture over 30 min and permitted to stand at 0° for 1 hr, then allowed to warm to 20°–25°. After 30 min, TLC indicates no starting material remains. The reaction mixture is partitioned between sodium bicarbonate (500 ml) and methylene chloride (3×250 ml). The organic phases are combined, dried over potassium carbonate, filtered and concentrated under reduced pressure and heat to give a solid which is recrystallized from ethyl acetate to give 3-amino-2-[(4-t-butyl carbamate)-1-piperazinyl]pyridine.

3-Amino-2-[(4-t-butyl carbamate)-1-piperazinyl[pyridine (2.361 g), methanol (23.6 ml) and acetaldehyde (2.1 ml) are combined at 20°-25° to form a solution. Sodium cyanoborohydride (586 mg) is added and the mixture stirred overnight. The organic solvent is removed with reduced pressure and heat, the remaining mixture is partitioned between sodium bicarbonate (50 ml) and chloroform (3×50 ml). The chloroform extracts are combined and dried over potassium carbonate and filtered. The filtrate is concentrated with heat and reduced pressure. The concentrate is column chromatographed on silica gel 60 (40 63μ) eluting with hexane/ethyl acetate (2/1) containing triethylamine (1%). The appropriate fractions are pooled and concentrated to give 3-ethylamino-2-[(4-t-butyl carbamate)-1-piperazinyl[piperidine.

3-Ethylamino-2-[(4-t-butyl carbamate)-1-piperazinyl]piperidine (2.47 g), ethyl acetate (67 ml) and hydrochloric acid (3N, 49 ml) are combined and stirred for 2 hr at 20°-25°. TLC indicates no starting material. Potassium hydroxide (14 g) and water (80 ml) is added. The organic layer is removed and extracted with chloroform (3 ×60 ml). The organic layers are combined, dried over potassium carbonate, filtered and the filtrate concentrated to give the title compound. NMR (CDCl$_3$) 1.25, 1.50, 3.1, 3.5, 6.90 and 7.75 δ.

PREPARATION A-48

4-[3-(Diethylamino)-2-pyridinyl]piperazine

Following the general procedure of PREPARATION A-47 and making non-critical variations but reacting the protected ethylamine compound with additional acetaldehyde and again reducing the title compound is obtained. NMR (CDCl$_3$) 0.95, 3.25, 6.80, 7.20 and 7.90 δ.

PREPARATION A-49

4-[4,6-Bis(2-pyridinyl)-1,3,5-triazin-2-yl]piperazine

A mixture of 4-formyl-piperazinecarboximidamide hydroiodide (prepared according to U.S. Pat. No. 4,351,832) in ethanol (4 ml) and ethanolic sodium ethoxide (1.4N, 6.8 ml) is stirred for 15 min, then 2-cyanopyridine (2.08 g) is added. The mixture is concentrated at atmospheric pressure and heated at about 200° for 5 hr, then cooled and chromatographed on silica gel eluting with methanol/methylene chloride (30/70). The appropriate fractions are pooled and concentrated to give the 1-formyl 4-[4,6-bis(2-pyridinyl)-1,3,5-triazin-2-yl]piperazine. Hydrolysis of the formamide in the usual way (PREPARATION A-14) gives the title compound.

PREPARATION A-50

4-[5,6-Bis(2-pyridinyl)-1,2,4-triazin-3-yl]piperazine

A mixture of 4-formyl-piperazinecarboximidamide hydroiodide (prepared according to U.S. Pat. No. 4,351,832) in ethanol (4 ml) and ethanolic sodium ethoxide (1.4N, 6.8 ml) is stirred for 15 min and then anhydrous hydrazine (0.32 g) in ethanol (3 ml) is added. The mixture is stirred an additional 15 min, then 2,2'-pyridil (2.12 g) is added. The mixture is stirred for 12 hours at 25° and concentrated. The residue is chromatographed on silica gel eluting with a methylene chloride/methanol mixture. The appropriate fractions are pooled and concentrated to give 1-formyl 4-[5,6-bis(2-pyridinyl)-1,2,4-triazin-3-yl]-piperazine. Hydrolysis of the formamide in the usual way (PREPARATION A-14) gives the title compound.

PREPARATION A-51

4-[2,6-Bis(2-pyridinyl)-4-pyrimidinyl]piperazine

4-Chloro-2,6-bis(2-pyridinyl)pyrimidine [prepared by the method of J.A.C.S. 32, 1591 (1967), 4.2 g] piperazine (13.44 g) and ethanol (70 ml) are heated at reflux for 2 hr. The mixture is allowed to cool and the solvent is removed under reduced pressure. The residue is dissolved in chloroform (250 ml), washed with water (twice), dried over sodium sulfate and concentrated under reduced pressure to give an oil. The oil is crystallized from ether to give the title compound, m.p. 159°-161°; MS (m/e) 318 (M+)

PREPARATION A-55

3,6-Bis(2-pyridinyl)-4-pyridazine

PREPARATION A-56

6-Methoxy-2-morpholino-4-(1-piperazinyl)pyrimidine

A solution of 2,4,6-trichloropyrimidine (55 g), methanol (50 ml) and collidine (50 g) is heated in dry tetrahydrofuran (400 ml) for 48 hr. Ether is added and the precipitate is collected. The precipitate is column chromatographed on silica gel to give 6methoxy-2,4-dichloropyrimidine. This product is mixed with morpholine in THF and stirred at 20°-25° to give 6-methoxy-2-morpholino-4-chloropyrimidine. The 6-methoxy-2-morpholino-4-chloropyrimidine is heated with piperazine in pyridine at 60° for 24 hr to give the title compound.

PREPARATION A-57

4-(3-Chlorophenyl)piperazine

[65369-76-8], see Aldrich catalog, 1986-7, 12,518-0.

PREPARATION A-58

4-[3-(Diethylamino)-2-pyridinyl]piperazine

Sodium cyanoborohydride (3.06 g) is added to a solution of 1-[2-(3-ethylamino)pyridinyl]-4-(t-butyl carbamate)piperazine (5.38 g), acetaldehyde (5.0 ml) and methanol (54 ml). The mixture is stirred for 10 days at 20°-25°. Acetaldehyde (5.0 ml) is added at 2, 3, 4 and 7 days. Sodium cyanoborohydride (3.06 g) is added at 3 and 7 days. After 10 days no further change in the reaction occurred as measured by TLC. Basic workup (chloroform/sodium bicarbonate/magnesium sulfate) gives an oil. The crude residue is resubmitted to the above reaction conditions. After 5 days the reaction is worked up as described above. Purification by flash chromatography (hexane/ethyl acetate; 5/1) provides the carbamate of the title compound, NMR (CDCl$_3$) 0.98, 1.49, 3.21, 3.35–3.65, 6.82, 7.16 and 7.92 δ; IR (neat) 2974, 1699, 1577, 1438, 1234 and 1172 cm$^{-1}$; MS (EI) m/e (relative percent) 334 (79), 205 (64), 178 (45), 162 (56), 57 (100).

The carbamate (1.17 g), ethyl acetate (29.0 ml) and hydrochloric acid (3N, 21.2 ml) are stirred at 20°-25° for 1.5 hr. Potassium hydroxide (8 g) and water (30 ml) are added. Aqueous workup (chloroform/potassium carbonate) gives the title compound. IR (nujol) 2957, 2925, 1574, 1450, 1249 and 776 cm$^{-1}$; NMR (CDCl$_3$) 0.96, 3.16, 3.15–3.3, 3.7–3.85, 6.84, 7.17 and 7.91 δ; MS (EI, relative percent) 234 (60), 178 (66), 162 (100) and 148 (67).

PREPARATION A-59

4-(5-Diethylamino-2-pyridinyl)piperazine

2-Chloro-5-nitropyridine (25 g) is dissolved in acetonitrile (150 ml) and the mixture is added dropwise over 30 min to a stirred suspension of piperizine (61.3 g) and potassium carbonate (26.2 g) in acetonitrile (550 ml). The reaction mixture is stirred at 20°-25° for 16 hr. The solvent is removed on a rotary evaporator and the residue is diluted with methylene chloride/water. The organic layer is separated and washed with water (twice) and saline, dried over potassium carbonate and concentrated to give 1-(5-nitro-2-pyridinyl)-piperazine, IR 3338, 3102, 3068, 1603, 1570, 1482, 1347, 1340, 1320, 1306 and 1253 cm$^{-1}$.

The nitro compound (30.7 g) is dissolved in ethanol (500 ml), and palladium/carbon (10%, 10 g) and hydrochloric acid (1.2N, 55 ml) are added and the mixture hydrogenated on a Parr apparatus (50 psi) for 4 hr. The mixture is then filtered thru celite and the filtrate evaporated to dryness to give an oil. The residue is partitioned between saturated sodium bicarbonate and chloroform, the layers are separated, the aqueous layer is reextracted with chloroform (2 × 250 ml) and the organic phases are combined, dried over potassium carbonate and concentrated under reduced pressure. The pH of the aqueous phase is raised to 11 by the addition of solid potassium hydroxide, the mixture reextracted with chloroform, dried and concentrated to give the crude 5-amino compound. The aqueous layer is concentrated to half the volume, excess sodiom chloride is added and the mixture is reextracted with chloroform. The extract is dried and concentrated to obtain additional 5-amino compound.

The amine (21 g), triethylamine (17.9 g) and methylene chloride (600 ml) are cooled to 0°. Di-t-butyl dicarbonate (25.8 g) in methylene chloride (200 ml) is added over 30 min at 0°. The reaction mixture is stirred at 0° for 1 hr and allowed to warm to 20°-25°. The reaction mixture is washed with saturated sodium bicarbonate (3 × 200 ml), dried over potassium carbonate and the solvent removed under reduced pressure to give a solid. The solid is dissolved in ether, petroleum ether is added until the mixture is cloudy, the mixture is filtered thru celite and the filtrate is concentrated to give piperazine protected compound.

The protected piperazine compound (2.6 g) and acetaldehyde (1.7 g) in methanol (25 ml) is cooled to 0°. Sodium cyanoborohydride (0.62 g) is added in one portion. The cooling bath is removed and the mixture is permitted to warm to 30°. The mixture is stirred at 20°-25° for 2 hr. The methanol is removed under reduced pressure and the residue is partitioned between methylene chloride and a saturated sodium bicarbonate solution. The phases are separated and the organic phase is washed with saturated sodium bicarbonate solution, slaine, dried over magnesium sulfate and concentrated under reduced pressure to give an oil. The oil is purified by HPLC on silica gel, MS (M+) 334.

The oil (2.1 g), aqueous hydrochloric acid (3N, 42 ml) and ethyl acetate (57 ml) are stirred for 1 hr at 20°-25°. The mixture is cooled in ice, basified (pH=11) with potassium hydroxide (20%), the phases separated and the aqueous phase extracted again with ethyl acetate. The combined extracts are washed with saline, dried over magnesium sulfate, and concentrated under reduced pressure to give the title compound. NMR (CDCl$_3$) 1.13, 6.68, 7.12 and 7.77 δ.

PREPARATION A-60

4-[4-(5-Ethylamino-6-diethylamino)pyrimidinyl]piperazine

A solution of di-t-butyldicarbonate (4.78 g) and methylene chloride (20 ml) is added to a mixture of 1-[4-(5-amino-6-diethylamino)pyrimidinyl]piperazine (4.97 g), methylene chloride (70 ml), triethylamine (3.33 ml) and dimethylaminopyridine (10 mg). The mixture is stirred overnight. Basic workup (sodium dicarbonate/methylene chloride/magnesium sulfate) and purification by flash chromatography (hexane/ethyl acetate; 2/1) gives the carbamate of 4-[4-(5-amino-6-diethylamino)-pyrimidinyl]piperazine, MS (EI) 350.

Sodium cyanoborohydride (0.300 g) is added to a solution of the carbamate (0.652 g), methanol (13 ml) and acetaldehyde (2.1 ml). The mixture is stirred for 1 week at 20°-25°. At two day intervals similar amounts of sodium cyanoborohydride and acetaldehyde are added. Concentration and basic workup (chloroform/sodium bicarbonate/magnesium sulfate) and purification by flash chromatography (hexane/ethyl acetate; 2/1) give the t-butyl carbamate of the title compound, MS (EI) 378.

The carbamate of the title compound (465 mg), ethyl acetate (9.5 ml) and hydrochloric acid (3N, 7 ml) are stirred at 20°-25° for 2 hr. Basic workup (chloroform/solid potassium hydroxide/magnesium sulfate) provide the title comound, NMR (CDCl$_3$) 1.06, 1.07, 2.98, 2.95-3.1, 3.25, 3.35-3.45 and 8.16 δ; MS (EI) 278.

PREPARATION A-61

4-(5-amino-6-diethylamino)pyrimidinylpiperazine

A solution of diethylamine (4.0 ml) and acetonitrile (25 ml) is added dropwise over 40 min to a mixture of 4,6-dichloro-5-nitropyrimidine (7.5 g), acetonitrile (150 ml) and potassium carbonate (6.41 g) at 0°. The mixture is stirred for an additional 50 min at 0° and it then allowed to warm to 20°-25°. After 16 hr, the mixture is filtered, and the residue washed with acetonitrile (2 × 25 ml).

The crude filtrate, piperazine (25.8 g) and potassium carbonate (6.41 g) are combined and heated at reflux for 6 hr. After cooling to 20°-25°, basic workup (sodium bicarbonate/chloroform/magnesium sulfate) and purification by flash chromatography (chloroform/methanol/ammonium hydroxide; 200/10/1) an oil is obtained which solidifies upon standing to give 5-nitro-6-diethylamino-4-piperazinylpyrimidine, MS (CI, relative percent) 281 (100), 265 (13), 249 (18) and 234 (71).

5-Nitro-6-diethylamino-4-piperazinylpyrimidine (0.980 g), ethanol (25 ml) and palladium/carbon (10%, 0.25 g) are exposed to hydrogen (50 psi) for 24 hr. The mixture is filtered and the residual solids are washed with chloroform/ethanol. The combined filtrates are concentrated under reduced pressure. Basic workup (aqueous potassium hydroxide, chloroform, magnesium sulfate) provided a solid, mp 58°-59°; NMR (CDCl$_3$) 1.11, 2.95-3.05, 3.15-3.4 and 3.29 δ.

PREPARATION NA-1

8-Mesyloxy-1-octanol

Octanediol (3.656 g) in pyridine (50 ml) is stirred at 0° and methanesulfonyl chloride (2.32 ml) is added slowly.

The mixture is stirred with continued cooling for about 2 hr and then is poured into a mixture of ice (200 g) and hydrochloric acid (49 ml). The mixture is allowed to warm then is extracted with ethyl acetate (2×100 ml). The extracts are combined, washed with water, aqueous potassium bicarbonate and saline, then dried over magnesium sulfate and concentrated. The concentrate is chromatographed on silica gel (400 g) eluting with acetone/methylene chloride (5/95 and 10/90). The appropriate fractions are pooled and concentrated to give the title compound NMR (CDCl$_3$) 1.2–2.0, 3.02, 3.65 and 4.25 δ.

PREPARATION NA-2

5-Mesyloxy-1-pentanol

Following the procedure of PREPARATION NA-1 and making non-critical variation but stating with the appropriate diol, the title compound is obtained.

PREPARATION NA-3

6-Mesyloxy-1-hexanol

Following the procedure of PREPARATION NA-1 and making non-critical variation but stating with the appropriate diol, the title compound is obtained.

PREPARATION NA-4

10-Mesyloxy-1-decanol

Following the procedure of PREPARATION NA-1 and making non-critical variation but stating with the appropriate diol, the title compound is obtained.

PREPARATION NA-5

12-Mesyloxy-1-dodecanol

Following the procedure of PREPARATION NA-1 and making non-critical variation but stating with the appropriate diol, the title compound is obtained.

PREPARATION NA-6

8-[(Tetrahydropyran-2-yl)oxy]-1-octyne

6-[(Tetrahydropyran-2-yl)oxy]-1bromohexane (2.0 g) is added, with a mild exotherm, to a stirred mixture of lithium acetylide ethylenediamine (4.9 g) at 20°–25°. The mixture is stirred overnight, then is poured into ice and aqueous ammonium chloride and extracted with ether/pentane. The extracts are dried over magnesium sulfate and concentrated to give the title compound, NMR (CDCl$_3$) 1.3–2.5, 3.3–4.1 and 4.7 δ.

PREPARATION NA-7

4-(6-bromohexyloxy)phenol

A mixture of hydroquinone (16.5 g), 1,6-dibromohexane (7.32 g) and ethanol (60 ml) is added dropwise over 3–5 min to a solution of potassium hydroxide (85%, 2.0 g) and ethanol (20 ml). The mixture is heated at reflux for 4 hr and then allowed to cool. Silica gel (30 g) is added to the solution and the ethanol is removed at reduced pressure. The residue is chromatographed on silica gel (200 g) and eluted with ethyl acetate/hexane (33/67) to give the title compound, m.p. 43°–45°; MS (m/e)=272, 274 (M$^+$).

PREPARATION NA-8

4-(5-Iodopentyloxy)phenol

Following the general procedure of PREPARATION NA-7 and making non-critical variations but starting with 1,5-diiodopentane, the title compound is obtained, MS (m/e)=306 (M$^+$).

PREPARATION NA-9

4-(4-Iodobutyloxy)phenol

Following the general procedure of PREPARATION NA-7 and making non-critical variations but starting with 1,4-diiodobutane, the title compound is obtained, m.p. 51°–53°; MS (m/e)=292 (M$^+$).

PREPARATION NA-10

4-(6-Bromohexyloxy)anisole

A mixture of 4-methoxyphenol (5.0 g), 1,6-dibromohexane (31 ml), potassium carbonate (6.13 g) and acetonitrile (50 ml) are heated at reflux for 24 hr. The mixture is allowed to cool to 20°–25° and the small amount of solids that formed are collected, dissolved in chloroform, washed with water, dried over sodium sulfate and the solvent removed at reduced pressure to give the diarylhexane side product. The reaction mother liquor is concentrated at reduced pressure and the 1,6-dibromohexane distilled off (bp=75° at 0.25 mm). The distillation residue is dissolved in ether (50 ml) and the product allowed to crystallize to give the title compound, m.p. 51.5°–53°; MS (m/e)=286, 288 (M$^+$).

PREPARATION NA-11

4-(6-Hydroxyhexyloxy)anisole

A mixture of 4-methoxyphenol (8.7 g), potassium carbonate (9.7 g), 6-chlorohexanol (9.55 g) and DMSO (80 ml) is heated at 120° for 18 hr. Most all of the DMSO is removed at reduced pressure and the residue distributed between ether (400 ml) and water (400 ml). The ether phase is washed with water, saline, dried over sodium sulfate and the solvent removed at reduced pressure to give a residue which is crystallized from ether to give the title compound, m.p. 63°–64°; MS (m/e) 224 (M$^-$).

PREPARATION NA-12

1,2-Methylenedioxy-4-[3-mesyloxypropyl]benzene

A solution of 1,2-methylenedioxy-4-[3-hydorxy-propyl]benzene, (10.0 g), methanesulfonyl chloride (6.33 g, 4.28 ml) and triethylamine (5.6 g) in methylene chloride (100 ml) is stirred at 0° for 2 hr. The reaction mixture is partitioned between methylene chloride and aqueous sodium bicarbonate. The organic phase is dried over sodium sulfate and concentrated. The residue is dissolved in acetonitrile (100 ml).

PREPARATION NA-13

2-Bromo-4-methoxyacetophenone

Can be purchased from Aldrich Chemical Co.

PREPARATION NA-14

4-[3,5-Dimethyl-4-methoxyphenyl)butanol

A mixture of 2,6-dimethylanisole (4.45 g), succinic anhydride (4.80 g) and aluminum chloride (4.70 g) in toluene (60 ml) is stirred for 2.7 hr at 20°–25°. A 100 ml aliquot of methylene chloride is added for solubility. The reaction is run for 6 hr. The reaction is poured onto ice and extracted with methylene chloride-isopropanol. The organic phase is washed with saline, dried over sodium sulfate, concentrated and dried under reduced pressure overnight to give a solid. This material is stirred with borane-methyl sulfide complex (1.0M, 38 ml) in THF at 20°-25° for 24 hr. Aqueous sodium bicarbonate, methylene chloride and water are added. The ketoalcohol product is combined with other partly reduced materials and treated with borane-methyl sulfide complex in excess in methylene chloride for 72 hr. It is important that the ketoacid Friedel Crafts adduct should be reduced exhaustively with excess borane-methyl sulfide complex.

PREPARATION NA-15

4-[3,5-Dimethyl-4-hydroxyphenyl]butanol

A solution of 4-[3,5-dimethyl-4-methoxyphenyl]-butanol (PREPARATION NA-14, 4.96 g), boron tribromide (1.0M in methylene chloride, 47 ml) in methylene chloride (200 ml) is stirred at −70° and then allowed to warm to 20°-25° over 4 hr. The reaction did not begin until the reaction reached room temperature. The reaction mixture is partitioned between methylene chloride and aqueous sodium bicarbonate. The organic phase is dried over sodium sulfate and concentrated to give the phenol which had a consistent NMR. A sample of the phenol (5.00 g) is dissolved in methylene chloride (100 ml) and is treated at 0° with triethylamine (6.28 g) and methanesulfonyl chloride (7.09 g). After 3 hr, the reaction mixture is partitioned between methylene chloride and aqueous sodium bicarbonate. The organic phase is dried over sodium sulfate and concentrated to give the title compound which had an NMR consistent for the bis-mesylate.

PREPARATION NA-16

1-Bromo-3-phenylpropane [637-59-2]

PREPARATION NA-17

6-(4-Methoxyphenoxy)-1-iodohexane

Methanesulfonyl chloride (3.2 ml) is added slowly to a stirred solution of 6-(4-methoxyphenoxy)-1-hexanol (7.84 g) in pyridine (88 ml) at 0°. The mixture is stirred for 1 hr then poured into a mixture of ice (300 g) and concentrated hydrochloric acid (87 ml). The mixture is stsirred for about 1 hr, then filtered. The filter cake is washed with water. The damp product is dissolved in ethyl acetate, the solution is washed with saline, dried over magnesium sulfate and concentrated to give the mesylate of the desired compound. The mesylate and sodium iodide (28 g) in acetone (400 ml) are stirred under reflux for 1 hr, and then filtered. The filter cake is washed with acetone. The filtrate is concentrated and the residue is dissolved in ethyl acetate. The solution is washed with sodium thiosulfite (2% aqueous), saline, dried over sodium sulfate and concentrated to give a solid. The solid is chromatographed on silica gel (550 g) and eluted with methylene chloride. The appropriate fractions are pooled and concentrated to give the title compound, m.p. 64°-66°.

PREPARATION NA-18

8-(4-Methoxyphenoxy)-1-octyne

Following the general procedure of PREPARATION NA-6 and making non-critical variations but starting with 6-(4-methoxyphenoxy)-1-iodohexane (PREPARATION NA-17), the title compound is obtained, NMR (CDCl$_3$) 1.3-2.3, 3.78, 3.92 and 6.92 δ.

PREPARATION NA-19

3-(3,5-Dimethyl-4-hyroxyphenyl)propanol bismesylate

Part I—3-(3,5-Dimethyl-4-hydroxyphenyl)propanol 2,6-Dimethylphenol (1.22 g) is added to a mixture of powdered potassium hydroxide (2.24 g) in dimethylsulfoxide (20 ml). Then 3-bromopropane (2.42 g) is added at 20°-25° and stirred for 0.5 hr. The mixture is diluted with water (100 ml) and extracted with methylene chloride (3×). The organic extracts are washed with water (2×) and then with saline, dried over sodium sulfate and concentrated under reduced pressure to give 1-allyloxy-2,6-dimethylbenzene.

A mixture of 1-allyloxy-2,6-dimethylbenzene (1.4 g) and 1methyl-2-pyrrolidinone (3 ml) is refluxed under nitrogen for 6 hr. The reaction mixture is cooled, diluted with ether, washed with aqueous hydrochloric acid (10%, 2×), dried over sodium sulfate and concentrated to give 3-(3,5-dimethyl-4-hydroxy)propene.

A solution of borane-dimethylsulfide (10M) is added to an ice-cold solution of 3-(3,5-dimethyl-4-hydroxy)-propene (1.6 g) and stirred at 0° for 0.5 hr, then at 20°-25° for 0.5 hr. The reaction is then quenched with water (3 ml). After the effervescence ceases, a solution of aqueous sodium hydroxide (20%) is added until a faint pink color develops, and then aqueous hydrogen peroxide (30%, 1.3 ml) is added to the mixture at 0°. The reaction is stirred overnight at 20°-25°. The mixture is diluted with water and extracted with ether. The ether extracts are combined, washed with water, dried over magnesium sulfate, and concentrated. The concentrate is flashed chromatographed on silica gel (230-400 mesh) eluting with ethyl acetate/hexane (30/70). The appropriate fractions are pooled and concentrated to give 3-(3,5-dimethyl-4-hydroxyphenyl)propanol.

Part II—3-(3,5-Dimethyl-4-hydroxyphenyl)propanol bismesylate

Methanesulfonyl chloride (1.2 g) in dichloromethane (2 ml) is added dropwise to an ice-cold solution of 3-(3,5-dimethyl-4-hydroxyphenyl)propanol (0.85 g) and triethylamine (1.6 ml) is methylene chloride (10 ml). The mixture is stirred for 0.5 hr and then diluted with an ice-cold aqueous solution of sodium bicarbonate. The phases are separated, the organic phase is dried over sodium sulfate and concentrated to give 3-(3,5-dimethyl-4-hydroxyphenyl)propanol bismesylate.

PREPARATION NA-20

3-(3,5-Dimethyl-4-methoxyphenyl)-1-propanol 3-(3,5-Dimethyl-4-hydroxyphenyl)-1-propene (5.0 g) is added to a mixture of powdered potassium hydroxide (7.98 g) in dimethylsulfoxide (50 ml) at 15°. Iodomethane (8.8) is then added and stirred below 20° for 0.5 hr. The reaction mixture is poured into ice/water and the product is extracted with ether (2×). The ether extracts are washed with water (3×), saline, dried over sodium sulfate and concentrated under reduced pressure to give 3-(3,5-dimethyl-4-methoxyphenyl-1-propene. The "propene" is transformed to the corresponding "propanol" with borane-dimethylsulfide by the general procedure of PREPARATION NA-19 to give the title compound.

PREPARATION NA-21

2-(3,5-Dimethyl-4-hydroxyphenyl)-1-ethanol

Ozone is bubbled into a solution of 3-(3,5-dimethyl-4-hydroxy)propene (see PREPARATION NA-19, Part I, 3.77 g) in methanol (60 ml) at −78° until the starting material is no longer detected by TLC. Nitrogen is then passed through the solution for 15 min at −78°. Sodium borohydride (1.0 g) is added carefully in portions and the mixture is then permitted to warm to 20°-25°. The reaction is quenched with saturated aqueous solution of ammonium chloride. The mixture is acidified with aqueous hydrochloric acid, following which the product is extracted with methylene chloride (5×). The extracts are combined, washed with saline, dried over sodium sulfate and concentrated. The concentrate is flash chromatographed on silica gel (230–400 mesh), eluting with ethyl acetate/hexane (50/50). The appropriate fractions are pooled to give the title compound.

PREPARATION NA-22

2-(3,5-Dimethyl-4-methoxyphenyl)-1-ethanol

Following the general procedure of PREPARATION NA-21 and making non-critical variations but starting with 3-(3,5-dimethyl-4-methoxy)propene (see PREPARATION NA-20), the title compound is obtained.

PREPARATION NA-23

6-(3,5-Dimethyl-4-methoxyphenyl)-1-hexanol mesylate

Bromine is added dropwise to a solution of 2,6-dimethylanisole (12.0 g) in chloroform (100 ml) at about 5°. The solution is stirred at 5° for 2 hr and then allowed to warm to 20°-25°. The reaction mixture is poured into ice-water, and the phases are separated. The chloroform phase is washed with water, aqueous sodium bisulfite solution, then with water, dried over sodium sulfate and concentrated under reduced pressure to give 3,5-dimethyl-4-methoxybromobenzene.

3,5-Dimethyl-4-methoxybromobenzene (8.0 g) in THF is added dropwise to a mixture of magnesium turnings (1.1 g), a crystal of iodine and THF (25 ml) at 20°-25°. The mixture is refluxed for 18 hr.

The Grignard reagent is cooled to 20°-25° and a solution of cyclohexanone (4.0 g) in THF (60 ml) is added over a period of 5 min. The mixture is stirred at 20°-25°, then refluxed for 6 hr. The solution is quenched with a saturated aqueous solution of ammonium chloride, and the product is extracted with ether (2×). The ether extracts are washed with water then with saline, dried over magnesium sulfate and concentrated under reduced pressure at 45° to give the desired alcohol, the structure of which is supported by NMR. Chromium trioxide (18.4 g) is added in portions to the alcohol 7.85 g) in glacial acetic acid (250 ml) at 20°-25°. An induction period of about 15 min takes place with a termperature rise to 35°. The mixture is maintained between 28°-32° with occassional cooling with a water bath. The reaction is stirred for an additional hour after the exotherm ceases and then poured into ice (1 l). The product is extracted with chloroform (3×), the extracts washed with water (100 ml), then with saline, dried over sodium sulfate and concentrated. The concentrate is dissolved in aqueous sodium hydroxide and washed with ether (2×). The aqueous basic phase is chilled, traated with activated charcoal, filtered, and acidified with hydrochloric acid (12N). The product is extracted with chloroform (2×), dried over sodium sulfate and concentrated to give the keto-acid.

Borane-tetrahydrofuran (1N, 40 ml) is syringed into an ice-cold solution of the keto-acid (5.1 g) in THF (50 ml). The solution is stirred at 5° for 0.5 hr, then at 20°-25° for 20 hr. The solution is quenched with aqueous hydrochloric acid. The phases are separated and the aqueous phase is extracted with ether. The extracts are washed with water and then with saline, dried over magnesium sulfate and concentrated. The concentrate is dissolved in acetic acid (90 ml), absolute ethanol (20 ml) and concentrated hydrochloric acid (6 ml) in a Parr bottle. Palladium on charcoal (10%, 2.65 g) is added and the mixture charged with 50 psi of hydrogen. Hydrogen uptake ceases after 4.5 hr. The catalyst is removed by filtration and washed with ethanol. The filtrate is concentrated under reduced pressure, diluted with water and the product extracted with ether. The ether extracts are washed wilth saturated sodium bicarbonate, water, saline, dried over magnesium sulfate and concentrated. The concentrate (3.2 g) is refluxed in a mixture of sodium hydroxide (20%, 25 ml) and methanol (10 ml) for 1 hr. The mixture is cooled and then extracted with ether (2×). The ether extracts are washed with water, dried over magnesium sulfate and concentrated.

A solution of methanesulfonyl chloride (1.18 g) in methylene chloride (10 ml) is added dropwise to an ice-cold solution of the concentrate (2.1 g), triethylamine (1.7 ml) in methylene chloride (50 ml). The mixture is stirred and then washed with water, sodium bicarbonate solution, dried over sodium sulfate, and concentrated to give the title compound.

PREPARATION NA-24

3-Oxo-1-cyclohexene butanal

Butylmagnesium chloride (2.0M, 20.0 ml) is added dropwise over 20 min to a solution of 4-chloro-1-butanol (4.05 g) and THF (40.0 ml). The resultant solution is stirred for 20 min and then is added dropwise over 20 min to a mixture of magnesium (1.46 g) and THF (5.0 ml). The resulting warm mixture is heated at reflux for 3 hr, and then cooled in an ice bath. A solution of 3-ethoxy-2-cyclohexene-1-one (5.39 ml) and THF (20.0 ml) is then added dropwise over 20 min. The resultant solution is allowed to warm to 20°-25° and stir for 2 hr. Acidic workup using ether and hydrochoric acid (1%) and purification by flash chromatography eluting with ethyl acetate/hexane (4/1) provides 3-(4-hydroxybutyl)-cyclohex-2-en-1-one as an oil, IR (neat) 3413, 2942, 1664, 1600, 1257, 1185 cm$^{-1}$; MS (EI) m/e (relative %) 168 (25), 123 (25), 97 (40), 82 (36), 55 (44), 42 (100).

Following the procedure of Corey, Tetrahedron Lett 2647 (1975), a mixture of 3-(4-hydroxybutyl)-cyclohex-2-en-1-one (539 mg) pyridinium dichromate (2.05 g) and methylene chloride (8.0 ml) is stirred for 25 hr at 20°-25°. The reaction is diluted with ether, filtered, dried over magnesium sulfate and concentrated to give the title compound, IR (neat) 2950, 1724, 1666, 1255, 1193, 888 cm$^{-1}$.

PREPARATION NA-25

3-Oxo-1-cyclohexanal

Following the general procedure of PREPARATION NA-24 and making non-critical variations but using 6-chloro-1-hexanol, the title compound is obtained. IR (neat) 2938, 1730, 1667, 1254, 1193 cm⁻¹.

PREPARATION NA-26

3-Oxo-1-cyclohexene propanal

A solution of 2-(2-bromoethyl)1,3-dioxalane (14.8 g) and THF (76 ml) is added dropwise over 35 min to a mixture of magnesium (3.98 g) and THF (27.1 ml). The resultant mixture is stirred for 1.5 hr at 20°-25° before being cooled to 0° in an ice bath. A solution of 3-ethoxy-2-cyclohexene-1-one (8.45 g) and THF (27.0 ml) is added dropwise over 20 min. The resultant solution is stirred for 1 hr at 0° and 30 min at 20°-25°. Acidic workup using ether and hydrochloric acid (1%) and purification by flash chromatography ethyl acetate/hexane (4/1-1/0) provides 3-(2-(1,3-dioxolan-2-yl)ethyl)cyclohex-2-en-1-one as an oil. IR (neat) 2950, 2886, 1667, 1138 cm⁻¹.

A solution of 3-(2-(1,3-dioxolan-2-yl)ethyl)cyclohex-2-en-1-one (3.00 g), acetone (60.0 ml) and perchloric acid (3N, 10.0 ml) is stirred for 4 hr at 20°-25°. Aqueous saturated sodium bicarbonate (150 ml) is added and the mixture concentrated. Aqueous workup provides the title compound. IR (neat) 2950, 1720, 1666, 1257, 1194, 969, 732 cm⁻¹.

PREPARATION NA-27

4-Phenoxy-1-bromobutane [1200-03-9]

EXAMPLE 1

4-[4,6-Bis(1-pyrrolidinyl)-1,3,5-triazin-2-yl]-1-piperazinehexanol (II/A-45)

A mixture of 6-bromohexanol (0.905 g), 2,6-bis(1-pyrrolidinyl)-4-(1-piperazinyl)-1,3,5-triazine (PCT 86/01797, PREPARATION A-45, 1.517 g), potassium carbonate (0.346 g) and sodium iodide (0.075 g) in acetonitrile (165 ml) are stirred under reflux for 4.5 hr. The mixture is concentrated and the residue is partitioned between methylene chloride and potassium bicarbonate (1N). The phases are separated, the organic phase is washed with water and saline, then filtered through sodium sulfate and concentrated. The residue is chromatographed on silica gel (230 g) packed in methanol/methylene chloride (5/95). Elution is performed with 5% methanol/methylene chloride (3 l) followed by 10% methanol/methylene chloride (2 l). 50 ml fractions are collected. fractions 61-78 are pooled and concentrated to give the title compound.

EXAMPLE 1A

4-[4,6-Bis(1-pyrrolidinyl)-1,3,5-triazin-2-yl]-1-piperazinehexanol methane sulfonate (II/A-45)

A mixture of 4-[4,6-bis(1-pyrrolidinyl)-1,3,5-triazin-2-yl]-1-piperazinehexanol (EXAMPLE 1, 1.22 g) in methylene chloride/ether (1/1, 30 ml) is mixed with a solution of methanesulfonic acid (0.28 g) in ether (15 ml). The mixture is concentrated and the residue crystallized twice from methanol/ether to give the title compound.

EXAMPLES 2-16

See CHART D for Column A and Column B.
Following the general procedure of EXAMPLE 1 and making non-critical variations but starting with (a) the non-amine halide or mesylate (Column A) corresponding to the non-amine portion of the desired alkyl amine (II) and (b) the amine (Column B) corresponding to the amine portion of the desired alkyl amine (II), the alkyl amines (II, Column C) are obtained:

| EXAMPLE | Column C Alkyl amine (II) |
|---|---|
| 2 | 4-(2-pyridinyl)-1-piperazinehexanol (II/A-6) |
| 3 | 4-[3-(ethylamino)-2-pyridinyl]-1-piperazinehexanol (II/A-47) |
| 4 | 4-[(3,6-bis(2-pyridinyl)-4-pyridazinyl)methyl]-1-piperazinehexanol (II/A-52) |
| 5 | 6-[bis(2-pyridinylmethyl)amino]-1-hexanol (II/A-54) |
| 6 | 2,4-bis(1-pyrrolidinyl)-6-(4-tetradecyl-1-piperazinyl)-pyrimidine (II/A-22) |
| 7 | methyl 5-[4-(2,6-bis(1-pyrrolidinyl)-4-pyrimidinyl)-1-piperazinyl]pentanoate (II/A-22) |
| 8 | 2,4-bis(1-pyrrolidinyl)-6-(4-hexyl-1-piperazinyl) pyrimidine (II/A-22) |
| 9 | 4-[2,6-bis(1-pyrrolidinyl)-4-pyrimidinyl]-1-piperazine hexanol (II/A-22) |
| 10 | 4-[2,6-bis(1-pyrrolidinyl)-4-pyrimidinyl]-1-piperazine-dodecanol (II/A-22) |
| 11 | 4-[2,6-bis(1-pyrrolidinyl)-4-pyrimidinyl]-1-piperazine-octanol (II/A-22) |
| 12 | 4-[2,6-bis(1-pyrrolidinyl)-4-pyrimidinyl]-1-piperazine-pentanol (II/A-22) |
| 13 | 4-[2,6-bis(1-pyrrolidinyl)-4-pyrimidinyl]-1-piperazine-decanol (II/A-22) |
| 14 | 4-[3-(ethylamino)-2-pyridinyl]-1-piperazinedecanol (II/A-47) |
| 15 | 4-[3-(ethylamino)-2-pyridinyl]-1-piperazineoctanol (II/A-47) |
| 16 | 4-[2,6-bis(2-pyridinyl)-1,3,5-triazin-4-yl]-1-piperazine hexanol (II/A-49) |

EXAMPLES 2A-16A

Following the general procedure of EXAMPLE 1A and making non-critical variations but using the alkyl amines (II) of EXAMPLES 2-16 and the appropriate acid, the salts of the corresponding alkyl amines (II) of EXAMPLES 2A-16A are obtained.

| EXAMPLE | Alkyl amine salt (II) |
|---|---|
| 2A | 4-(2-pyridinyl)-1-piperazinehexanol monomethane sulfonate |
| 3A | 4-[3-(ethylamino)-2-pyridinyl]-1-piperazinehexanol dihydrochloride |
| 4A | 4-[(3,6-bis(2-pyridinyl)-4-pyridazinyl)methyl]-1-piperazinehexanol dihydrochloride |
| 5A | 6-[bis(2-pyridinylmethyl)amino]-1-hexanol dihydrochloride |
| 6A | 2,4-bis(1-pyrrolidinyl)-6-(4-tetradecyl-1-piperazinyl)-pyrimidine dihydrochloride |
| 7A | methyl 5-[4-(2,6-bis(1-pyrrolidinyl)-4-pyrimidinyl)-1-piperazinyl]pentanoate methane sulfonate |
| 8A | 2,4-bis(1-pyrrolidinyl)-6-(4-hexyl-1-piperazinyl) pyrimidine monomethane sulfonate |
| 9A | 4-[2,6-bis(1-pyrrolidinyl)-4-pyrimidinyl]-1-piperazinehexanol monomethane sulfonate |
| 9B | 4-[2,6-bis(1-pyrrolidinyl)-4-pyrimidinyl]-1-piperazinehexanol dihydrochloride |
| 10A | 4-[2,6-bis(1-pyrrolidinyl)-4-pyrimidinyl]-1-piperazinedodecanol dihydrochloride |
| 11A | 4-[2,6-bis(1-pyrrolidinyl)-4-pyrimidinyl]-1-piperazineoctanol dihydrochloride |
| 12A | 4-[2,6-bis(1-pyrrolidinyl)-4-pyrimidinyl]-1-piperazinepentanol dihydrochloride |
| 13A | 4-[2,6-bis(1-pyrrolidinyl)-4-pyrimidinyl]-1-piperazinedecanol dihydrochloride |
| 14A | 4-[3-(ethylamino)-2-pyridinyl]-1-piperazinedecanol dihydrochloride |
| 15A | 4-[3-(ethylamino)-2-pyridinyl]-1-piperazineoctanol dihydrochloride |
| 16A | 4-[2,6-bis(2-pyridinyl)-1,3,5-triazin-4-yl]-1-piperazinehexanol monomethane sulfonate |

EXAMPLE 17

3,6-Bis(2-pyridinyl)-4-pyridazine hexanol (II/A-55)

A mixture of 8-[(tetrahydropyran-2-yl)oxy]-1-octyne (PREPARATION NA-6, 1.5 g) and 3,6-bis(2-pyridinyl)-1,2,4,5-tetrazine (1.68 g) in toluene (50 ml) is heated under reflux for about 48 hr. The mixture is concentrated and the residue chromatographed on silica gel (200 g) packed in acetone/methylene chloride (20/80). Elution is performed with acetone/methylene chloride (1 l of 1/99 and 3 l of 20/80). The appropriate fractions are pooled to give the tetrahydropyranyl ether of the title compound. A mixture of this compound (1.23 g) in acetone (45 ml, methanol is preferred) and hydrochloric acid (1N, 5 ml) is allowed to stand overnight at 20°-25°. The mixture is concentrated and extracted with ether. The extracts are dried over magnesium sulfate and concentrated to an oil. The oil is chromatographed on silica gel (100 g) eluting with methanol/methylene chloride (5/95). The appropriate fractions are pooled to give the title compound.

EXAMPLE 17A 3,6-Bis(2-pyridinyl)-4-pyridazine hexanol dihydrochloride 3,6-Bis(2-pyridinyl)-4-pyridazine hexanol (EXAMPLE 17, 0.167 g) is dissolved in water (6 ml) containing hydrochoric acid (2 equivalents), filtered and freeze dried to give the title compound.

EXAMPLE 18

[4-(2,6-Bis(1-pyrrolidinyl)-4-pyrimidinyl)-1-piperazine]-6-hydroxy-2,5,7,8-tetramethylchroman-2-carboxamide (III/A-22)

6-Hydroxy-2,5,7,8-tetramethylchroman-2-carboxylic acid (1.0 g) in THF (10 ml) is added in several batches 1,1'-carbonyldiimidazole (0.64 g). The mixture was stirred at 20°-25° for 30 min at which time a slurry of 2,6-bis(1-pyrrolidinyl)-4-(1-piperazinyl)pyrimidine (PREPARATION A-22, 1.2 g) in THF (10 ml) is allowed to slowly run into the mixture. The last traces of the amine are washed into the reaction mixture with THF (5-10 ml). The mixture was stirred for 18 hr, the solvent was removed at reduced pressure. The residue is dissolved in chloroform (75 ml), washed with water (75 ml), dried over sodium sulfate and the solvent removed at reduced pressure to leave a residue. This material is flash chromatographed on silica gel (100 g) eluting was 50% ethyl acetate in hexane to give a solid which is crystallized from ethyl acetate to give the title compound.

EXAMPLE 19

[4-(3-(N-Ethylamino)pyrid-2-yl)-piperazin-1-yl)methyl]-6-hydroxy-2,5,7,8-tetramethylchroman-2-carboxamide (III/A-47)

Following the general procedure of EXAMPLE 18 and making non-critical variations but using 4-[3-(ethylamino)-2-pyridinyl]piperazine (PREPARATION A-47) the title compound is obtained.

EXAMPLE 20

[4-(2,6-Bis(pyridin-2-yl)pyrimidin-4-yl)piperazin-1-yl]-6-hydroxy-2,5,7,8-tetramethylchroman-2-carboxamide (III/A-51)

Following the general procedure of EXAMPLE 18 and making non-critical variations but using 4-[2,6-bis(2-pyridinyl)-4-pyrimidinyl]piperazine (PREPARATION A-51) the title compound is obtained.

EXAMPLE 21

2-[[4-(2,6-Bis-(1-pyrrolidinyl)-4-pyrimidinyl)-1-piperazinyl]methyl]-3,4-dihydro-2,5,7,8-tetramethyl-2H-1-benzopyran-6-ol (III/A-22)

To a suspension of lithium aluminum hydride (0.55 g) and THF (50 ml) Is added dropwise over 20-30 min at 25° a solution of [4-(2,6-bis(1-pyrrolidinyl)-4-pyrimidinyl)-1-piperazine]-6-hydroxy-2,5,7,8-tetramethylchroman-2-carboxamide (EXAMPLE 18, 3.5 g) in THF (50 ml). The mixture is stirred for 18 hr at 20°-25°, cooled to 0° and treated dropwise with water (0.6 ml), aqueous sodium hydroxide (10%, 0.6 ml) and water (1.5 ml) with stirring for 30 min. The mixture is filtered through celite, the solids are washed with ethyl acetate (50 ml, 2×) are the combined wash and filtrates are concentrated under reduced pressure. The residue is dissolved in methylene chloride (150 ml), washed with water, dried over sodium sulfate and the solvent removed under reduced pressure. The residue is flashed chromatographed on silica gel (100 g) eluting with hexane in ethyl acetate (33/67) to give a residue which after crystallization from ether and hexane gives the title compound.

EXAMPLE 22

2-[[4-[3-(Ethylamino)-2-pyridinyl]-1-piperazinyl]methyl]-3,4-dihydro-2,5,7,8-tetramethylbenzopyran-6-ol (III/A-47)

Following the general procedure of EXAMPLE 21 and making non-critical variations but starting with [4-(3-(N-ethylamino)pyrid-2-yl)-piperazin-1-yl)methyl]-6-hydroxy-2,5,7,8-tetramethylchroman-2-carboxamide (EXAMPLE 19), the title compound is obtained.

EXAMPLE 22A

2-[4-3(-N-Ethylamino)pyrid-2-yl)-piperazin-1-yl)methyl]-6-hydroxy-2,5,7,8-tetramethylchroman hydrochloride (IIIA-47)

The hydrogen chloride addition salt was prepared by the addition of a saturated solution of hydrogen chloride in ether to a ether solution of 2-[4-3(-N-ethylamino)pyrid-2-yl)-piperazin-1-yl)methyl]-6-hydroxy-2,5,7,8-tetramethylchroman (EXAMPLE 22). The solvent is removed at reduced pressure and the material crystallized from methanol and ether to give the title compound partially hydrated.

EXAMPLE 23

2-[4-((2,6-Bispyrid-2-yl)pyrimidin4-yl)piperazin-1-yl)methyl]-6-hydroxy-2,5,7,8-tetramethylchroman (III/A-51)

A mixture of 6-hydroxy-2,5,7,8-tetramethychroman-2-carboxylic acid (5.0 g), methanol (100 ml) and p-toluenesulfonic acid (5 mg) is heated at reflux for 18 hr. The mixture is allowed to cool to 20°-25° and the solid collected and washed with ether and dried to give methyl-6-hydroxy-2,5,7,8-tetramethylchroman-2-carboxylate. Methyl-6-hydroxy-2,5,7,8-tetramethychroman-2-carboxylate in THF (50 ml), is added to a suspension of lithium aluminum hydride (1.58 g) in THF (50 ml) at 0° dropwise over 15-20 min. The mixture is stirred at 0° for 30 min then at 20°-25° for 18 hr. The mixture is cooled to 0° and quenched by dropwise addition of ethyl acetate (10 ml), water (1.6 ml), aqueous sodium hydroxide (15%, 1.6 ml) and then water (4.8 ml). The mixture is stirred at 0° for 30 min then filtered. The solids are washed with THF (25 ml, 2×). The combined washes and filtrate are concentrated at reduced pressure and the residue is dissolved in ethyl acetate (150 ml), washed with water (100 ml), dried over sodium sulfate and the solvent removed at reduced pressure to a solid. A mixture of the solid (3.0 g), pyridine (3 ml) and chloroform (15 ml) is cooled to 0°. To this mixture is added p-toluenesulfonyl chloride (3.6 g) in several small portions. The mixture is allowed to stand at 15° for 3 days then chloroform (50 ml) is added. The mixture is washed with water (100 ml), aqueous hydrochloric acid (5%, 100 ml), dried over sodium sulfate and the solvent removed at reduced pressure to give a crude tosylate (5.0 g). The crude tosylate is heated at 120° with piperazine (21.5 g) for 5 hr. The mixture was allowed to cool and distributed between dichloromethane (150 ml) and water (100 ml). The phases are separated and the organic phase is washed with water (100 ml), dried over sodium sulfate and the solvent removed at reduced pressure to leave an oil. This material is flash chromatographed on silica gel (200 g) eluting with ammonia, methanol, ethyl acetate (0.5/4.5/95). The appropriate fractions are pooled and concentrated to give a residue. A mixture of the residue (0.3 g), chlorodipyridinylpyrimidine (J.A.C.S., 32, 1591 (1967), 0.27 g), potassium carbonate (0.14 g) and acetonitrile (15 ml) is heated at reflux for 2 days. The solvent is removed at reduced pressure, the residue was distributed between methylene chloride (30 ml) and water (30 ml). The phases are separated and the organic phase is dried over sodium sulfate and the solvent removed at reduced pressure to leave a solid. This material was flash chromatographed on silica gel (30 g) eluting with ammonia, methanol, ethyl acetate (1/9/90) to give a solid which upon crystallization from ethyl acetate give the title compound.

EXAMPLE 24

2,6-Bis(1,1-dimethylethyl)-4[[4-[2-[4-(2,6-bis(1-pyrrolidinyl)-4-pyrimidinyl)-1-piperazinyl]ethyl]-1-piperazinyl]methyl]phenol (I/A-53)

A solution of methanesulfonylchloride (0.29 g) in methylene chloride (5 ml) is added dropwise to a stirred solution of 4-[[3,5-bis(1,1-dimethylethyl)-4-hydroxyphenyl]methyl]-1-piperazineethanol (0.8 g), triethylamine (0.25 g) and methylene chloride (10 ml) is added at 0°. The mixture is stirred at 0° for 30 min and then at 20°-25° for 1 hr. The mixture is washed with water, dried over sodium sulfate and the solvent removed at reduced pressure to give an oil The oil is flash chromatographed on silica gel (60 g) eluting with methanol/ethyl acetate (5/95). The appropriate fractions are pooled and concentrated to give the desired mesylate. Acetonitrile (5 ml), 2,6-bis(1-pyrrolidinyl)-4-(1-piperazinyl)-pyrimidine (0.3 g) and potassium carbonate (0.13 g) are added to the mesylate. The mixture is heated at reflux for 4 hr, cooled and the solvent removed at reduced pressure. The residue is dissolved in methylene chloride (25 ml), washed with water, dried over sodium carbonate and the solvent removed at reduced pressure to give a residue which is flash chromatographed on silica gel (60 g) eluting with ethyl acetate/hexane (33/67) to give the title compound.

EXAMPLE 24A 2,6-Bis(1,1-dimethylethyl)-4[[4-[2-[4-(2,6-bis(1-pyrrolidinyl)-4-pyrimidinyl)-1-piperazinyl]ethyl]-1-piperazinyl]methyl]phenol fumerate (1:1)

The fumarate salt is prepared by addition of fumaric acid (84 mg) to 2,6-bis(1,1-dimethylethyl)-4[[4-[2-[4-(2,6-bis(1-pyrrolidinyl)-4-pyrimidinyl)-1-piperazinyl]ethyl]-1-piperazinyl]methyl]phenol (EXAMPLE 24) in methanol to obtain the title compound.

EXAMPLE 25

4-[4-[6-(4-Methoxyphenoxy)hexyl]-1-piperazinyl]-2,6-bis(1-pyrrolidinyl)]pyrimidine (I/A-22)

p-Toluenesulfonylchloride (2.34 g) is added to a mixture of 4-(6-hydroxyhexyloxy)anisole (PREPARATION NA-11, 2.5 g) in pyridine (25 ml) previously cooled to about 15°. The mixture is allowed to stand at about −15° for 24 hr and then allowed to warm to 20°-25° for 4 hr. The mixture is dissolved in ether (200 ml) and washed with cold aqueous hydrochoric acid (10%, 200 ml). The phases are separated and the ethereal phase is washed wtih water, saturated sodium bicarbonate, saline, dried over sodium sulfate and the solvent removed at reduced pressure to give the crude tosylate. To this tosylate (0.64 g) is added 2,6-bis(1-pyrrolidinyl)-4-(1-piperazinyl)pyrimidine (PREPARATION A-22, 0.56 g), potassium carbonate 260 mg) and acetonitrile (20 ml). The mixture is heated at reflux for 2.5 hr and the solvent removed at reduced pressure. The residue is distributed between chloroform (75 ml) and water (75 ml). The organic phase is dried over sodium sulfate and the solvent removed at reduced pressure to give a solid which is crystallized from ethyl acetate to give the title compound.

EXAMPLE 26

N-Ethyl-2-[4-[6-(4-methoxyphenoxy)hexyl]-1-piperazinyl]-3-pyridinamine (I/A-47)

A mixture of the tosylate (EXAMPLE 25, 0.66 g), 4-[3-(ethylamino)-2-pyridinyl]piperazine (PREPARATION A-47, 1.2 g), potassium carbonate (0.44 g) and acetonitrile (10 ml) is heated at reflux for 2.5 hr. The solvent is removed at reduced pressure and the residue is distributed between chloroform (30 ml) and water (30 ml). The organic phase is dried over sodium sulfate and the solvent removed at reduced pressure to give an oil. The oil is flashed chromatographed on silica gel eluting with ethyl acetate. The appropriate fractions are pooled to give the title compound.

EXAMPLE 26A

N-Ethyl-2-[4-[6-(4-methoxyphenoxy)hexyl]-1-piperazinyl]-3-pyridinamine fumerate

N-Ethyl-2-[4-[6-(4-methoxyphenoxy)hexyl]-1-piperazinyl]-3-pyridinamine (EXAMPLE 26) is dissolved in methanol (10 ml), fumeric acid (0.24 g) is added and the mixture allowed to stand for 30 min at 20°-25°. The mixture is clouded with ether and allowed to crystallize at about 15° to give the title compound.

EXAMPLES 27-39

See CHART E for Column A and Column B.

Following the general procedures of EXAMPLES 25 and 26 and making non-critical variations but starting with the non-amine (NA-#) of Column A and the amine (A-#) of Column B, the corresponding aromatic amine (I) of Column C is obtained:

| EXAMPLE | Column C. Aromatic Amine (I) |
|---|---|
| 27 | 4-[4-[4-(2,6-bis(1-pyrrolidinyl)-4-pyrimidinyl)-1-piperazinyl]butoxy]phenol (I/A-22) |
| 28 | 4-[5-[4-(2,6-bis(1-pyrrolidinyl)-4-pyrimidinyl)-1-piperazinyl]pentoxy]phenol (I/A-22) |
| 29 | 4-[4-[4-(2,6-bis(2-pyridinyl)-4-pyrimidinyl)-1-piperazinyl]butoxy]phenol (I/A-51) |
| 30 | 4-[6-[4-(2,6-bis(1-pyrrolidinyl)-4-pyrimidinyl)-1-piperazinyl]hexyloxy]phenol (I/A-22) |
| 31 | 4-[6-[4-[3-(ethylamino)-2-pyridinyl]-1-piperazinyl]hexyloxy]phenol (I/A-47) |
| 32 | 4-[6-[4-(3,6-bis(2-pyridinyl)-4-pyridazinyl)methyl-1-piperazinyl]hexyloxy]phenol (I/A-52) |
| 33 | 4-[6-[4-(2,6-bis(2-pyridinyl)-4-pyrimidinyl)-1-piperazinyl]hexyloxy]phenol (I/A-51) |
| 34 | 4-[6-[4-(2,6-bis(2-pyridinyl)-4-pyrimidinyl)-1-piperazinyl]hexyloxy]anisole (I/A-51) |
| 35 | 5-[3-(4-(2,6-bis(1-pyrrolidinyl)pyrimidin-4-yl)piperazin-1-yl)propyl]benzodioxole (I/A-22) |
| 36 | 5-[3-((N-ethylaminopyridin-2-yl)piperazin-1-yl)propyl]-benzodioxole (I/A-47) |
| 37 | 1,2-methylenedioxy-4-[(3-[1-piperazinyl-(4-(2-morpholino-6-methoxypyrimidinyl))]propyl]benzene (I/A-56) |
| 38 | 2-[4-2,6-bis(1-pyrrolidinyl)-4-pyrimidinyl-1-piperazinyl]-4-methoxyphenylethane |
| 39 | 1-Phenyl-3-[4-(2,6-bis(1-pyrrolidinyl)-4-pyrimidinyl)-1-piperazinyl]-propane (I/A-22) |

EXAMPLE 40

4-[2-[4-(2,6-Bis(1-pyrrolidinyl)-4-pyrimidinyl)-1-piperazinyl]ethoxy]phenol ((I/A-22)

To a stirred solution of oxalyl chloride (2.0 ml) and dichloromethane (20 ml), previously cooled to −78° in a dry ice/acetone bath, is added dropwise over 5 min a solution of DMSO (3.4 ml) and methylene chloride (5 ml). The mixture is stirred at −78° for 5 min and then allowed to warm to 0° in an ice bath. To the mixture is added dropwise a solution of 4-(2-hydroxyethoxy)-phenol (1.54 g) in methylene chloride (15 ml) over 10-15 min. The mixture is stirred at 0° for 30 min, triethyl amine (7 ml) is added dropwise and the mixture allowed to warm to 20°-25°. The mixture is diluted with methylene chloride (25 ml) and washed with hydrochloric acid (5%, 50 ml), twice with water (50 ml), dried over sodium sulfate and the solvent removed at reduced pressure to leave an oil that is flash chromatographed on silica gel (25 g) eluting with ethyl acetate/hexane (33/67) to give 4-hydoxyphenylacetaldehyde which is carried on immediately by the addition of 2,6-bis(1-pyrrolidinyl)-4-(1-piperazinyl)pyrimidine (PREPARATION A-22, 0.79 g) and methanol (10 ml). To the mixture is added sodium cyanoborohydride (0.16 g) and the mixture is stirred at 20°-25° for 18 hr. The mixture is treated with aqueous hydrochloric acid (10%, 10 ml) HCl at 0° and the methanol removed at reduced pressure. The residue is distributed between ethyl acetate (50 ml) and water (40 ml). The aqueous phase is brought to pH 8 with aqueous potassium hydroxide (45%) at 0° and then extracted methylene chloride (2×50 ml). The combined extracts are dried over sodium sulfate and the solvent removed at reduced pressure to give a foam that is flash chromatographed on silica gel (35 g) eluting with hexane/ethyl acetate (33/67) to give the title compound.

EXAMPLE 41

1-[2-(4-Methoxy-3,5-dimethylphenyl)-2-hydroxypropyl]-4-[2,6-bis(1-pyrrolidinyl)-4-pyrimidinyl]piperazine (I/A-22)

A mixture of chloroacetone (1.00 g), 2,6-bis(1-pyrrolidino)-4-(1-piperazinyl)pyrimidine (PREPARATION A-22, 3.02 g) and potassium carbonate (1.32 g) is stirred in acetonitrile (50 ml) for 24 hr. The reaction mixture is partitioned between methylene chloride and aqueous sodium bicarbonate. The organic phase is dried over sodium sulfate and concentrated. The residue is chromatographed over silica gel eluting with 2-3% methanol/methylene chloride to give the methyl ketone derivative of 2,4-bis(1-pyrrolidino)-4-(1-piperazinyl)-pyrimidine which had a consistent NMR.

A mixture of 2,6-dimethyl-4-bromoanisole (1.62 g) and powdered magnesium (181 mg) is refluxed for 6 hr in dry THF (20 ml). This mixture is added to a solution of the methyl ketone derivative in dry THF (20 ml). The mixture is stirred at 35° for 18 hr. The reaction mixture is partitioned between methylene chloride and aqueous sodium bicarbonate. The organic phase is dried over sodium sulfate and concentrated. The residue is chromatographed over silica gel, eluting with 2-3% methanol/methylene chloride to give the title compound.

EXAMPLE 42

1-[4-(4-Methoxy-3,5-dimethylphenyl)butyl)]-4-(2,6-bis(1-pyrrolidinyl))pyrimidin-4-yl)piperazine (I/A-22)

A solution of 4-[3,5-dimethyl-4-methoxyphenyl)-]butanol (600 mg), methanesulfonyl chloride (490 mg) and triethylamine (460 mg) in methylene chloride is stirred at 0° for 1 hr. The reaction mixture is partitioned between methylene chloride and aqueous sodium bicarbonate. The organic phase is dried over sodium sulfate and concentrated. The residue is dissolved in acetonitrile (60 ml) and treated with 2,4-bis(1-pyrrolidino)-4-(1-piperazinyl)pyrimidine (PREPARATION A-22, 1.73 g) and potassium carbonate (0.57 g). The reaction is run overnight at 20°-25° and then at 50° for 3 hr. The reaction mixture is partitioned between methylene chloride and aqueous sodium bicarbonate. The organic phase is dried over sodium sulfate and concentrated. The residue is chromatographed over silica gel, eluting with methanol/methylene chloride (4/96) to give an oil.

EXAMPLE 42A

1-[4-(4-Methoxy-3,5-dimethylphenyl)butyl)]-4-(bis(1-pyrrolidinyl))pyrimidin-4-yl)piperazine methane sulfonate 1-[4-(4-Methoxy-3,5-dimethylphenyl)butyl)]-4-(2,6-bis(1-pyrrolidinyl)-4-pyrimidinyl)piperazine (EXAMPLE 42) is treated with methanesulfonic acid (180 mg) in THF to give the title compound.

EXAMPLE 42'

1-[4-(4-Methoxy-3,5-dimethylphenyl)butyl)]-4-bis(1-pyrrolidinyl))pyrimidin-4-yl)piperazine 4-[3,5-Dimethyl-4-methoxyphenyl)]-butanol (1.26 g) is treated with methanesulfonyl chloride (0.57 ml) and triethylamine (0.73 g) in methylene chloride (15 ml) at 0°. The mixture is partitioned between cold water and methylene chloride. The organic phase is dried over sodium sulfate and concentrated. The residue is stirred with 2,4-bis(1-pyrrolidino)-4-(1-piperazinyl)pyrimidine (PREPARATION A-22, 2.00 g), potassium carbonate (0.960 mg) and potassium iodide (400 mg) in acetonitrile (20 ml) for 20 hr. The reaction mixture is partitioned between methylene chloride and aqueous sodium bicarbonate. The organic phase is dried over sodium sulfate and concentrated. The residue is chromatographed over silica gel, eluting with methanol/methylene chloride (2/98) to give the title compound which crystallized on standing.

EXAMPLE 42B

1-[4-(4-Methoxy-3,5-dimethylphenyl)butyl)]-4-(bis(1-pyrrolidinyl))pyrimidin-4-yl)piperazine dihydrochloride 1-[4-(4-Methoxy-3,5-dimethylphenyl)butyl)]-4-(bis(1-pyrrolidinyl))pyrimidin-4-yl)piperazine (EXAMPLE 42') is dissolved in acetone and treated in excess with ether which was saturated with hydrogen chloride gas. The salt is filtered, triturated with ether and dried under reduce pressure to give the title compound.

EXAMPLE 43

2-[4-(4-(3,5-Dimethyl-4-methoxyphenyl)butyl)piperazin-1-yl]-N-ethyl-3-pyridineamine ((I/A-47)

Following the general procedure of EXAMPLE 42' and making non-critical variations but starting with 4-[3-(ethylamino))-2-pyridinyl]piperazine (PREPARATION A-47, 1.00 g) the title compound is obtained.

EXAMPLE 43A

2-[4-(4-(3,5-Dimethyl-4-methoxyphenyl)butyl)piperazin-1-yl]-N-ethyl-3-pyridineamine dihydrochloride 2-[4-(4-(3,5-Dimethyl-4-methoxyphenyl)butyl)piperazin-1-yl]-N-ethyl-3-pyridineamine (EXAMPLE 43) is dissolved in ether/acetone and treated in excess with ether which was saturated with hydrogen chloride gas. The salt is filtered, dried under reduced pressure to give the title compound.

EXAMPLE 44

2-[4-(4-(3,5-Dimethyl-4-hydroxyphenyl)butyl)piperazin-1-yl]-N-ethyl-3-pyridineamine (I/A-47)

4-[2,6-Dimethyl-1-hydroxy-4-phenyl]butanol (PREPARATION NA-15, 4.22 g) in acetonitrile (50 ml) is treated with 4-[3-(ethylamino))-2-pyridinyl]-piperazine (PREPARATION A-47, 2.68 g), potassium carbonate (1.72 g) and potassium iodide (0.8 g). The reaction is heated at 50° for 20 hr. The reaction mixture is partitioned between methylene chloride and aqueous sodium bicarbonate. The organic phase is dried over sodium sulfate and concentrated. The residue is chromatographed over silica gel, eluting with methanol/methylene chloride (3/97) to give the phenol O-mesylate alkylation product. The O-mesylate is hydroylzed with sodium hydroxide (50%, 11 ml) in methanol (60 ml) heated at 50° for 10 hr. (Potassium carbonate, methanol and water does not hydrolyze the O-mesylate). The mixture is made acidic with hydrochloric acid and then neutralized with aqueous sodium bicarbonate. The mixture is extracted with methylene chloride. The organic phase is dried over sodium sulfate and concentrated to give the title compound which had a consistent NMR.

EXAMPLE 44A

2-[4-(4-(3,5-Dimethyl-4-hydroxyphenyl)butyl)piperazin-1-yl]-N-ethyl-3-pyridineamine dihydrochloride 2-[4-(4-(3,5-Dimethyl-4-hydroxyphenyl)butyl)piperazin-1-yl]-N-ethyl-3-pyridineamine (EXAMPLE 44) Is dissolved in ethyl acetate and treated in excess with ether which was saturated with hydrogen chloride gas. The salt is filtered and dried under reduced pressure to give the title compound.

EXAMPLE 45

1-[4-(4-Hydroxy-3,5-dimethylphenyl)butyl)]-4-(di(1-pyrrolidinyl))pyrimidin-4-yl)piperazine (I/A-22)

Following the general procedure of EXAMPLE 44 and making non-critical variations but starting with 2,4-bis(1-pyrrolidino)-4-(1-piperazinyl)pyrimidine (PREPARATION A-22, 3.93 g), the title compound is obtained.

EXAMPLE 45A

1-[4-(4-Hydroxy-3,5-dimethylphenyl)butyl)]-4-(di-(1-pyrrolidinyl))pyrimidin-4-yl)piperazine dihydro chloride 1-[4-(4-Hydroxy-3,5-dimethylphenyl)butyl)]-4-(di(1-pyrrolidinyl))pyrimidin-4-yl)piperazine (EXAMPLE 45) is dissolved in ethyl acetate and treated in excess with ether which is saturated with hydrogen chloride gas. The salt is filtered and dried under reduced pressure to give the title compound.

EXAMPLE 46

1-(4-Methoxyphenoxy)-6-[3,6-bis(2-pyridinyl)-4-pyridazinyl]-hexane (I/A-55)

Following the general procedure of EXAMPLE 17 and making non-critical variations but starting with 8-(4-methoxyphenoxy)-1-octyne (PREPARATION NA-18), the title compound is obtained.

EXAMPLE 47

2,6-Dimethyl-4-[3-(2,4-bis(1-pyrrolidinyl)-6-pyrimidinyl)piperazinyl)propyl phenol (I/A-22)

Part-I 2,6-Dimethyl-4-[3-(2,4-bis(1-pyrrolidinyl)-6-pyrimidinyl)piperazinyl)propylphenol O-mesylate A mixture of 3-(3,5-Dimethyl-4-hydroxyphenol)-propanol bismesylate (PREPARATION NA-19, 1.1 g), potassium iodide, powdered potassium carbonate (1.38 g) and 2,4-bis(1-pyrrolidinyl)-4-(1-piperazinyl)pyrimidine (PREPARATION A-22, 1.61 g) in acetonitrile (50 ml) is refluxed for 72 hr. The mixture is cooled and diluted with water and methylene chloride. The phases are separated and the organic phase is washed with water, dried over sodium sulfate and concentrated. The concentrate is flash chromatographed on silica gel (230-400 mesh) eluting with methanol/chloroform (2.5/97.5). The appropriate fractions are pooled to give the mesylate.

Part-II 2,6-Dimethyl-4-[3-(2,4-bis(1-pyrrolidinyl)-6-pyrimidinyl)piperazinyl)propylphenol 2,6-Dimethyl-4-[3-(2,4-bis(1-pyrrolidinyl)-6-pyrimidinyl)piperazinyl)propyl phenol O-mesylate (Part I, 1.0 g) in aqueous sodium hydroxide (25%, 10 ml) and methanol (20 ml) are stirred at 50° under nitrogen for 20 hr. The mixture is cooled and the methanol removed under reduced pressure. The aqueous layer is acidified with aqueous hydrochloric acid (10%) and then the pH adjusted to 8 with aqueous saturated sodium bicarbonate. The product is extracted with methylene chloride (2×). The extracts are washed with water, dried over sodium sulfate and concentrated. The concentrate is crystallized from ether/hexane to give the title compound.

EXAMPLE 47A 2,6-Dimethyl-4-[3-(2,4-bis(1-pyrrolidinyl)-6-pyrimidinyl)piperazinyl)propylphenol 0.25 hydrate

EXAMPLE 48

4-[3-(4-(3-(N-Ethylamino)pyridin-2-yl)piperazin-1-yl)propyl]-2,6-dimethylphenol (I/A-47)

Following the general procedure of EXAMPLE 47 (parts I and II) and making non-critical variations but using 4-[3-(ethylamino))-2-pyridinyl]-piperazine (PREPARATION A-47), the title compound is obtained.

EXAMPLE 49

2,6-Bis(1-pyrrolidinyl)-4-[4-(3-(3,5-dimethyl-4-methoxyphenyl)propyl)piperazinyl]pyrimidine (I/A-22)

Following the general procedures of PREPARATION NA-19 Part-II (but using only 1 equivalent of mesylate) and EXAMPLE 47 Part-I and making non-critical variations but starting with 3-(3,5-dimethyl-4-methoxyphenyl)-1-propanol (PREPARATION NA-20) and 2,4-bis(1-pyrrolidino)-4-(1-piperazinyl)pyrimidine (PREPARATION A-22), the title compound is obtained.

EXAMPLE 50

N-Ethyl-2-[4-[3-(4-methoxy-3,5-dimethylphenyl)-propyl]-1-piperazinyl]-3-pyridinamine (I/A-47)

Following the general procedures of EXAMPLE 49 and making non-critical variations but starting with 4-[3-(ethylamino))-2-pyridinyl]-piperazine (PREPARATION A-47), the title compound is obtained.

EXAMPLE 51

4-[2-[4-(2,6-Bis(1-pyrrolidinyl)-4-pyrimidinyl-1-piperazinyl]ethyl]-2,6-dimethylphenol (I/A-22)

Following the general procedure of PREPARATION NA-19 Part-II and EXAMPLE 47 but starting with 2-(3,5-dimethyl-4-hydroxyphenyl)-1-ethanol (PREPARATION NA-21) and 2,4-bis(1-pyrrolidino)-4-(1-piperazinyl)pyrimidine (PREPARATION A-22), the title compound is obtained.

EXAMPLE 52

4-[2-[4-[3-(Ethylamino)-2-pyridinyl]-1-piperazinyl]ethyl]-2,6-dimethylphenol (I/A-47)

Following the general procedure of PREPARATION NA-19 Part-II and EXAMPLE 47 but starting with 2-(3,5-dimethyl-4-hydroxyphenyl)-1-ethanol (PREPARATION NA-21) and 4-[3-(ethylamino))-2-pyridinyl]-piperazine (PREPARATION A-47), the title compound is obtained.

EXAMPLE 53

4-[4-[2-(3,4-Dihydro-6,7-dimethoxy-1H-2-benzopyran-1-yl)ethyl]-1-piperazinyl]-2,6-di-1-pyrrolidinyl-pyrimidine (V/A-22)

A solution of 6,7-dimethoxy-1-[2-chloroethyl]isochroman (2.58 g), 2,4-bis(1-pyrrolidino)-4-(1-piperazinyl)pyrimidine (PREPARATION A-22, 3.02 g), potassium carbonate (1.32 g) and potassium iodide (0.88 g) in dry acetonitrile (40 ml) is stirred at 50° for 20 hr. The reaction mixture is partitioned between methylene chloride and aqueous sodium bicarbonate. The organic phase is dried over sodium sulfate and concentrated. The residue is chromatographed over silica gel eluting with methanol/methylene chloride (3/97) to give the title compound.

EXAMPLE 54

2,4-Bis-(1-pyrrolidinyl)-6-[4-[2-[2-[(1,3,4,5-tetrahydro-7,8-dimethoxy-2-benzoxepin-1-yl)methoxy]ethoxy]ethyl]-1-piperazinyl]pyrimidine (V/A-22)

Following the gereral procedure of EXAMPLE 53 and making non-critical variations but using 7,8-dimethoxy-1-[CH$_2$—O—CH$_2$CH$_2$—O—CH$_2$CH$_2$Cl]benzoxepine (250 mg), the title compound is obtained.

EXAMPLE 55

4-[3-Ethylamino-2-pyridinyl]-1-[2-[6,7-dimethoxyisochromyl]eth-1-yl]piperazine (V/A-47)

Following the general procedure of EXAMPLE 53 and making non-critical variations but starting with 4-[3-(ethylamino))-2-pyridinyl]-piperazine (PREPARATION A-47), the title compound is obtained.

EXAMPLE 56

4-[4-[2-(4-Methoxy-3,5-dimethylphenyl)ethyl]-1-piperazinyl]-2,6-bis(1-pyrrolidinyl)pyrimidine (I/A-22)

Following the general procedures of EXAMPLE 49 and making non-critical variations but starting with 2-(3,5-dimethyl-4-methoxyphenyl)-1-ethanol (PREPARATION NA-22) and 2,4-bis(1-pyrrolidino)-4-(1-piperazinyl)pyrimidine (PREPARATION A-22), the title compound is obtained.

EXAMPLE 57

N-Ethyl-2-[4-[2-(4-methoxy-3,5-dimethylphenyl)ethyl]-1-piperazinyl]-3-pyridinamine (I/A-47)

Following the general procedures of EXAMPLE 49 and making non-critical variations but starting with 2-(3,5-dimethyl-4-methoxyphenyl)-1-ethanol (PREPARATION NA-22) and 4-[3-(ethylamino))-2-pyridinyl]-piperazine (PREPARATION A-47), the title compound is obtained.

EXAMPLE 58

2,6-Bis(1-pyrrolidinyl)-4-[4-[6-(3,5-dimethyl-4-methoxyphenyl)hexyl]-1-piperazinyl]pyrimidine (I/A-22)

Following the general procedure of EXAMPLE 47-Part I and making non-critical variations but starting with 6-(3,5-dimethyl-4-methoxyphenyl)-1-hexanol mesylate (PREPARATION NA-23) and 2,4-bis(1-pyrrolidino)-4-(1-piperazinyl)pyrimidine (PREPARATION A-22), the title compound is obtained.

EXAMPLE 59

2-[4-[6-(3,5-dimethyl-4-methoxyphenyl)hexyl]-1-piperazinyl-N-ethyl-3-pyridinamine ((I/A-47)

Following the general procedure of EXAMPLE 47-Part I and making non-critical variations but starting with 6-(3,5-dimethyl-4-methoxyphenyl)-1-hexanol mesylate (PREPARATION NA-23) and 4-[3-(ethylamino))-2-pyridinyl]-piperazine (PREPARATION A-47), the title compound is obtained.

EXAMPLE 60

3-[6-(4-(3-(Ethylamino)pyridin-2-yl)piperazin-1-yl)hexyl]cyclohex-2-en-1-one (IV/A-47)

Following the procedure of Borch, J. Am. Chem. Soc., 93, 2897 (1971), sodium cyanoborohydride (144 mg) is added to a solution of 3-oxo-1-cyclohexanal (PREPARATION NA-25, 405 mg), 4-[3-(ethylamino))-2-pyridinyl]-piperazine (PREPARATION A-47, 495 mg) and methanol (4.20 ml). After stirring for 16 hr at 20°-25°, acetic acid (2 drops) and sodium cyanoborohydride (40 mg) are added. After 3 hr, concentration, basic workup with chloroform and aqueous sodium bicarbonate and purification by flash chromatography eluting with ethyl acetate/triethylamie (99/1) provides the title compound.

EXAMPLES 61-64

See CHART E for Column A and Column B.

Following the general procedure of EXAMPLE 60 and making non-critical variations but using the nonamine (NA-#) of Column A and the amine (A-#) of Column B, the corresponding cycloalkyl amine (IV) of Column C is obtained:

| EXAMPLE | Column C Cycloalkyl amine (IV) |
|---|---|
| 61 | 3-[6-((2,6-bispyrrolidin-1-yl)pyrimidin-4-yl)piperazin-1-yl)hexyl]cyclohex-2-en-1-one (IV/A-22) |
| 62 | 3-[4-(4-(3-(ethylamino)pyrid-2-yl)piperazin-1-yl)butyl]-cyclohex-2-en-1-one (IV/A-47) |
| 63 | 3-[3-(4-(3-(ethylamino)pyrid-2-yl)piperazin-1-yl)propyl]-cyclohex-2-en-1-one (IV/A-47) |
| 64 | 3-[3-(4-(2,6-bis(1-pyrrolidinyl)pyrimidin-4-yl)piperazin-1-yl)propyl]-cyclohex-2-en-1-one (IV/A-22) |

EXAMPLE 65

1-Phenoxy-4-[4-(2,6-bis(1-pyrrolidinyl)-4-pyrimidinyl)-1-piperazinyl]-butane (I/A-22)

Following the general procedure of EXAMPLE 1 and making non-critical variations but using 4-phenoxy-1-bromobutane (PREPARATION NA-27) and 2,4-bis(1-pyrrolidino)-4-(1-piperazinyl)pyrimidine (PREPARATION A-22), the title compound is obtained.

EXAMPLE 66

1-[(3,4-Dihydro-6-hydroxy-2,5,7,8-tetramethyl-2H-1-benzopyran-2-yl)acetyl]-4-(2,6-bis(1-pyrrolidinyl)-4-pyrimidinyl)-piperazine (III/A-22)

Following the general procedure of EXAMPLE 18 and making non-critical variations but starting with (6-hydroxy-2,5,7,8-tetramethylchroman-2-yl)acetic acid, the title compound is obtained.

EXAMPLE 67

1-[3,4-Dihydro-6-hydroxy-2,5,7,8-tetramethyl-2H-1-benzopyran-2-yl)ethyl]-4-(2,6-bis(1-pyrrolidinyl)-4-pyrimidinyl)-piperazine (III/A-22)

Following the general procedure of EXAMPLE 21 and making non-critical variations but starting with 1-[3,4-dihydro-6-hydroxy-2,5,7,8-tetramethyl-2H-1-benzopyran-2-yl)acetyl]-4-(2,6-bis(1-pyrrolidinyl)-4-pyrimidinyl)-piperazine (EXAMPLE 66), the title compound is obtained.

EXAMPLE 68

1-[[6-(Acetyloxy)-3,4-dihydro-2,5,7,8-tetramethyl-2H-1-benzopyran-2-yl]acetyl]-4-[3-(ethylamino)-2-pyridinyl]-piperazine (III/A-47)

An etheral solution of (6-acetoxy-2,5,7,8-tetramethylchroman-2-yl)acetyl chloride (10 ml, 1.3 g) is added slowly to a stirred solution of 4-[3-(ethylamino))-2-pyridinyl]-piperazine (PREPARATION A-47, 0.81 g) in chloroform (70 ml). The mixture is stirred 2 hr and then is washed with aqueous potassium bicarbonate and saline. The organic extracts are dried over magnesium sulfate and concentrated to give the title compound.

EXAMPLE 69

2,6-Bis(1,1-dimethylethyl)-4-[[4-(2,6-bis-1-pyrrolidinyl-4-pyrimidinyl)-1-piperazinyl]methyl]phenol (I/A-22)

2,6-bis(1-pyrrolidinyl)-4-(1-piperazinyl)pyrimidine (PREPARATION A-22) is stirred in methanol (10 ml). To the above solution is added saturated ethereal hydrochloric acid until the solution clarifies. To this mixture is added 3,5-di-t-butyl-4-hydroxybenzaldehyde and the mixture stirred for 30 min at which time sodium cyanoborohydride is added in two batches. The mixture is stirred at 20°-25° for 18 hr and quenched with hydrochoric acid (10%, 25 ml) added dropwise at 0°. The methanol is removed under a stream of nitrogen and the acidic mixture is extracted with ethyl acetate (25 ml). The aqueous phase is then made basic with hydroxide (45%) at 0°. The aqueous basic phase is then extracted with methylene chloride (2 ×). The organic phases are combined and dried over sodium sulfate, following which the mixture is concentrated under at reduced pressure. The concentrate is flashed chromatographed on silica gel eluting with hexane/ethyl acetate (1/1) or ethyl acetate. The appropriate fractions are pooled and concentrated to give the title compound.

EXAMPLES 70-72

Following the general procedure of EXAMPLE 69 and making non-critical variations but starting with 4-(2-pyridinyl)piperazine (PREPARATION A-6, for EXAMPLE 70), 4-(ethanol)piperazine (for EXAMPLE 71) and 4-[3-(ethylamino)-2-pyridinyl]piperazine (PREPARATION A-47, for EXAMPLE 72), compounds listed below are obtained:

| EXAMPLE | Compound |
|---|---|
| 70 | 2,6-bis(1,1-dimethylethyl)-4-[[4-(2-pyridinyl)-1-piperazinyl]methyl]phenol (I/A-6) |
| 71 | 4-[[3,5-Bis(1,1-dimethylethyl)-4-hydroxyphenyl]methyl]-1-piperazineethanol (1) |
| 72 | 2,6-bis(1,1-dimethylethyl)-4-[[4-(3-ethylamino)-2-pyridinyl]-1-piperazinyl]methyl]phenol (I/A-47) |

EXAMPLE 73

4-(2,6-Bis(1-pyrrolidinyl)-4-pyrimidinyl)-N-(4-hydroxy-3,5-dimethylphenyl)-1-piperazineacetamide (I/A-22)

To 2,6-dimethyl-4-aminophenol hydrogen chloride (5.0 g) in methylene chloride (20 ml) is added triethylamine (6.5 g) in methylene chloride (20 ml) dropwise at 0°. To the cold solution is added chloroacetylchloride (3.6 g) in methylene chloride (20 ml) dropwise over 5-10 m. The mixture is stirred at 0° for 30 min and then at 20°-25° for 1 hr. The mixture is washed with water (60 ml), dried over sodium sulfate and the solvent removed at reduced pressure to give a solid. MS (EI, m/e)=213, 215 (M+). Acetonitrile (40 ml), 2,6-bis(1-pyrrolidinyl)-4-(1-piperazinyl)pyrimidine (PREPARATION A-22, 1.42 g), potassium carbonate (0.65 g) are added to the solid and the mixture is heated at reflux for 10 hr. The solvent is removed at reduced pressure and residue is distributed between chloroform (100 ml) and water (100 ml). The phases are separated and the organic phase is dried over sodium sulfate and the solvent is removed at reduced pressure to give an oil. The oil is flash chromatographed on silica gel (175 g) eluting with ethyl acetate/hexane (2/1). The appropriate fractions were pooled and concentrated to give the title compound.

EXAMPLE 74

4-[4-(6-(4-Methoxy-1-thio)hexylphenyl)-1-piperazinyl]-2,6-bis(1-pyrrolidinyl)pyrimidine (I/A-22)

A mixture of thioanisole (0.88 ml), 6-chlorohexanol (1.07 g), potassium carbonate (1.08 g) and acetone (10 ml) is heated at reflux for 18 hr. The solvent is removed at reduced pressure and the residue distribute between methylene chloride (50 ml) and water (50 ml). The phases are separated, the organic phase is dried over sodium sulfate, the solvent removed at reduced pressure to leave an oil that crystallizes from hexane. The crystalline material is dissolved in a mixture of chloroform (10 ml) and pyridine (0.66 g) and cooled to 0°. To the mixture is added dropwise over 3-5 min a solution of p-toluenesulfonylchloride (1.2 g) in chloroform (5 ml). The mixture is stirred at 0° for 1 hr then at 20°-25° for 18 hr. The reaction mixture is washed with hydrochloric acid (0.1N), saline, dried over sodium sulfate and the solvent removed at reduced pressure to give the crude tosylate. To the crude tosylate is added 2,6-bis(1-pyrrolidinyl)-4-(1-piperazinyl)pyrimidine (PREPARATION A-22, 1.4 g), potassium carbonate (1.28 g) and acetonitrile (25 ml). The mixture is heated at reflux for 18 hr. The solvent is removed at reduced pressure and the residue distributed between chloroform (50 ml) and water (50 ml). The phases are separated, the organic phase is dried over sodium sulfate and the solvent removed to leave an oil that is flash chromatographed on silica gel (100 g) eluting with ethyl acetate. The appropriate fractions are pooled and concentrated. The concentrate is crystallized from ethyl acetate to give the title compound.

EXAMPLE 75

1-[[6-(Hydroxy)-3,4-dihydro-2,5,7,8-tetramethyl-2H-1-benzopyran-2-yl]acetyl]-4-[3-(ethylamino)-2-pyridinyl]-piperazine (III/A-47)

A solution of 1-[[6-(acetyloxy)-3,4-dihydro-2,5,7,8-tetramethyl-2H-1-benzopyran-2-yl]acetyl]-4-[3-(ethylamino)-2-pyridinyl]-piperazine (EXAMPLE 68, 0.80 g) in methanol (20 ml) is mixed with potassium carbonate (10% aqueous, 1.5 ml) and stirred for 3.5 hr at 20°-25° under a nitrogen atmosphere. Then acetic acid (0.2 ml) is added and the solution is concentrated. The residue is partitioned between methylene chloride and potassium bicarbonate (1N). The organic extracts are combined and washed with water, dried over magnesium sulfate and concentrated to give the title compound.

EXAMPLE 77

2,6-Bis(1-pyrrolidinyl)-4-[4-((2-(3,5-dimethyl-4-methoxyphenyl)-2-(4-methoxyphenyl)-2-hydroxyethyl)-piperazinylpyrimidine (I/A-22)

1-[[(4-Methoxyphenyl)-2-ketoeth-1-yl]butyl]-4-(bis(1-pyrrolidinyl))pyrimidin-4-yl)piperazine (EXAMPLE 38) is dissolved in dry THF and is reacted with a Grignard reagent which is prepared from 2,6-dimethyl-4-bromoanisole and magnesium. The reaction mixture is partitioned between methylene chloride and aqueous sodium bicarbonate. The organic phase is dried over sodium sulfate and concentrated. The residue is chromatographed over silica gel eluting with methanol/methylene chloride (3/97) to give the title compound.

EXAMPLES 78-99

Following the general procedure of EXAMPLE 18 and the description of the general procedure in the specification to prepare the amide type bicyclic amines (III) where $X_3$ is —CO—, the following compounds are obtained:

| Example | Bicyclic amine (III) |
|---|---|
| 78 | 1-[5,6-Bis(diethylamino)-2-pyridinyl]-4-[(3,4-dihydro-6-hydroxy-2,5,7,8-tetramethyl)-2H-1-benzopyran-2-yl)carbonyl]piperazine |
| 79 | 1-[(3,4-Dihydro-6-hydroxy-2,5,7,8-tetramethyl-2H-1-benzopyran-2-yl)carbonyl]-4-(2-methoxyphenyl)piperazine |
| 80 | 1-[(3,4-Dihydro-6-hydroxy-2,5,7,8-tetramethyl-2H-1-benzopyran-2-yl)carbonyl]-4-(2-pyridinyl)piperazine |
| 81 | 1-[(3,4-Dihydro-6-hydroxy-2,5,7,8-tetramethyl-2H-1-benzopyran-2-yl)carbonyl]-4-(2-pyrimidinyl)piperazine |
| 82 | 1-(3-Chlorophenyl)-4-[(3,4-dihydro-6-hydroxy-2,5,7,8-tetramethyl-2H-1-benzopyran-2-yl)carbonyl]piperazine |
| 83 | 1-(1,3-Benzodioxol-5-ylmethyl)-4-[(3,4-dihydro-6-hydroxy-2,5,7,8-tetramethyl-2H-1-benzopyran-2-yl)carbonyl]piperazine |
| 84 | 1-[(4-Chlorophenyl)phenylmethyl]-4-[(3,4-dihydro-6-hydroxy-2,5,7,8-tetramethyl-2H-1-benzopyran-2-yl)carbonyl]piperazine |
| 85 | 1-(4-Chlorophenyl)-4-[(3,4-dihydro-6-hydroxy-2,5,7,8-tetramethyl-2H-1-benzopyran-2-yl)carbonyl]piperazine |
| 86 | 1-[(3,4-Dihydro-6-hydroxy-2,5,7,8-tetramethyl-2H-1-benzopyran-2-yl)carbonyl]-4-(4-methoxyphenyl)piperazine |
| 87 | N-[2-(3,4-Dimethoxyphenyl)ethyl]-3,4-dihydro-6-hydroxy-2,5,7,8-tetramethyl-2H-1-benzopyran-2-carboxamide |
| 88 | 3,4-dihydro-2,5,7,8-tetramethyl-2-(1-piperazinylcarbonyl)-2H-1-benzopyran-6-ol |
| 89 | N-(2-Pyridinylmethyl)-3,4-dihydro-6-hydroxy-2,5,7,8-tetramethyl-2H-1-benzopyran-2-carboxamide |
| 90 | N-[2-(4-Aminophenyl)ethyl]-3,4-dihydro-6-hydroxy-2,5,7,8-tetramethyl-2H-1-benzopyran-2-carboxamide |
| 91 | N-[3,4-Methylenedioxophenylmethyl]-3,4-dihydro-6-hydroxy-2,5,7,8-tetramethyl-2H-1-benzopyran-2-carboxamide |
| 92 | N-[2-(2-Pyridinyl)ethyl]-3,4-dihydro-6-hydroxy-2,5,7,8-tetramethyl-2H-1-benzopyran-2-carboxamide |

-continued

| Example | Bicyclic amine (III) |
|---|---|
| 93 | N-Methyl-N-[[2-(2-pyridinyl)ethyl]-3,4-dihydro-6-hydroxy-2,5,7,8-tetramethyl]-2H-1-benzopyran-2-carboxamide |
| 94 | N-(3-Pyridinylmethyl)-3,4-dihydro-6-hydroxy-2,5,7,8-tetramethyl-2H-1-benzopyran-2-carboxamide |
| 95 | 1-[3,4-Dihydro-6-hydroxy-2,5,7,8-tetramethyl-2H-1-benzopyran-2-yl)carbonyl]-4-(phenylmethyl)piperazine |
| 96 | 1-[3,4-Dihydro-6-hydroxy-2,5,7,8-tetramethyl-2H-1-benzopyran-2-yl)carbonyl]-4-phenylpiperazine |
| 97 | N-[2-(Dimethylamino)ethyl]-3,4-dihydro-6-hydroxy-2,5,7,8-tetramethyl-2H-1-benzopyran-2-carboxamide, m.p. 127-128° |
| 98 | 3,4-Dihydro-2,5,7,8-tetramethyl-2-(1-pyrrolidinylcarbonyl)-2H-1-benzopyran-6-ol |
| 99 | N-[2-(Phenylethyl)]-N-[2-(2-pyridinylethyl)]-3,4-dihydro-6-hydroxy-2,5,7,8-tetramethyl-2H-1-benzopyran-2-carboxamide |
| 100 | 1-[3-Diethylamino-2-pyridinyl]-4-[(3,4-dihydro-6-hydroxy-2,5,7,8-tetramethyl)-2H-1-benzopyran-2-yl)carbonyl]piperazine |
| 101 | 1-[5-Diethylamino-2-pyridinyl]-4-[(3,4-dihydro-6-hydroxy-2,5,7,8-tetramethyl)-2H-1-benzopyran-2-yl)carbonyl]piperazine |
| 102 | N-[2-Pyridinyl]-3,4-dihydro-6-hydroxy-2,5,7,8-tetramethyl-2H-1-benzopyran-2-carboxamide |
| 103 | N-[Phenyl]-3,4-dihydro-6-hydroxy-2,5,7,8-tetramethyl-2H-1-benzopyran-2-carboxamide |
| 104 | N-[4-Pyridinyl]-3,4-dihydro-6-hydroxy-2,5,7,8-tetramethyl-2H-1-benzopyran-2-carboxamide |
| 105 | N-[4-Methoxy-3-pyridinyl]-3,4-dihydro-6-hydroxy-2,5,7,8-tetramethyl-2H-1-benzopyran-2-carboxamide |
| 106 | 1-[5-Amino-6-diethylamino-4-pyrimidinyl]-4-[(3,4-dihydro-6-hydroxy-2,5,7,8-tetramethyl)-2H-1-benzopyran-2-yl)carbonyl]piperazine |
| 107 | 1-[5-Ethylamino-6-diethylamino-4-pyrimidinyl]-4-[(3,4-dihydro-6-hydroxy-2,5,7,8-tetramethyl)-2H-1-benzopyran-2-yl)carbonyl]piperazine |
| 108 | N-[4-Phenylbutyl]-3,4-dihydro-6-hydroxy-2,5,7,8-tetramethyl-2H-1-benzopyran-2-carboxamide |
| 109 | N-[3,4-Dimethoxyphenylmethyl]-3,4-dihydro-6-hydroxy-2,5,7,8-tetramethyl-2H-1-benzopyran-2-carboxamide |
| 110 | N-[3-Phenylpropyl]-3,4-dihydro-6-hydroxy-2,5,7,8-tetramethyl-2H-1-benzopyran-2-carboxamide |
| 111 | N-[2-(4-Methoxyphenyl)ethyl]-3,4-dihydro-6-hydroxy-2,5,7,8-tetramethyl-2H-1-benzopyran-2-carboxamide |
| 112 | N-[2-Phenylethyl]-3,4-dihydro-6-hydroxy-2,5,7,8-tetramethyl-2H-1-benzopyran-2-carboxamide |

EXAMPLES 113-143

Following the general procedure of EXAMPLES 21 and 23 and the description of the general procedure in the specification to prepare the reduced type bicyclic amines (III) where $X_3$ is —CH$_2$—, the following compounds are obtained:

| Example | Bicyclic amine (III) |
|---|---|
| 113 | 2-[[4-[3,6-Bis(diethylamino)-2-pyridinyl]-1-piperazinyl]-methyl]-3,4-dihydro-2,5,7,8-tetramethyl-2H-1-benzopyran-6-ol |
| 114 | 2-[[[2-(3,4-Dimethoxyphenyl)ethyl]]amino]methyl]-3,4-dihydro-2,5,7,8-tetramethyl-2H-1-benzopyran-6-ol |
| 115 | 3,4-Dihydro-2-[[4-(2-methoxyphenyl)-1-piperazinyl]methyl]-2,5,7,8-tetramethyl-2H-1-benzopyran-6-ol |
| 116 | 3,4-Dihydro-2,5,7,8-tetramethyl-2-[[4-(2-pyridinyl)-1-piperazinyl]methyl]-2H-1-benzopyran-6-ol |
| 117 | 3,4-Dihydro-2,5,7,8-tetramethyl-2-[[4-(2-pyrimidinyl)-1-piperazinyl]methyl]-2H-1-benzopyran-6-ol |
| 119 | 2-[[4-(3-Chlorophenyl)-piperazinyl]methyl]-3,4-dihydro-2,5,7,8-tetramethyl-2H-1-benzopyran-6-ol |
| 120 | 2-[[4-(1,3-Benzodioxol-5-ylmethyl)-1-piperazinyl]-3,4-dihydro-2,5,7,8-tetramethyl-2H-1-benzopyran-6-ol |
| 121 | 2-[[4-[(4-Chlorophenyl)phenylmethyl]-1-piperazinyl]methyl]-3,4-dihydro-2,5,7,8-tetramethyl-2H-1-benzopyran-6-ol |
| 122 | 2-[[4-(4-Chlorophenyl)-1-piperazinyl]methyl]-2,5,7,8-tetramethyl-2H-1-benzopyran-6-ol |
| 123 | 3,4-Dihydro-2-[[4-(4-methoxyphenyl)-1-piperazinyl]methyl]-1-piperazinyl]methyl]-2,5,7,8-tetramethyl-2H-1-benzopyran-6-ol |
| 124 | 2-[[[(3,4-Methylenedioxyphenyl)methyl]amino]methyl]-3,4-dihydro-2,5,7,8-tetramethyl-2H-1-benzopyran-6-ol |
| 125 | 3,4-Dihydro-2,5,7,8-tetramethyl-2-[[4-(phenylmethyl)-1-piperazinyl]methyl]-2H-1-benzopyran-6-ol |
| 126 | 3,4-Dihydro-2,5,7,8-tetramethyl-2-(1-piperazinylmethyl)-2H-1-benzopyran-6-ol |
| 127 | 3,4-Dihydro-2,5,7,8-tetramethyl-2-(1-pyrrolidinylmethyl)-2H-1-benzopyran-6-ol |
| 128 | 2-[[[2-(Dimethylamino)ethyl]amino]methyl]-3,4-dihydro-2,5,7,8-tetramethyl-2H-1-benzopyran-6-ol |
| 129 | 2-[[[2-(4-Aminophenyl)ethyl]amino]methyl]-3,4-dihydro-2,5,7,8-tetramethyl-2H-1-benzopyran-6-ol |
| 130 | 2-[[(4-Pyridinyl)amino]methyl]-3,4-dihydro-2,5,7,8-tetramethyl-2H-1-benzopyran-6-ol |
| 131 | 2-[[4-[(3-Diethylamino)-2-pyridinyl]-1-piperazinyl]methyl]-3,4-dihydro-2,5,7,8-tetramethyl-2H-1-benzopyran-6-ol |
| 132 | 2-[[Phenylamino)methyl]-3,4-dihydro-2,5,7,8-tetramethyl-2H-1-benzopyran-6-ol |
| 133 | 2-[[4-[5-Diethylamino-2-pyridinyl]-1-piperazinyl]methyl]-3,4-dihydro-2,5,7,8-tetramethyl-2H-1-benzopyran-6-ol |
| 134 | 2-[[2-Pyridinyl)amino]methyl]-3,4-dihydro-2,5,7,8-tetramethyl-2H-1-benzopyran-6-ol |
| 135 | 2-[[[(2-methoxy-5-pyridinyl)amino]methyl]-3,4-dihydro-2,5,7,8-tetramethyl-2H-1-benzopyran-6-ol |
| 136 | 2-[[[(2-(phenyl)ethyl]amino]methyl]-3,4-dihydro-2,5,7,8-tetramethyl-2H-1-benzopyran-6-ol |
| 137 | 2-[[[4-(phenyl)butyl]amino]methyl]-3,4-dihydro-2,5,7,8-tetramethyl-2H-1-benzopyran-6-ol |
| 138 | 2-[[[(3-(phenyl)propyl]amino]methyl]-3,4-dihydro-2,5,7,8-tetramethyl-2H-1-benzopyran-6-ol |
| 139 | 2-[[[(1-(3,4-Dimethoxyphenyl)methyl]amino]methyl]-3,4-dihydro-2,5,7,8-tetramethyl-2H-1-benzopyran-6-ol |
| 140 | 2-[[[(1-(2-Pyridinyl)methyl]amino]methyl]-3,4-dihydro-2,5,7,8-tetramethyl-2H-1-benzopyran-6-ol |
| 141 | 2-[[[(1-(3-Pyridinyl)methyl]amino]methyl]-3,4-dihydro-2,5,7,8-tetramethyl-2H-1-benzopyran-6-ol |
| 142 | 2-[[[(2-(2-Pyridinylethyl)-2-(phenyl)ethyl]amino]methyl]-3,4-dihydro-2,5,7,8-tetramethyl-2H-1-benzopyran-6-ol |
| 143 | 2-[[[(2-(2-Pyridinyl)ethyl]amino]methyl]-3,4-dihydro-2,5,7,8-tetramethyl-2H-1-benzopyran-6-ol |
| 145 | 3,4-Dihydro-2,5,7,8-tetramethyl-2[(4-phenyl-1-piperazinyl)-methyl]-2H-1-benzopyran-6-ol |
| 146 | 2-[[4-[2,6-bis(1-pyrrolidinyl)-4-pyrimidinyl]-1-piperazinyl]methyl]-3,4-dihydro-2,5,7,8-tetramethyl-2H-1-benzopyran-6-ol |
| 147 | 2-[[[(2-(2-Pyridinyl)ethyl]methylamino]methyl]-3,4-dihydro-2,5,7,8-tetramethyl-2H-1-benzopyran-6-ol |
| 148 | 2-[2-[4-[4,6-bis(1-pyrrolidinyl)-1,3,5-triazin-2-yl]-1-piperazinyl]ethyl]-3,4-dihydro-2,5,7,8-tetramethyl-2H-1-benzopyran-6-ol |

EXAMPLE 149

3,4-Dihydro-2,5,7,8-tetramethyl-2-[[4-[6-(1-pyrrolidinyl)-4-pyrimidinyl]-1-piperazinyl]methyl]-2H-benzopyran-6-ol (III)

To a stirred suspension of 3,4-dihydro-2,5,7,8-tetramethyl-2-(1-piperazinylmethyl)-2H-1-benzopyran-6-ol (EXAMPLE 126, 0.7 g), triethylamine (0.23 g, 2.3 mmol) and THF (10 ml), cooled to 0° in an ice-water bath, is added in a steady stream 4,6-dichloropyrimidine in THF (5 ml). The cooling bath is removed and the mixture stirred at 20°-25° for 18 hr. Ethyl acetate (50 ml) is added and the mixture is washed with water (50 ml), saline, dried over sodium sulfate and the solvent removed at reduced pressure to leave a residue that is dissolved in pyrrolidine (5 ml). The mixture is heated at reflux for 2 hr and concentrated at reduced pressure. The residue is flashed chromatographed on silica gel (50 g) eluting with ammonia, methanol and ethyl acetate (0.5/4.5/95) to give the product which is crystallized from hexane-ethyl acetate to give the title compound.

EXAMPLE 150

1-Benzoyl-4-[(3,4-dihydro-6-hydroxy-2,5,7,8-tetramethyl-2H-1-benzopyran-2-yl)methyl]piperazine (III)

To stirred solution of 3,4-dihydro-2,5,7,8-tetramethyl-2-(1-piperazinylmethyl)-2H-1-benzopyran-6-ol (EXAMPLE 126, 0.3 g, 1.0 mmol), triethylamine (0.11 g, 1.1 mmol) and methylene chloride (3 ml) is added dropwise over 1-2 min a solution of benzoyl chloride (0.16 g, 1.1 mmol) in methylene chloride (2 ml). The mixture is stirred at 20°-25° for 1 hr and diluted with methylene chloride (20 ml), washed with water (20 ml), dried over sodium sulfate and the solvent removed at reduced pressure to leave a residue. The residue is flashed chromatographed on silica gel (25 g) eluting with ethyl acetate/hexane (1/1) to give the product as an oil that is crystallized from ether to give the title compound.

EXAMPLE 151

2-[[4-(2,6-Bis(1-pyrrolidinyl)-4-pyrimidinyl)-1-piperazinyl]methyl]-3,4-dihydro-2,5,7,8-tetramethyl-2H-1-benzopyran-6-(1-imidazole carbamate) (III-prodrug)

A solution of 2-[[4-(2,6-bis(1-pyrrolidinyl)-4-pyrimidinyl)-1-piperazinyl]-3,4-dihydro-2,5,7,8-tetramethyl-2H-1-benzopyran-6-ol (84 mg), 1,1-carbonyldiimidazole (30 mg) and THF (1.0 ml) is heated at reflux for 16 hr. After cooling to 20°-25°, the residue is concentrated. Purification by flash chromatography hexane/ethyl acetate (1/1) provides the title compound.

EXAMPLE 152

2-[[4-(2,6-Bis(1-pyrrolidinyl)-4-pyrimidinyl)-1-piperazinyl]methyl]-3,4-dihydro-2,5,7,8-tetramethyl-2H-1-benzopyran-6-(diethylaminoacetoxy) (III-prodrug)

A solution of 2-[[4-(2,6-bis(1-pyrrolidinyl)-4-pyrimidinyl)-1-piperazinyl]methyl]-3,4-dihydro-2,5,7,8-tetramethyl-2H-1-benzopyran-6-ol (0.20 g) and THF (1.5 ml) are added to a suspension of sodium hydride (25 mg of 50% mineral oil disp, washed with hexanes) and THF (0.50 ml). The resultant solution is stirred for 1 hr at 20°-25° and is then cooled to 0° C. Chloroacetylchloride (33 μl) is added and the resultant solution is stirred for 1 hr at 0°, and 2 hr at 20°-25°. Aqueous workup (methylene chloride, magnesium sulfate) provides an oil.

The crude oil is combined with acetonitrile (2.0 ml) and diethylamine (0.10 ml) and the resultant solution stirred for 40 hr at 20°-25°. After removing solvent in vacuo, basic workup (ethyl acetate, sodium bicarbonate and magnesium sulfate) and flash chromatography, eluting with hexane/ethyl acetate (1/1) and concentrating the appropriate fractions provides the title compound.

EXAMPLE 153

2-[[4-(2,6-Bis(1-pyrrolidinyl)-4-pyrimidinyl)-1-piperazinyl]methyl]-3,4-dihydro-2,5,7,8-tetramethyl-2H-1-benzopyran-6-dimethylaminoacetoxy (III-prodrug)

Methylene chloride (4.0 ml) and pyridine (1.0 ml) are added to a solid mixture of 2-[[4-(2,6-Bis(1-pyrrolidinyl)-4-pyrimidinyl)-1-piperazinyl]methyl]-3,4-dihydro-2,5,7,8-tetramethyl-2H-1-benzopyran-6-ol (0.200 g), dimethylglycine (48 mg), dicyclohexylcarbodiimide (95 mg) and dimethylaminopyridine (1 mg). After 7 days at 20°-25°, aqueous workup (chloroform, magnesium sulfate) and flash chromatography eluting with ethyl acetate/hexane (3/1) provides the title compound.

EXAMPLE 154

2-[[4-(2,6-Bis(1-pyrrolidinyl)-4-pyrimidinyl)-1-piperazinyl]methyl]-3,4-dihydro-2,5,7,8-tetramethyl-2H-1-benzopyran-6-(4-dimethylaminobutoxy) (III-prodrug)

Following the general procedure of EXAMPLE 153 and making non-critical variations but using dimethylamino butyric acid, the title compound is prepared.

EXAMPLE 155

2-[[4-[3-(Ethylamino)-2-pyridinyl]-1-piperazinyl]methyl]-3,4-dihydro-2,5,7,8-tetramethyl-2H-1-benzopyran-6-(dimethylaminoacetoxy) (III-prodrug)

Following the general procedure of EXAMPLE 153 and making non-critical variations but using 2-[[4-[3-(ethylamino)-2-pyridinyl]-1-piperazinyl]methyl]-3,4-dihydro-2,5,7,8-tetramethyl-2H-1-benzopyran-6-(dimethylaminoacetoxy), the title compound is prepared.

EXAMPLE 156

2-[[4-(2,6-Bis(1-pyrrolidinyl)-4-pyrimidinyl)-1-piperazinyl]methyl]-3,4-dihydro-2,5,7,8-tetramethyl-2H-1-benzopyran-6-(5-aminopentanoate) (III-prodrug)

Following the general procedure of EXAMPLE 159 and making non-critical variations but using 5-t-butyloxycarbonylamino pentanoic acid, the protected amino ester is prepared. The t-butyl carbonate is deprotected by treatment with methanolic hydrochloric acid over 18 hr. Concentration and trituration with ether provides the title compound.

EXAMPLE 157

2-[[4-(2,6-Bis(1-pyrrolidinyl)-4-pyrimidinyl)-1-piperazinyl]methyl]-3,4-dihydro-2,5,7,8-tetramethyl-2H-1-benzopyran-6-O-succinate sodium (III-prodrug)

Following the general procedure of EXAMPLE 158 and making non-critical variations but utilizing succinic anhydride the title compound is obtained.

EXAMPLE 158

2-[[4-[3-(Ethylamino)-2-pyridinyl]-1-piperazinyl]methyl]-3,4-dihydro-2,5,7,8-tetramethyl-2H-1-benzopyran-6-O-malate sodium (III-prodrug)

A solution of tetrahydrofuran (2.0 ml), sodium hydride (0.60 mmol), and 2-[[4-[3-(ethylamino)-2-pyridinyl]-1-piperazinyl]methyl]-3,4-dihydro-2,5,7,8-tetramethyl-2H-1-benzopyran-6-ol is stirred for 1 hr at 20°-25°. Maleic anhydride (0.59 mmol) is added. After 2 days, the solution was concentrated and triturated with ether to give the title compound.

EXAMPLE 159

2-[[4-(2,6-Bis(1-pyrrolidinyl)-4-pyrimidinyl)-1-piperazinyl]methyl]-3,4-dihydro-2,5,7,8-tetramethyl-2H-1-benzopyran-6-(6-aminohexanoate) (III-prodrug)

Methylene chloride (3.0 ml) is added to a solid mixture of 2-[[4-(2,6-Bis(1-pyrrolidinyl)-4-pyrimidinyl)-1-piperazinyl]methyl]-3,4-dihydro-2,5,7,8-tetramethyl-2H-1-benzopyran-6-ol (0.30 g), dicyclohexylcarbodiimide (143 mg) and dimethylaminopyridine (1 mg). After 72 hr the reaction is filtered. The filtrate is partitioned between aqueous sodium bicarbonate and methylene chloride. The combined organic layers are dried (magnesium sulfate) and concentrated. Purification by flash chromatography hexane/ethyl acetate (1.5/1) provides the protected amino ester.

A solution of the amino ester (387 mg) methylene chloride (5.0 ml) and trifluoroacetic acid (5.0 ml) are stirred for 30 min at 0° C. After concentration, basic workup (chloroform, postassium carbonate, magnesium sulfate) provides an oil which is immediately taken up into methanol and added to a solution of oxalic acid (2.2 equivalents) in methanol. Concentration and trituration with ether provides the title compound.

EXAMPLE 160

2-[[4-(2,6-Bis(1-pyrrolidinyl)-4-pyrimidinyl)-1-piperazinyl]methyl]-3,4-dihydro-2,5,7,8-tetramethyl-2H-1-benzopyran-6-(4-aminobutyrate) (III-prodrug)

Following the general procedure of EXAMPLE 156 and making non-critical variation but using 4-t-butyloxycarbonylamino butyric acid, the title compound is obtained.

EXAMPLE 161

6-Acetyloxy-3,4-dihydro-2,5,7,8-tetramethyl-2H-1-benzopyran-2-carboxylic acid 2-[(2,6-bis-1-pyrrolidinyl)-4-pyrimidinylmethylamino]ethylester (III)

A solution of oxalyl chloride (0.4 ml) in acetonitrile (0.4 ml) is added dropwise to a solution of 1 ml of DMF and 2.4 ml of acetonitrile. The mixture is stirred (mechanically) for 15 minutes at −20° and a precipitate separates. Powdered 6-acetoxy-2,5,7,8-tetramethyl-chroman-2-carboxylic acid (1.169 g, 4 mmol) is added, the mixture is stirred 20 minutes at −20°, 20 minutes at 0° and then is recooled to −20°. A solution of 1.165 g (4 mmol) of N-(2-hydroxyethyl)-N-methyl-[2,6-bis(1-pyrrolidinyl)]-4-pyrimidinamine in 1 ml of pyridine and a total of 4 ml of acetonitrile is added. The mixture is allowed to warm and stand overnight at 20°-25° and then is diluted with methylene chloride. The solution is washed with water, aqueous potassium bicarbonate and water, then dried and concentrated to give a foam. Chromatography on silica gel and elution with acetone/methylene chloride (10/90) gives the title compound. NMR 4.70, 4.27, 3.9-3.2, 2.85, 2.58, 2.32, 2.17, 2.16, 2.02, 1.9 and 1.58 δ; m.p. 69.5°-76°.

EXAMPLE 162

6-Acetyloxy-3,4-dihydro-2,5,7,8-tetramethyl-2H-1-benzopyran-2-carboxylic acid 2-[(2,6-bis-1-pyrrolidinyl)-4-pyrimidinylmethylamino]propyl ester (III)

Following the general procedure of EXAMPLE 161 and making non-critical variations the title compound is obtained. MS (EI) m/e 634; methanesulfonate salt m.p. 97-104.

EXAMPLE 163

Sodium Suleptanate Ester of 2-[[4-(2,6-bis(1-pyrrolidinyl)-4-pyrimidinyl)-1-piperazinyl]methyl]-3,4-dihydro-2,5,7,8-tetramethyl-2H-1-benzopyran-6-ol (III-prodrug)

Triethylamine (0.022 ml) and diethylcyanophosphonate (0.0255 ml) are added to a mixture of 2-[[4-(2,6-bis(1-pyrrolidinyl)-4-pyrimidinyl)-1-piperazinyl]methyl]-3,4-dihydro-2,5,7,8-tetramethyl-2H-1-benzopyran-6-ol (EXAMPLE 21, 0.064 g) and suleptanic acid monotriethylamine salt, $HO-CO-(CH_2)_6-CO-N(CH_3)-CH_2CH_2-SO_2-O^--(ethyl)_3-N^+-H$ (0.23 ml) as a 0.65M solution in acetonitrile. The mixture is stirred for 7 days after which the solvents are removed under reduced pressure. Methylene chloride and several drops of aqueous sodium bicarbonate are added. The material is concentrated and chromatographed on silica gel using methanol/methylene chloride (15/85). The appropriate fractions are pooled and concentrated to give the triethylamine salt of the suleptanate ester. The triethylamine salt is taken up in n-butanol and partitioned with aqueous sodium sulfate (1 g/10 ml of water). The n-butanol layer is separated and the n-butanol is removed under reduced pressure. Water is added to the residue and the material is lyophilized to give the title compound, mp = 160°-180° (phase change); MS (FAB) [M+H]+ at m/e=798 (for free sulfonic acid), at m/e=820.

EXAMPLE 164

Sodium Suleptanate Ester of 2-[[4-[3-(ethylamino)-2-pyridinyl]-1-piperazinyl]methyl]-3,4-dihydro-2,5,7,8-tetramethylbenzopyran-6-ol (III-prodrug)

Following the general procedure of EXAMPLE 163 and making non-critical variations but using 2-[[4-[3-(ethylamino)-2-pyridinyl]-1-piperazinyl]methyl]-3,4-dihydro-2,5,7,8-tetramethylbenzopyran-6-ol (EXAMPLE 22) the title compound is obtained.

EXAMPLE 165

1-[(2-Hydroxy-5-methoxy-1-phenyl)methyl]-4-[3-ethylamino-2-pyridinyl]piperazine (VI-47)

Sodium cyanoborohydride (290 mg) is added to a solution of 2-hydroxy-5-methoxybenzaldehyde (0.452 ml), 1-[(3-(ethylamino)-2-pyridinyl]piperazine (1.12 grams), methanol (14 ml), and hydrochloric acid (10%, 0.10 ml). The mixture is stirred for 16 hours at 20°-25°. The mixture is then concentrated, worked up by aqueous extraction with chloroform. The organic phase is separated, dried over magnesium sulfate and purified by flash chromatography eluting with hexane/ethyl acetate (1/1). The appropriate fractions are pooled and concentrated to give the title compound, MS (EI) m/e 342 (M−).

EXAMPLES 166-172

Following the general procedure of EXAMPLE 165 and making non-critical variations but starting with the appropriate known phenols and amines the following compounds are obtained:

| EXAMPLE | Hydroquinone (VI) |
|---|---|
| 166 | 1-[(2,5-Dihydroxy-1-phenyl)methyl]-4-[2,6-bis(1-pyrrolidinyl)-4-pyrimidinyl]piperazine (VI-22), MS (EI) m/e 424 (M+) |
| 167 | 1-[(2-Hydroxy-5-methoxy-1-phenyl)methyl]-4-[2,6-bis(1-pyrrolidinyl)-4-pyrimidinyl]piperazine (VI-22), MS (EI) m/e 438 (M+) |
| 168 | 1-[(2,5-Dihydroxy-1-phenyl)methyl]-4-[3-ethyl-amino-2-pyridinyl]piperazine (VI-47), MS (EI) m/e 328 (M+) |
| 169 | 1-[(2,5-Dihydroxy-1-phenyl)methyl]-4-[5,6-bis(diethyl-amino)-2-pyridinyl]piperazine (VI-46), MS (EI) m/e 427 (M+) |
| 170 | 1-[(2-Hydroxy-5-methoxy-1-phenyl)methyl]-4-[5,6-bis(diethylamino)-2-pyridinyl]piperazine (VI-46), MS (EI) m/e 441 (M+) |
| 171 | 1-[(2-Hydroxy-5-methoxy-1-phenyl)methyl]-4-[5-diethylamino-2-pyridinyl]piperazine (VI-59), MS (EI) m/e 370 (M+) |
| 172 | 1-[(2,5-Dihydroxy-1-phenyl)methyl]-4-[5-diethyl-amino-2-pyridinyl]piperazine |

EXAMPLE 173

2,5-Dihydroxyphenylmethyl-3,4-dimethoxyphenylethylamine (VI-38)

Imidazole (3.08 grams) is added to a mixture of 2,4-dihydroxybenzaldehyde (2.50 grams), t-butyldimethysilylchloride (6.46 grams) and DMF (20 ml). After stirring overnight at 20°-25° the crude reaction mixture is partitioned between ether and hydrochloric acid (0.5N). The layers are separated and the organic phase is washed with aqueous sodium bicarbonate, dried over magnesium sulfate, filtered and concentrated to provide the disilylated aldehyde intermediate.

A solution of the disilylated aldehyde intermediate (8.26 grams), 3,4-dimethoxyphenylethylamine (3.54 grams), toluene (30 ml) and toluene sulfonic acid (150 milligrams) is heated at reflux for 24 hours removing 10 ml of the solvent in a Dean-Starke trap. After cooling to 20°-25° sodium borohydride (1.2 grams), and ethanol (40 ml) are added. After stirring for an additional 2 hours additional sodium borohydride (0.60 grams) and hydrochloric acid (10%, 4.0 ml) are added. The resulting mixture is stirred for 20 hours. After a concentration the mixture is worked up under basic conditions using chloroform, sodium bicarbonate and drying the resultant extract over magnesium sulfate. The mixture is then concentrated, the concentrate is flash chromatographed eluting with hexane/ethyl acetate (1.5/1) to provide a 3,4-dimethoxyphenylethylamine disilylated intermediate.

Tetrabutylammoniumfluoride (5.8 ml) is added to the silylated intermediate (2.1 grams) in THF (25 ml). The mixture is stirred for 1 hour at 20°-25°. The mixture is worked up under acidic conditions using ether and chloroform and drying over magnesium sulfate. Upon concentration the title compound is obtained as an oil.

EXAMPLE 174

2-Hydroxy-5-methoxyphenylmethyl-3-4-dimethoxyphenylethylamine (VI-38)

Following the general procedure of EXAMPLE 173 and making non-critical variations but starting with 2-hydroxy-5-methoxybenzaldehyde, the title compound is obtained, m.p. 66-67.

EXAMPLE 175

3,4-Dihydro-3-[2-(3,4-dimethoxyphenyl)ethyl]-1,3,2-benzoxazin-6-ol (VIII-66)

A mixture of 2,5-dihydroxyphenylmethyl-3,4-dimethoxyphenylethylamine (EXAMPLE 175, 0.476 gm), paraformaldehyde (56 mg), THF (10 ml) and magnesium sulfate (0.240 gm) are stirred at 20°-25° for 5 days. The mixture is worked up under aqueous conditions using chloroform and drying over magnesium sulfate to provide the title compound, MS (EI) m/e 315 (M−)

EXAMPLE 176

2,3,4,5-Tetrahydro-7-methoxy-4-[2-(3,4-dimethoxy)-phenylethyl]-1,4-benzoxazepin-3-one (VIII-38)

Chloroacetylchloride (0.26 ml) is added dropwise over 10 minutes to a mixture of 2-hydroxy-5-methoxyphenylmethyl-3-4-dihydroxyphenylamine (EXAMPLE 174, 1.0 grams), THF (5 ml), ether (15 ml) and triethylamine (0.49 ml) at 20°-25°. After 20 hours, the residue is partitioned between hydrochloric acid (0.05N) and ethyl acetate. The organic layers are combined, dried over magnesium sulfate, filtered and concentrated under reduced pressure to give the crude amide.

A mixture of the crude amide (1.18 grams), acetone (50 ml), and potassium carbonate (0.69 grams) are stirred at 20°-25° for 60 hours. The mixture is filtered, concentrated and worked up under aqueous conditions using methylene chloride and magnesium sulfate. The concentrate is purified by flash chromatography eluting with ethyl acetate/hexane (3/1). The appropriate fractions are pooled and concentrated to give the title compound, m.p. 102°-103°

EXAMPLE 177

2,3,4,5-Tetrahydro-4-(2-(3,4-dimethoxyphenyl)ethyl)-7-methoxy-1,4-benzoxazepine (VIII-38)

A solution of 2,3,4,5-tetrahydro-7-methoxy-4-[2-(3,4-dimethoxy)phenylethyl-1,4-benzoxazepin-3-one (EXAMPLE 176, 0.382 gm) and THF (3 ml) are added dropwise over 15 minutes to a mixture of lithium aluminum hydride (101 mg) and ether (3 ml). The resulting mixture is stirred for 20 hours at 20°-25°. Water (0.12 ml), sodium hydroxide (15%, 0.12 ml) and water (0.36 ml) are added successively. The mixture is then diluted with ether and stirred for 30 minutes. The mixture is filtered, the residual salts are washed with ethyl acetate chloroform and ethyl acetate again. The organic mixtures are combined, dried over magnesium sulfate and concentrated to give the title compound.

EXAMPLE 178

1-[[6-(Acetyloxy)-3,4-dihydro-2,5,7,8-tetramethyl-2H-1-benzopyran-2-yl]acetyl]-4-(4,6-bis(1-pyrrolidinyl)-1,3,5-triazin-2-yl)piperazine (III-45)

Following the general procedure of EXAMPLE 68 and making non-critical variation but starting with 4,6- bis(1-pyrrolidinyl)-1,3,5-triazin-2-yl)piperazine (PREPARATION A-45), the title compound is obtained.

EXAMPLE 179

1-[(3,4-Dihydro-6-hydroxy-2,5,7,8-tetramethyl-2H-1-benzopyran-2-yl)acetyl]-4-[4,6-bis(1-pyrrolidinyl)-1,3,5-triazin-2-yl]piperazine (III-45)

Following the general procedure of EXAMPLE 75 and making non-critcial variation but starting with 1-[[6-(acetyloxy)-3,4-dihydro-2,5,7,8-tetramethyl-2H-1-benzopyran-2-yl]acetyl]-4-(4,6-bis(1-pyrrolidinyl)-1,3,5-triazin-2-yl)piperazine (EXAMPLE 178), the title compound is obtained.

EXAMPLE 180

1-[2,6-Bis(1-pyrrolidinyl)-4-pyrimidinyl]-4-[(3,4-dihydro-6-acetyloxy-2,5,7,8-tetramethyl-2H-1-benzopyran-2-yl)carbonyl]piperazine (III-22)

Acetic anhydride (0.056 g), [4-(2,6-bis(1-pyrrolidinyl)-4-pyrimidinyl)-1-piperazine]-6-hydroxy-2,5,7,8-tetramethylchroman-2-carboxamide (EXAMPLE 18, 0.26 g) and pyridine (1 ml) are stirred for 2 hr at 20°–25°. Hydrochloric acid (0.01N, 5 ml) and ethyl acetate (5 ml) are added, the layers separated, the organic phase washed with saline and dried over magnesium sulfate. The solvent is removed under reduced pressure to give a residue which is crystallized to give the title compound, m.p. 191°–192°; MS (EI) m/e 576 (M+).

EXAMPLE 181

N-[2-[1-(2-Pyridinyl)ethyl]]-N-[2-(1-phenyl)ethyl]-3,4-dihydro-6-hydroxy-2,5,7,8-tetramethyl-2H-1-benzopyran-2-carboxamide (III-82)

Following the general procedure of EXAMPLE 18 and the description of the general procedure in the specification to prepare the amide type bicyclic amines (III) where $X_3$ is —CO—, the title compound is obtained.

EXAMPLE 182

4-[4-[2-(Ethylamino)-4-(2-pyridinyl)-1-piperazinyl]-butyl]-2,6-dimethylphenol methanesulfonate (I-63)

Following the general procedure of EXAMPLE 44 and making non critical variations 4-[2,6-dimethyl-1-hydroxy-4-phenyl]butanol (PREPARATION NA-15) is reacted with 2-(ethylamino)-4-(2-pyridinyl)piperazine (Amine-63) to provide the hydroxy intermediate of the title compound. This hydroxy intermediate is esterified with methanesulfonic acid to give the title compound.

EXAMPLE 183

1-[[6-(Acetyloxy)3,4-dihydro-2,5,7,8-tetramethyl-2H-1-benzopyran-2-yl]acetyl]-4-(phenylmethyl)piperazine (III)

Following the general procedure of EXAMPLE 68 and making non-critical variations and starting with benzylpiperazine, the title compound is obtained.

EXAMPLE 184

3,4-Dihydro-2,5,7,8-tetramethyl-2-[2-[4-(phenylmethyl)-1-piperazinyl]ethyl]-2H-1-benzopyran-6-ol (III)

Following the general procedure of EXAMPLE 21 and making non-critical variations but starting with 1-[[6-(acetyloxy)3,4-dihydro-2,5,7,8-tetramethyl-2H-1-benzopyran-2-yl]acetyl]-4-(phenylmethyl)piperazine (EXAMPLE 183), the title compound is obtained.

EXAMPLE 185

3,4-Dihydro-7-hydroxy-4-[2-(3,4-dimethoxyphenyl)ethyl]-1,4-benzoxazine-3-one (IX).

To a solution of 4-aminoresorsinal hydrochloride (1.00 mmol) in dichloromethane (2.0 ml) at 0° is added successively a solution of chloroacetylchloride (1.1 eq) and triethylamine (2.5 eq). Stirred at 0° for 2 hr and at 20°–25° 4 h. Concentrated, the residue is taken up into acetone (10.0 ml) and potassium carbonate (1.2 eq) is added. Stirred for 24 h at 20°–25°. After concentration the residue was partitioned between water and chloroform. The chloroform layers were dried over magnesium sulfate and concentrated. Purification by flash chromatography eluting with ethyl acetate provided the unsubstituted amide.

A solution of the amide (0.50 mmol) was added to a mixture of sodium hydride (2.3 mmol) and dimethyl formamide (2.0 ml). After stirring for 30 min a solution of 1-bromo-2-(3,4-dimethoxyphenyl)ethane (0.50 mmol) in dimethyl formamide (1.0 ml) was added at 0° C. After 2 h an aqueous workup with ethyl acetate was performed. The organic layers were dried with magnesium sulfate and concentrated. Purification by flash chromatography provided the title compound.

EXAMPLE 186

3,4-dihydro-7-hydroxy-4-[2-(phenylethyl)]-1,4-benzoxazine-3-one (IX)

Following the general procedure of EXAMPLE 185 and making non-critical variations but using 2-phenethyl-1-bromide, the title compound is obtained.

EXAMPLE 187

3,4-Dihydro-7-hydroxy-4-[1-phenylmethyl]-1,4-benzoxazine-3-one (IX)

Following the general procedure of EXAMPLE 185 and making non-critical variations but using benzyl bromide, the title compound is obtained.

EXAMPLE 188

3,4-dihydro-7-hydroxy-4-[1-[4-(dimethylamino)phenyl]ethyl]-1,4-benzoxazine-3-one (IX)

Following the general procedure of EXAMPLE 185 and making non-critical variations but using 4-dimethylaminobenzylbromide, the title compound is obtained.

EXAMPLE SALTS

Following the general procedure of EXAMPLES 1A, 17A, 22A, 24A, 26A, 42A, 42B, 43A, 44A and 45A and making non-critical variations and starting with the free amine bases of EXAMPLES 29-32, 35-39, 48-57, 60-67, 71 and 72 the corresponding salts are formed

| EXAMPLE | Salt |
|---|---|
| 29A | 4-[4-[4-(2,6-bis(2-pyridinyl)-4-pyrimidinyl)-1-piperazinyl]butoxy]phenol 3.4 hydrochloride |
| 30A | 4-[6-[4-(2,6-bis(1-pyrrolidinyl)-4-pyrimidinyl)-1-piperazinyl]hexyloxy]phenol fumerate |
| 31A | 4-[6-[4-[3-(ethylamino)-2-pyridinyl]-1-piperazinyl]hexyloxy]phenol monomethane sulfonate |
| 32A | 4-[6-[4-(3,6-bis(2-pyridinyl)-4-pyridazinyl)methyl-1-piperazinyl]hexyloxy]phenol trihydrochloride |
| 35A | 5-[3-(4-(2,6-bis(1-pyrrolidinyl)pyrimidin-4-yl)piper- |

-continued

| EXAMPLE | Salt |
|---|---|
| | azin-1-yl)propylbenzodioxole dihydrochloride |
| 36A | 5-[3-N-ethylaminopyridin-2-yl)piperazin-1-yl) propylbenzodioxole dihydrochloride |
| 38A | 1-[[(4-methoxyphenyl)-2-ketoeth-1-yl]butyl]-4-(bis(1-pyrrolidinyl))pyrimidin-4-yl)piperazine monomethane sulfonate |
| 39A | 1-phenyl-3-[4-(2,6-bis(1-pyrrolidinyl)-4-pyrimidinyl)-1-piperazinyl]-propane monomethane sulfonate |
| 48A | 4-[3-(4-(3-(N-ethylamino)pyridin-2-yl)piperazin-1-yl)-propyl]-2,6-dimethylphenol hydrochloride |
| 49A | 2,6-bis(1-pyrrolidinyl)-4-[4-(3-(3,5-dimethyl-4-methoxy-phenyl)propyl)piperazinyl]pyrimidine dihydrochloride 0.66 H₂O |
| 50A | N-ethyl-2-[4-[3-(4-methoxy-3,5-dimethylphenyl)propyl]-1-piperazinyl]-3-pyridinamine hydrochoride |
| 51A | 4-[2-[4-(2,6-bis(1-pyrrolidinyl)-4-pyrimidinyl-1-piperazinyl]ethyl]-2,6-dimethylphenol dihydrochloride hydrate |
| 52A | 4-[2-[4-[3-(ethylamino)-2-pyridinyl]-1-piperazinyl]-ethyl]2,6-dimethylphenol dihydrochloride |
| 53A | 4-[bis-(1-pyrrolidinyl)-4-pyrimidinyl]-1-[2-(6,7-dimethoxy-isochromyl)eth-1-yl]piperazine hydrochloride |
| 54A | 2,4-bis-(1-pyrrolidinyl)-6-[4-[2-[2-[(1,3,4,5-tetrahydro-7,8-dimethoxy-2-benzoxepin-1-yl)methoxy]ethoxy]ethyl]-1-piperazinyl]pyrimidine monomethane sulfonate |
| 55A | 4-[3-ethylamino-2-pyridinyl]-1-[2-[6,7-dimethoxy-isochromyl]9 eth-1-yl]piperazine dihydrochloride |
| 56A | 4-[4-[2-(4-methoxy-3,5-dimethylphenyl)ethyl]-1-piperazinyl]-2,6-bis(1-pyrrolidinyl)pyrimidine dihydrochloride 1.33 hydrate |
| 57A | N-ethyl-2-[4-[2-(4-methoxy-3,5-dimethylphenyl)ethyl]-1-piperazinyl]-3-pyridinamine dihydrochloride hydrate |
| 59A | 2-[4-(6-(3,5-dimethyl-4-methoxyphenyl)hexyl)piperazinyl-N-ethyl-3-pyridinamine hydrochloride |
| 60A | 3-[6-(4-(3-(ethylamino)pyridin-2-yl)piperazin-1-yl)-hexyl]cyclohex-2-en-1-one hydrochloride |
| 61A | 3-[6-((2,6-bispyrrolidin-1-yl)pyrimidin-4-yl)piperazin-1-yl)hexyl]cyclohex-2-en-1-one hydrochloride |
| 62A | 3-[4-(4-(3-(ethylamino)pyrid-2-yl)piperazin-1-yl)butyl]-cyclohex-2-en-1-one hydrochloride |
| 63A | 3-[3-(4-(3-(ethylamino)pyrid-2-yl)piperazin-1-yl)propyl]-cyclohex-2-en-1-one hydrochloride |
| 64A | 3-[3-(4-(2,6-bis(1-pyrrolidinyl)pyrimidin-4-yl)piperazin-1-yl)propyl]-cyclohex-2-en-1-one hydrochloride |
| 65A | 1-phenoxy-4-[4-(2,6-bis(1-pyrrolidinyl)-4-pyrimidinyl-piperazinyl]-butane monomethane sulfonate |
| 66A | 1-[3,4-dihydro-6-hydroxy-2,5,7,8-tetramethyl-2H-1-benzo-pyran-2-yl)acetyl]-4-(2,6-bis(1-pyrrolidinyl)-4-pyrimidinyl)-piperazine methane sulfonate |
| 67A | 1-[3,4-dihydro-6-hydroxy-2,5,7,8-tetramethyl-2H-1-benzopyran-2-yl)ethyl]-4-(2,6-bis(1-pyrrolidinyl)-4-pyrimidinyl)-piperazine methane sulfonate |
| 71A | 4-[[3,5-Bis(1,1-dimethylethyl)-4-hydroxyphenyl]methyl]-1-piperazineethanol fumerate |
| 72A | 2,6-bis(1,1-dimethylethyl)-4-[[4-(3-ethylamino)-2-pyridinyl]-1-piperazinyl]methyl]phenol fumerate |
| 73A | 4-(2,6-bis(1-pyrrolidinyl)-4-pyrimidinyl)-N-(4-hydroxy-3,5-dimethylphenyl)-1-piperazineacetamide monomethane sulfonate |

Following the general procedure of EXAMPLES 1A, 17A, 22A, 24A, 26A, 42A, 42B, 43A, 44A and 45A and making non-critical variations and starting with the free amine bases of the corresponding EXAMPLES (No) the following salts (NoA) are formed by use of the appropriate acid

| EXAMPLE | Salt |
|---|---|
| 113A | poly-hydrochloride hydrate crystallized from methanol-ether |
| 114A | hydrochloride |
| 115A | dihydrochloride hydrate |
| 116A | poly-phdrochloride hydrate |
| 117A | hydrochloride |
| 119A | dihydrochloride hydrate |
| 120A | dihydrochloride hydrate |
| 121A | dihydrochloride hydrate |
| 125A | dihydrochloride hydrate |
| 126A | dihydrochloride |
| 135A | oxalate |
| 136A | oxalate |
| 137A | hydrochloride |
| 138A | oxalate |
| 141A | oxalate |
| 142A | oxalate |
| 143A | oxalate |
| 145A | dihydrochloride hydrate |
| 147A | oxalate |
| 151A | oxalate |
| 152A | oxalate |
| 153A | dioxalate |
| 154A | dioxalate |
| 155A | dioxalate |
| 160A | ethanedioate m.p. 162–164° |
| 166A | hydrochloride |
| 167A | oxalate |
| 168A | oxalate |
| 169A | oxalate |
| 170A | oxalate |
| 171A | oxalate |
| 172A | oxalate |
| 173A | oxalate. m.p. 167–169°. |
| 175A | oxalate. m.p. 49°. |

CHART A

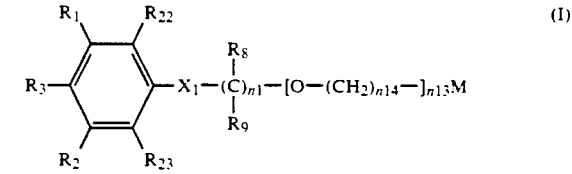

(I)

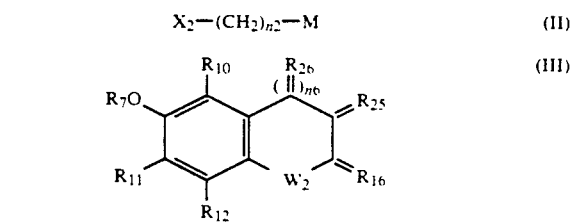

(II)

(III)

(IV)

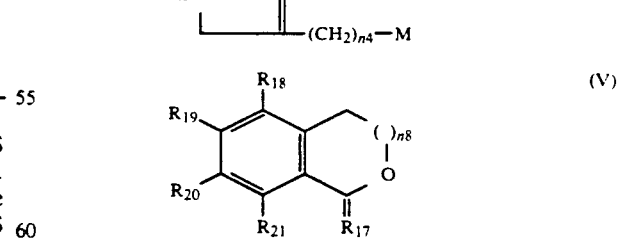

(V)

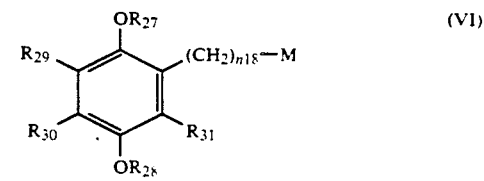

(VI)

-continued
CHART A
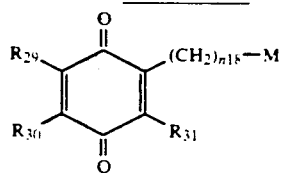 (VII)
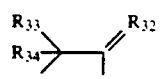 (VIII)
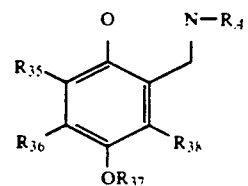
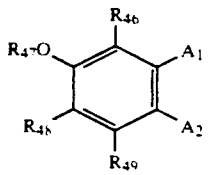 (IX)
-continued
CHART A
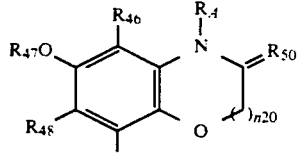 (IXA)
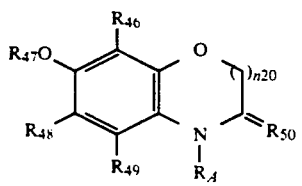 (IXB)
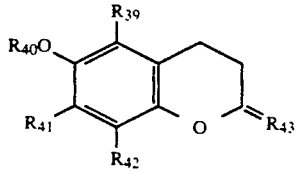 (XI)
CHART B
| Name | Chemical Structure | Formula No. |
|---|---|---|
| pyridin-2-, | 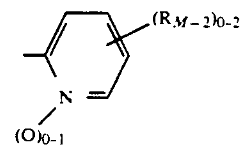 | (F-1) |
| 3-, | 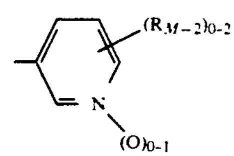 | (F-2) |
| or 4-yl optionally substituted optionally as the N-oxide | 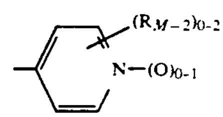 | (F-3) |
| $-*CH_2-(CH_2)_c-G-(CH_2)_d-CH_2-N^*-$ | | (F-4) |
| 3-pyrrolin-1-yl | 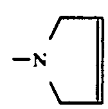 | (F-5) |
| pyrrol-1-yl optionally substituted | 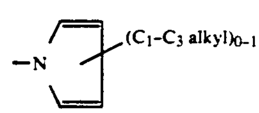 | (F-6) |
| piperidin-1-yl optionally substituted | 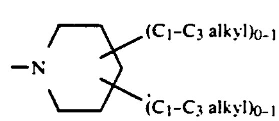 | (F-7) |

CHART B-continued

| Name | Chemical Structure | Formula No. |
|---|---|---|
| 1,2,3,6-tetrahydropyridin-1-yl | 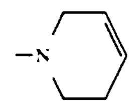 | (F-8) |
| 1-hexamethyleneimino containing a 3- or 4- double bond or 3- and 5- double bonds | 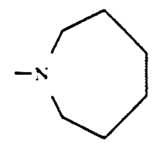 | (F-9) |
| 1,4-dihydro-1-pyridinyl substituted in the 4-position | a number of different groups / a number of different groups | (F-10) |
| 1,3,5-triazin-2-yl or the $N_1$-oxide thereof optionally substituted at the 4- and/or 6- position | $(R_{M-2})_{0-1}$ / $N-(O)_{0-1}$ / $(R_{M-2})_{0-1}$ | (F-11) |
| pyrimidin-4-yl or the $N_1$-oxide thereof optionally substituted at the 2- and/or 6- and 5- and/or 6- position | $(R_{M-2})_{0-1}$ / $N-(O)_{0-1}$ / $(R_{M-2})_{0-1}$ | (F-12) |
| pyrimidin-2-yl optionally substituted | $(R_{M-2})_{0-2}$ | (F-13) |
| pyrazin-2-yl optionally substituted | $(R_{M-2})_{0-2}$ | (F-14) |
| imidazol-2-yl optionally substituted in | $(R_{M-2})_{0-2}$ / $(C_1-C_3 \text{ alkyl or aryl})_{0-1}$ | (F-15) |
| 1,3,4-triazol-2-yl optionally substituted | $(R_{M-2})_{0-1}$ / $(C_1-C_3 \text{ alkyl or aryl})_{0-1}$ | (F-16) |
| imidazol-4- or 5-yl optionally substituted | $(R_{M-2})_{0-2}$ / $(C_1-C_3 \text{ alkyl or aryl})_{0-1}$ | (F-17) |

CHART B-continued

| Name | Chemical Structure | Formula No. |
|---|---|---|
| benzo[b]thien-2-yl | 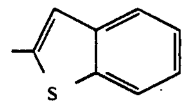 | (F-18) |
| indol-2-yl | 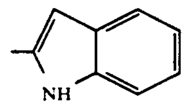 | (F-19) |
| benzo[b]thiazol-2-yl | 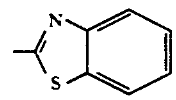 | (F-20) |
| benzimidazol-2-yl | 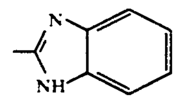 | (F-21) |
| 4-[2-[4-[2,6-di-(1-pyrrolidinyl)-4-pyrimidinyl]-1-piperazinyl]ethyl] | 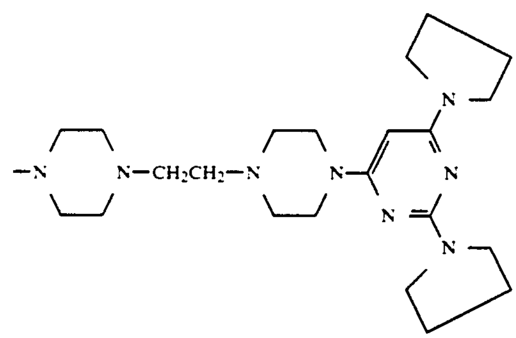 | (F-22) |
| 1,2,4-triazin-3-yl optionally substituted at the 5- and/or 6-position | $(R_M-2)_{0-1}$ | (F-23) |
| (1-piperazinyl)-(C$_2$-C$_4$) optionally substituted in the 4-position | —(C$_2$-C$_4$ alkyl)-N⟩⟨N-(aryl or heteroaryl) | (F-24) |
| (1-piperazinyl)acetyl substituted in the 4-position | —CO—CH$_2$—N⟩⟨N-heteroaryl | (F-25) |
| (1-piperazinyl)carbonyl-methyl substituted in the 4-position | —CH$_2$—CO—N⟩⟨N-heteroaryl | (F-26) |
| 2-(carboxy)-1-pyrrolidinyl | —N⟩(COOH) | (F-27) |

CHART B-continued

| Name | Chemical Structure | Formula No. |
|---|---|---|
| 2-(carboxy)-1-piperidinyl | [piperidine ring with N attached to main structure and COOH at 2-position] | (F-28) |
| 2-(carboxy)-1-hexamethyleneimino | [7-membered ring with N and COOH at 2-position] | (F-29) |
| 2-(carboxy)-1-heptamethyleneimino | [8-membered ring with N and COOH at 2-position] | (F-30) |
| 1-piperazinyl substituted in the 4-position | $-N\underset{\phantom{x}}{\diagdown}N-(CH_2)_j-CO-R_{M-12}$ | (F-31) |
| 1-piperazinyl substituted in the 4-position | $-N\underset{\phantom{x}}{\diagdown}N-(CH_2)_j$-heteroaryl | (F-32) |
| 1-piperazinyl substituted in the 4-position | $-N\underset{\phantom{x}}{\diagdown}N-(CH_2)_j$-aryl | (F-33) |
| 4-hydroxy-1-piperidinyl substituted in the 4-position | [piperidine with OH and aryl at 4-position] | (F-34) |
| 1-piperazinyl substituted in the 4-position | $-N\underset{\phantom{x}}{\diagdown}N-(CH_2)_j-CO-NR_{21-13}$-heteroaryl | (F-35) |
| 1-piperazinyl substituted in the 4-position | [piperazine linked via $-(CH_2)_j-$ to a pyridazine ring bearing two 2-pyridyl substituents] | (F-36) |

CHART B-continued

| Name | Chemical Structure | Formula No. |
|---|---|---|
| 1-piperazinyl substituted in the 4-position | 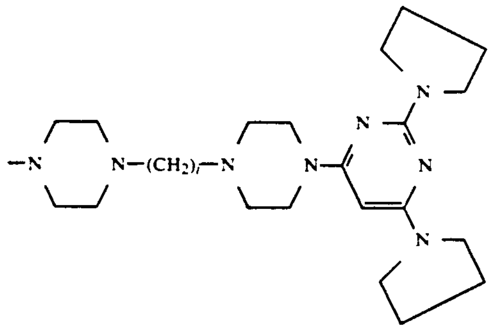 | (F-37) |

CHART C Physical Data

| Example | Physical Data |
|---|---|
| 1 | NMR (CDCl₃) 1.40, 1.88, 2.46, 3.52, and 3.82 δ. |
| 1A | m.p. 164-164.5° |
| 2 | NMR (CDCl₃) 1.4, 2.3-2.7, 3.4-3.8, 6.55-6.8, 7.3-7.7 and 8.25 δ. |
| 2A | m.p. 106-108° |
| 3 | NMR (CDCl₃) 1.2-1.8, 2.4-2.9, 3.25, 3.7, 4.2, 6.95 and 7.8 δ. |
| 3A | m.p. 128-129° |
| 4 | NMR (CDCl₃) 1.36, 2.45, 3.62, 4.02, 7.37-7.6, 7.85-8.35 and 8.7-9.0 δ |
| 4A | m.p. 121-135 dec |
| 5 | NMR (CDCl₃) 1.1-1.8, 2.56, 3.62, 3.87, 7.1-7.4, 7.5-7.9 and 8.45-8.6 δ |
| 5A | m.p. 62-71° |
| 6 | NMR (CDCl₃) 0.88, 1.30, 1.8-2.1, 2.25-2.65, 3.35-3.7 and 4.88 δ |
| 6A | m.p. 132-133° |
| 7 | NMR (CDCl₃) 1.4-2.1, 2.2-2.7, 3.3-3.8, 3.68 and 4.88 δ |
| 7A | mp 178° dec |
| 8 | NMR (CDCl₃) 0.88, 1.30, 1.92, 2.2-2.65, 3.3-3.8 and 4.88 δ. |
| 8A | mp 216-217° |
| 9 | NMR (CDCl₃) 1.42, 1.8-2.1, 2.3-2.7, 3.3-3.8 and 4.88 δ |
| 9A | m.p. 174-175° |
| 9B | m.p. 74-100° |
| 10 | NMR (CDCl₃) 1.3, 1.8-2.0, 2.25-2.65, 3.35-3.8 and 4.9 δ |
| 10A | m.p. 152.5-158° |
| 11 | NMR (CDCl₃) 1.35, 1.75-2.1, 2.25-2.75, 3.3-3.8 and 4.88 δ |
| 11A | m.p. 110-118° |
| 12 | NMR (CDCl₃) 1.35-1.65, 1.65-1.95, 2.2-2.65, 3.25-3.75 and 4.8 δ |
| 12A | m.p. 63-80° |
| 13 | NMR (CDCl₃) 1.3, 1.8-2.1, 2.25-2.7, 3.0-3.8 and 4.9 δ |
| 13A | m.p. 109-112° |
| 14 | NMR CDCl₃) 1.25, 2.3-2.8, 3.0-3.3, 3.6, 4.1, 6.7-7.1 and 7.8 δ |
| 14A | m.p. 153.5-156° |
| 15 | NMR (CDCl₃) 1.1-1.85, 2.3-2.75, 2.9-3.3, 3.62, 4.1, 6.7-7.7 and 7.8 δ |
| 15A | m.p. 151.5-153.5° |
| 16 | NMR (CDCl₃) 1.42, 2.55, 3.62, 4.15, 7.48, 7.9, 8.65 and 8.9 δ |
| 17 | NMR (CDCl₃) 1.0-1.8, 2.35, 3.05, 3.55, 7.25-7.5, 7.7-8.2, 8.55 and 8.65-8.9 δ. |
| 18 | m.p. 123-127°; MS = 534 (M⁺) |
| 19 | m.p. 200-201°; MS = 438 (M⁺) |
| 20 | m.p. 178-181°; MS = 550 (M⁺) |
| 21 | m.p. 153-155°; MS = 520 (M⁺) |
| 22 | NMR (CDCl₃) 1.28, 1.29, 1.75, 1.96, 2.09, 2.12, 2.16, 2.55, 2.62, 2.71, 2.81, 3.07, 4.20, 4.31, 6.79, 6.88 and 7.70 δ |
| 22A | m.p. 208-211° dec; MS = 424 (M⁻) |
| 23 | m.p. 132-136°; MS (FAB) = 537 (M + H)⁺ |
| 24 | NMR (CDCL₃) 7.1, 5.1, 4.85, 3.6-3.3, 2.5-1.3, 1.43 δ |
| 24A | m.p. 223° |
| 25 | m.p. 92-93°; MS (m/e) = 508 (M⁺) |
| 26 | NMR (90 MHz, CDCl₃) 1.3, 1.3-1.8, 2.45, 2.5-2.65, 3.25-3.95, 3.72, 3.9, 4.2, 6.9, 6.7-6.95 and 7.7-7.8 δ |
| 26A | m.p. 127-128°; MS (m/e) = 412 (M⁻) |
| 27 | m.p. 130-133° |
| 28 | m.p. 146-148° |
| 29 | NMR (300 MHz, CDCl₃) 1.66-1.79, 2.42, 2.44-2.5, 3.85-3.94, 6.71-6.79, 7.35-7.41, 7.65, 7.87-7.81, 8.57, 8.60, 8.66- 8.67 and 8.80 δ |
| 29A | m.p. 255-260° dec; MS (m/e) = 482 (M⁻) |
| 30 | NMR (90 MHz, CDCl₃) 1.3-1.5, 1.6-2.0, 2.2-2.62, 3.3-3.65, 3.83, 4.88 and 6.70 δ. |
| 30A | m.p. 210-212° dec; MS (m/e) 494 (M⁻) |
| 31 | NMR (90 MHz, CDCl₃) 1.22, 1.3-1.55, 1.55-1.9, 2.9-3.2, 3.25-3.67, 3.85, 6.8, 6.8-7.05 and 7.6-7.7 δ |
| 31A | m.p. 98-102°; MS (m/e) = 388 (M⁻) |
| 32 | NMR (300 MHz, CDCl₃) 1.25-1.40, 1.40-1.51, 1.63-1.73, 2.28, 2.45, 3.84, 3.97, 6.75, 7.37 7.45, 7.88-7.95, 8.11, 8.14 and 8.69-8.81 δ |
| 32A | m.p. 145° dec; MS (m/e) = 524 (M⁻) |
| 33 | m.p. 171-172°; MS (m/e) = 510 (M⁻) |
| 34 | m.p. 160-166°; MS (m/e) = 525 (M⁻) |
| 35 | m.p. 148° softens, 155-160° melts with dec |
| 36A | m.p. 95° softens, 115° dec |
| 38A | m.p. 146-155° dec; MS (m/e) = 450 M⁻ |
| 39 | NMR (CDCl₃) 1.7-2.2, 2.3-2.8, 3.3-3.8, 4.88, 5.32 and 7.3 δ |
| 39A | m.p. 187-190° |
| 40 | m.p. 166-168°; MS (m/e) = 438 (M⁻) |
| 41 | MS m/e 494 |
| 42A | m.p. 115-120° dec |
| 42B | MS (m/e) = 493 (M⁻) |
| 43A | m.p. 180-188° |
| 44A | m.p. 160° |
| 45 | m.p. 138° softens, 160° dec; MS (m/e) = 478 (M⁻) |
| 46 | NMR (CDCl₃) 1.2-1.9, 3.12, 3.77, 3.87, 6.88, 7.3-7.6, 7.8-8.3, 8.57 and 8.7-9.0 δ; m.p. 76-76.5° |
| 47A | m.p. 170-171° |
| 48A | mp.p 224-226° dec |
| 49 | TLC (10% methanol/chloroform) R_f = 0.6 |
| 49A | C₂₈H₄₂N₄6O; MW 563.68 Calc C - 59.66, H - 8.11, N - 14.91, Cl - 12.58 Found C - 59.68, H - 7.73, N - 14.59, Cl - 12.94 |
| 50 | MS (m/e) = 382 (M⁺) |
| 51A | m.p. 205-210° |
| 52A | C₂₁H₃₀N₄O; Calc C - 59.01, H - 7.55, N - 3.11, Cl - 13.59 Found C - 59.39, H - 7.68, N - 13.28, Cl - 11.92 |
| 53A | m.p. 177° softens, 195-200° dec |
| 54A | m.p. 85-90° dec |
| 55 | m.p. 135° softens, 137-141° dec; MS (m/e) = 426 (M⁻) |
| 56A | m.p. 60° shrinks, 150° liquid, 222° dec; MS m/e 464 |
| 57A | m.p. 130° shrinks, 210 dec |
| 58 | m.p. 98°, MS (m/e) = 520 (M⁻) |
| 59 | MS (m/e) = 424 (M⁺) |
| 59A | m.p. 140° |
| 60 | IR (neat) 3358, 2933, 1669, 1580, 1481, 1417, 1234 cm⁻¹. |

CHART C Physical Data

| Example | Physical Data |
|---|---|
|  | NMR (CDCl₃) 7.60, 6.79, 6.69, 5.77, 4.01, 2.9-3.1, 0.90-2.6 δ; MS (EI) m/e (relative %) 384 (25), 237 (24), 162 (69), 150 (69), 137 (100) |
| 60A | m.p. 128-130° dec |
| 61 | IR (neat) 2932, 2856, 1670, 1564, 1435, 1345, 787 cm⁻¹. NMR (CDCl₃) 5.80, 4.78, 3.0-3.6, 1.0-2.6 δ; MS (EI) m/e (relative %) 480 (4), 330 (7), 246 (100), 233 (15) |
| 61A | m.p. 146-150° dec |
| 62 | IR (neat) 3361, 2938, 1669, 1580, 1481, 1417, 1371, 1234, 1150, 788, 772 cm⁻¹. NMR (CDCl₃) 7.71, 6.90, 6.80, 5.89, 4.13, 3.0-3.2, 2.1-2.8, 1.4-1.6, 1.30 δ; MS (EI) m/e (relative %) 356 (27), 162 (21), 150 (83), 137 (100) |
| 62A | m.p. 97-99° dec |
| 63 | IR (neat) 3363, 2944, 2844, 1667, 1580, 1482, 1456, 1418, 1234, 1150, 790, 773 cm⁻¹; MS (EI) m/e (relative %) 342 (38), 162 (28), 150 (100), 137 (90) |
| 63A | m.p. 112-114° dec |
| 64 | IR (neat) 2947, 2868, 1667, 1562, 1450, 1346, 1242, 1224, 788, 731 cm⁻¹; MS (EI) m/e (relative %) 438 (5), 329 (12), 246 (100), 121 (8) |
| 64A | m.p. 103-106° dec |
| 65 | NMR (CDCl₃) 1.7-2.2, 2.4-2.7, 3.3-3.8, 4.0, 4.88, 6.9-7.15, 7.25-7.5 δ |
| 65A | m.p. 169-170° |
| 66 | NMR (CDCl₃) 1.39, 1.63, 1.98, 2.09, 2.12, 2.16, 2.65, 2.73, 3.3-4.0 and 4.78 δ |
| 66A | m.p. 60-71° |
| 67 | NMR (CDCl₃) 1.26, 1.95, 2.11, 2.13, 2.18, 2.65, 3.42, 3.52, 3.67 and 4.84 δ |
| 67A | m.p. 148-152° |
| 68 | m.p. 67-71 |
| 69 | m.p. 163-164° |
| 70 | m.p. 121-123° |
| 71 | NMR (80 MHz, CDCl₃) 1.4, 2.55, 3.56, 4.7, 5.3 and 7.25 δ |
| 71A | m.p. 213-214° |
| 72 | NMR (80 MHz, CDCl₃) 1.25, 1.44, 2.45-2.65, 2.95-3.2, 3.48, 5.06, 6.75-6.85, 7.11, 7.6-7.75 δ |
| 72A | m.p. 190-192° |
| 73 | TLC (ethyl acetate/hexane, 2/1) Rf = 0.47 |
| 73A | m.p. 181-184° |
| 74 | m.p. 80-81° |
| 75 | NMR (CDCl₃) 1.31, 1.40, 1.99, 2.10, 2.12, 2.15, 2.65, 2.75, 3.0-3.2, 3.6-3.9, 4.16, 4.51, 6.88, 6.96 and 7.71 δ |
| 78A | m.p. 130-140° dec; MS (EI) m/e 537 (M⁻) |
| 79 | m.p. 150-151°; MS (EI) m/e 424 (M⁻) |
| 80 | m.p. 153-155°; MS (EI) m/e 395 (M⁻) |
| 81 | m.p. 166-169°; MS (EI) m/e 396 (M⁻) |
| 82 | m.p. 130-131°; MS (EI) m/e 428, 430 (M⁻) |
| 83 | m.p. 196-198°; MS (EI) m/e 452 (M⁻) |
| 84 | m.p. 115-125°; MS (EI) m/e 519 (M⁻) |
| 85 | m.p. 164-165°; MS (EI) m/e 428 (M⁻) |
| 86 | m.p. 157-159° |
| 87 | m.p. 127-127.5°; MS (EI) m/e 413 (M⁻) |
| 88 | m.p. 153-155°; MS (EI) m/e 318 (M⁻) |
| 89 | m.p. 131-132°; MS (EI) m/e 340 (M⁻) |
| 90 | m.p. 58-60°; MS (EI) m/e 368 (M⁻) |
| 91 | m.p. 177-178°; MS (EI) m/e 383 (M⁻) |
| 92 | m.p. 105-107°; MS (EI) m/e 354 (M⁻) |
| 93 | MS (EI) m/e 368 (M⁻) |
| 94 | m.p. 136.5-138.5 ; MS (EI) m/e 340 (M⁻) |
| 96 | m.p. 178-179°; MS (EI) m/e 395 (M⁻) |
| 99 | m.p. 65-67°; MS (EI) m/e 458 (M⁻) |
| 100 | m.p. 147-148°; MS (HR) 466.2938 |
| 101 | m.p. 85-88°; MS (HR) 466.2913 |
| 102 | m.p. 173-174°; MS (EI) m/e 326 (M⁻) |
| 103 | m.p. 105-106°; MS (EI) m/e 325 (M⁻) |
| 104 | m.p. 218-220°; MS (EI) m/e 326 (M⁺) |
| 105 | m.p. 108-109°; MS (EI) m/e 356 (M⁻) |
| 106 | m.p. 154-155°; MS (EI) m/e 482 (M⁺) |
| 107 | m.p. 75-78°; MS (HR) 510.3318 |
| 108 | m.p. 73-74°; MS (EI) m/e 381 (M⁻) |
| 109 | m.p. 156-157°; MS (EI) m/e 399 (M⁻) |
| 110 | m.p. 91-92°; MS (EI) m/e 367 (M⁻) |
| 111 | m.p. 91-92°; MS (HR) 383.2107 |
| 112 | m.p. 90-91°; MS (EI) m/e 353 (M⁻) |
| 113A | m.p. 215-220°; MS (EI) m/e 523 (M⁻) |

CHART C Physical Data

| Example | Physical Data |
|---|---|
| 114A | m.p. 187-189°; MS (EI) m/e 399 (M⁻) |
| 115A | m.p. 213-216°; MS (EI) m/e 410 (M⁻) |
| 116A | m.p. 277-278°; MS (EI) m/e 381 (M⁻) |
| 117A | m.p. 253-256°; MS (EI) m/e 382 (M⁻) |
| 119A | m.p. 189-193°; MS (EI) m/e 414 (M⁻) |
| 120A | m.p. 210° (dec); MS (EI) m/e 438 (M⁺) |
| 121A | m.p. 210° (dec); MS (EI) m/e 504 (M⁻) |
| 122 | m.p. 141-142°; MS (EI) m/e 414, 416 (M⁻) |
| 123 | m.p. 109-110°; MS (EI) m/e 410 (M⁻) |
| 124A | m.p. 186-188°; MS (EI) m/e 369 (M⁺) |
| 125A | m.p. 248-250°; MS (EI) m/e 394 (M⁻) |
| 126A | m.p. 210-212°; MS (EI) m/e 304 (M⁻) |
| 127 | m.p. 99-100°; MS (EI) m/e 289 (M⁺) |
| 128 | m.p. 104-106°; MS (EI) m/e 306 (M⁺) |
| 129A | m.p. 154-157°; MS (EI) m/e 354 (M⁻) |
| 130A | m.p. 304-305°; MS (EI) m/e 312 (M−+) |
| 131 | m.p. effer 63°; MS (HR) 452-3164 |
| 132A | m.p. 125-127°; MS (HR) 311.1895 |
| 133A | m.p. effer 92°; MS (HR) 452-3170 |
| 134 | m.p. 140-143°; MS (EI) m/e 312 (M⁻) |
| 135A | m.p. effer 92°; MS (HR) 342.1946 |
| 136A | m.p. 219-220°; MS (EI) m/e 339 (M⁻) |
| 137A | m.p. 179-180°; MS (EI) m/e 367 (M⁻) |
| 138A | m.p. 201-202°; MS (EI) m/e 353 (M⁻) |
| 139A | m.p. 224-225°; MS (EI) m/e 385 (M⁻) |
| 140A | m.p. 146-148°; MS (EI) m/e 326 (M⁻) |
| 141A | m.p. 229-231°; MS (EI) m/e 326 (M⁻) |
| 142A | m.p. 170-173°; MS (EI) m/e 444 (M⁻) |
| 143A | m.p. 151-154°; MS (EI) m/e 340 (M⁻) |
| 145A | m.p. 204-207°; MS (EI) m/e 380 (M⁻) |
| 146 | m.p. 171-172.5°; MS (EI) m/e 562 (M⁻) |
| 147A | m.p. 229-230°; MS (EI) m/e 354 (M⁻) |
| 148A | m.p. 150-155° |
| 149 | m.p. 174-175°; MS (EI) m/e 451 (M⁻) |
| 150 | m.p. 133-134°; MS (EI) m/e 408 (M⁻) |
| 151A | m.p. 185-187° |
| 152A | m.p. 167-168° |
| 153 | MS (EI) m/e 605 (M⁻) |
| 154A | m.p. 137° |
| 155A | m.p. 217-219° |
| 156A | m.p. 117-180° |
| 157 | MS (EI) m/e 657 |
| 158A | m.p. 247-249° |
| 159A | m.p. 78-80° |
| 173A | m.p. 167-169° |
| 177 | MS m/e 343 |
| 178 | IR (mineral oil) 3459, 1753, 1626, 1570, 1508, 1417, 1321, 1249, 1209 and 1171 cm⁻¹ |
| 179 | IR (mineral oil) 3266, 1626, 1570, 1508, 1478, 1417, 1321, 1254, 1230 and 1169 cm⁻¹ |
| 181 | MS m/e 458 |
| 182 | m.p. 82° softens, 107° decomp. 126° |

| EXAMPLE | |
|---|---|
| | Column A. non-amine |
| 2 | 6-bromohexanol |
| 3 | 6-bromohexanol |
| 4 | 6-bromohexanol |
| 5 | 6-bromohexanol |
| 6 | 1-bromotetradecane |
| 7 | methyl 5-bromovalerate |
| 8 | 1-bromohexane |
| 9 | 6-mesyloxyhexanol (PREPARATION NA-3) |
| 10 | 12-mesyloxydodecanol (PREPARATION NA-5) |
| 11 | 8-mesyloxyoctanol (PREPARATION NA-1) |
| 12 | 5-mesyloxypentanol (PREPARATION NA-2) |
| 13 | 10-mesyloxydecanol (PREPARATION NA-4) |
| 14 | 10-mesyloxydecanol |
| 15 | 8-mesyloctanol |
| 16 | 6-bromohexanol |
| | Column B. amine |
| 2 | 2-pyridinyl-1-piperazine (PREPARATION A-6) |
| 3 | 3-ethylamino-2-(1-piperazinyl)pyridine (PREPARATION A-47) |

-continued

| EXAMPLE | | |
|---|---|---|
| 4 | 3,6-bis(2-pyridinyl)-4-(methyl[1-piperazinyl] pyridazine (PREPARATION A-52) | |
| 5 | bispicolylamine (PREPARATION A-54) | |
| 6 | 2,6-bis(1-pyrrolidinyl)-4-(1-piperazinyl)pyrimidine (PREPARATION A-22) | |
| 7 | 2,6-bis(1-pyrrolidinyl)-4-(1-piperazinyl)pyrimidine | |
| 8 | 2,6-bis(1-pyrrolidinyl)-4-(1-piperazinyl)pyrimidine | |
| 9 | 2,6-bis(1-pyrrolidinyl)-4-(1-piperazinyl)pyrimidine | |
| 10 | 2,6-bis(1-pyrrolidinyl)-4-(1-piperazinyl)pyrimidine | |
| 11 | 2,6-bis(1-pyrrolidinyl)-4-(1-piperazinyl)pyrimidine | |
| 12 | 2,6-bis(1-pyrrolidinyl)-4-(1-piperazinyl)pyrimidine | |
| 13 | 2,6-bis(1-pyrrolidinyl)-4-(1-piperazinyl)pyrimidine | |
| 14 | 3-ethylamino-2-(1-piperazinyl)pyridine | |
| 15 | 3-ethylamino-2-(1-piperazinyl)pyridine | |
| 16 | 2,6-bis(2-pyridinyl)-4-(1-piperazinyl)-1,3,5-triazine (PREPARATION A-49) | |

| EXAMPLE | Column A (Non-amine) | Column B (Amine) |
|---|---|---|
| 27 | NA-9 | A-22 |
| 28 | NA-8 | A-22 |
| 29 | NA-9 | A-51 |
| 30 | NA-7 | A-22 |
| 31 | NA-7 | A 47 |
| 32 | NA-7 | A-52 |
| 33 | NA-7 | A-51 |
| 34 | NA-10 | A-51 |
| 35 | NA-12 | A-22 |
| 36 | NA-12 | A-47 |
| 37 | NA-12 | A-56 |
| 38 | NA-13 | A-22 |
| 39 | NA-16 | A-22 |
| 61 | NA-25 | A-22 |
| 62 | NA-24 | A-47 |
| 63 | NA-26 | A-47 |
| 64 | NA-26 | A-22 |

We claim:

1. An aromatic amine of the formula (I)

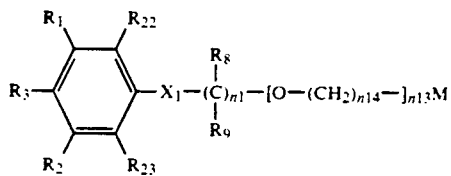

where:
(I) $R_1$ or $R_2$ and $R_3$ taken together are —O—CH$_2$—O— and the other of $R_1$ or $R_2$ is —H;
$R_{22}$ is —H, —Cl or $C_1$-$C_3$ alkyl;
$R_{23}$ is —H, —Cl or $C_1$-$C_3$ alkyl;
or (II) $R_1$ and $R_2$ are the same or different and are —H, $C_1$-$C_4$ alkyl, —F, —Cl and —Br, and $R_3$ is —H, —OH, $C_1$-$C_3$ alkoxy, —O—SO$_2$—CH$_3$, —O—CO—($C_1$-$C_4$ alkyl) and —O-prodrug where prodrug is
—PO$_2$—O$^-$,
—CO—CH$_2$—CO—NH—CH$_2$—SO$_2$—O$^-$,
—CO—(CH$_2$)$_{n21}$—R$_{51}$ where $n_{21}$ is 1-7 and $R_{51}$ is —COO$^-$, —NR$_{51-1}$R$_{51-2}$ where $R_{51-1}$ and $R_{51-2}$ are the same or different and are —H or $C_1$-$C_3$ alkyl, —N$^+$R$_{51-1}$R$_{51-2}$R$_{51-3}$halide$^-$ where $R_{51-1}$R$_{51-2}$R$_{51-3}$ are the same or different and are —H or $C_1$-$C_3$ alkyl, and where halide is —Cl or —Br,
—CO—CH=CH—CO—O$^-$,
—CO—N*—CH=CH—N=CH* where the atoms marked with an asterisk (*) are bonded to each other resulting in the formation of a ring,
—CO—C*=C[(CH$_2$)$_{n22}$—NH$_2$]—CH=CH—CH=CH* where $n_{22}$ is 1 or 2 and where the atoms marked with an asterisk (*) are bonded to each other resulting in the formation of a ring,
—CO—C*=CH—CH=C(—NR$_{5-2}$)—CH=CH* where $R_{52}$ is —H or $C_1$-$C_3$ alkyl and where the atoms marked with an asterisk (*) are bonded to each other resulting in the formation of a ring,
—CO—(CH$_2$)$_{n21}$—CO—O—[C$_6$H$_{12}$O$_6$ sugars],
—CO—O—CH(CH$_2$—O—CO—R$_{53}$)$_2$ where the $R_{53}$'s are the same or different and are $C_1$-$C_{18}$.
—CO—(CH$_2$)$_6$—CO—N(CH$_3$)—CH$_2$—CH$_2$—SO$_3$$^-$cation$^+$ where cation$^+$ is sodium, potassium or trialkylammonium where alkyl is $C_1$-$C_3$,
—CH$_2$—O—CO—(CH$_2$)$_{n21}$   —NR$_{51-1}$R$_{51-2}$ where $n_{21}$, $R_{51-1}$ and $R_{51-2}$ are as defined above,
—CO—NH—C$_6$H$_4$—R$_{55}$ where $R_{55}$ is —H or $C_1$-$C_3$ alkyl, —NO$_2$, —NR$_{51-1}$R$_{51-2}$ where $R_{51-1}$ and $R_{51-2}$ are as defined above and $R_{22}$ is —H, —OH, —Cl, $C_1$-$C_3$ alkyl, —OCH$_3$ or —OC$_2$H$_5$;

$R_{23}$ is —H, —OH, —Cl, $C_1$-$C_3$ alkyl, —OCH$_3$ or —OC$_2$H$_5$; with the proviso that only two of $R_3$, $R_{22}$ and $R_{23}$ can have a variable substituent containing an oxygen atom attached to the benzene ring; where $X_1$ is —O—,
—CH$_2$—,
—C(CH$_3$)(CH$_3$)—,
—C(H)(R$_{24}$)— where $R_{24}$ is $C_1$-$C_3$ alkyl or phenyl optionally substituted with 1 or 2 —OH, —CH$_3$ or —OCH$_3$,
—C(OH)(R$_{13}$) where $R_{13}$ is —H or $C_1$-$C_3$ alkyl, or phenyl optionally substituted with 1 or 2 —OH, —CH$_3$ or —OCH$_3$,
—S—, —Si—, —CO—, —NH—CO— and —NR$_4$— where $R_4$ is —H or $C_1$-$C_4$ alkyl;
$n_1$ is 0-10;
$R_8$ and $R_9$ are the same or different and are —H or $C_1$-$C_3$ alkyl;
$n_{13}$ is 0 or 1;
$n_{14}$ is 2-5;
M is (I') —NR$_A$R$_B$ where:
$R_A$ and $R_B$ are taken together with the attached nitrogen atom to form a heterocyclic ring selected from the group consisting of
(1) 2-(carboxy)-1-pyrrolidinyl optionally as the $C_1$-$C_3$ alkyl ester or as a pharmaceutically acceptable salt, (F-27)
(2) 2-(carboxy)-1-piperidinyl optionally as the $C_1$-$C_3$ alkyl ester or as a pharmaceutically acceptable salt, (F-28)
(3) 2-(carboxy)-1-hexamethyleneimino optionally as the $C_1$-$C_3$ alkyl ester or as a pharmaceutically acceptable salt, (F-29)
(4) 2-(carboxy)-1-heptamethyleneimino optionally as the $C_1$-$C_3$ alkyl ester or as a pharmaceutically acceptable salt, (F-30)
(5) 1-piperazinyl optionally substituted in the 4-position with $R_{M-12}$—CO—(CH$_2$)$_j$— where where j is 0 through 3, $R_{M-12}$ is -aryl, where aryl is phenyl optionally substituted with 1 -F or —CF₃ or with 1 or 2 -F, —Cl, —Br, $C_1$-$C_3$ alkoxy, —COOH, —NH₂, $C_1$-$C_3$ alkylamino, di($C_1$-$C_3$)alkylamino, where the alkyl groups are the same or different, 1-pyrrolidinyl-, 1-piperidinyl, 1-hexamethylenimino-, 1-heptamethyleneimino-, $C_2$-$C_4$ acylamino and —NH—CHO; or $R_{M-12}$ is -heteroaryl, where heteroaryl is: (a) pyridin-2- (F-1), 3- (F-2) or 4-yl (F-3) or the N-oxide thereof optionally substituted by 1 or 2 $R_{M-2}$, being the same or different, where $R_{M-2}$ is (i) —F,
(ii) —Cl,
(iii) —Br,
(iv) $C_1$-$C_5$ alkyl,
(v) —CH₂—CH=CH₂,
(vi) -aryl, where aryl is as defined above,
(vii) —$NR_{M-3}R_{M-3}$ where the $R_{M-3}$s are the same or different and are —H, $C_1$-$C_3$ alkyl or —CH₂—CH=CH₂,
(viiiα) *CH₂—(CH₂)$_q$—CH₂—N*— where the atoms marked with an asterisk (*) are bonded to each other resulting in the formation of a ring, where q is 1 through 5,
(viiiβ) *CH₂—(CH₂)$_c$—G—(CH₂)$_d$—CH₂—N*— where the atoms marked with an asterisk (*) are bonded to each other resulting in the formation of a ring (F-4), where G is —O—, —S—, —SO—, —SO₂— or —$NR_{M-4}$—, where $R_{M-4}$ is —H, $C_1$-$C_3$ alkyl, or aryl as defined above, where c and d are the same or different and are 0 through 2 with the proviso that the total number of ring carbon atoms is 4, 5 or 6.
(ix) 3-pyrrolin-1-yl, (F-5)
(x) pyrrol-1-yl optionally substituted with $C_1$-$C_3$ alkyl, (F-6)
(xi) piperidin-1-yl optionally substituted with 1 or 2 $C_1$-$C_3$ alkyl, (F-7)
(xii) 1,2,3,6-tetrahydropyridin-1-yl, (F-8)
(xiii) 1-hexamethyleneimino containing a 3-or 4- double bond or 3- and 5-double bonds,
(xiv) 1,4-dihydro-1-pyridinyl substituted in the 4 position by two $C_1$-$C_3$ alkyl being the same or different, (F-10)
(xv) —OH,
(xvi) $C_1$-$C_3$ alkoxy,
(xvii) —$NR_{M-7}$—(CH₂)$_e$—Q where Q is 2-pyridinyl where $R_{M-7}$ is —H or $C_1$-$C_3$ alkyl and e is 0 through 3,
(xviii) pyridin-2-, 3- or 4-yl,
(xix) —CF₃,
(xx) —CCl₃,
(xxi) —S—CH₃, (b) 1,3,5-triazin-2-yl or the N-oxide thereof optionally substituted at the 4- and/or 6-position with $R_{M-2}$ is as defined above, (F-11)
(c) pyrimidin-4-yl or the N-oxide thereof optionally substituted at the 2- and/or 6-, and 5- and/or 6-position with $R_{M-2}$ is as defined above, (F-12)
(d) pyrimidin-2-yl optionally substituted at 4- and/or 6-position with 1 or 2 $R_{M-2}$ as is defined above, (F-13)
(e) pyrazin-2-yl optionally substituted with 1 or 2 $R_{M-2}$ as is defined above, (F-14)
(f) imidazol-2-yl optionally substituted in the 1 position with $C_1$-$C_3$ alkyl or -aryl, where aryl is as defined above, and further optionally substituted with 1 or 2 $R_{M-2}$ as defined above, (F-15)
(g) 1,3,4-triazol-2-yl optionally substituted in the 1 position with $C_1$-$C_3$ alkyl or -aryl, where aryl is as defined above, and further optionally substituted with $R_{M-2}$ as defined above. (F-16)
(h) imidazol-4- or 5-yl optionally substituted in the 1 position with $C_1$-$C_3$ alkyl or -aryl, where aryl is as defined above, and further optionally substituted with 1 or 2 $R_{M-2}$ as defined above, (F-17)
(i) benzo[b]thien-2-yl, (F-18)
(j) indol-2-yl, (F-19)
(k) benzo[b]thiazol-2-yl, (F-20)
(l) benzimidazol-2-yl, (F-21)
(m) 4-[2-[4-[2,6-bis(1-pyrrolidinyl)-4-pyrimidinyl]-1-piperazinyl]ethyl], (F-22)
(n) 1,2,4-triazin-3-yl optionally substituted at the 5- and/or 6-position with $R_{M-2}$ as is defined above, (F-23) or $R_{M-12}$ is 2-furanyl, or $R_{M-12}$ is —$NR_{M-13}$heteroaryl, where $R_{M-13}$ is —H or $C_1$-$C_3$ alkyl, and heteroaryl is as defined above, (F-31)

(6) 1-piperazinyl substituted in the 4-position with heteroaryl-(CH₂)$_j$—, where heteroaryl and j are as defined above, (F-32)
(7) 1-piperazinyl substituted in the 4-position with aryl—(CH₂)$_j$—, where aryl and j are as defined above, (F-33)
(8) 4-hydroxy-1-piperidinyl substituted in the 4-position with aryl where aryl is as defined above, (F-34)
(9) 1-piperazinyl substituted in the 4-position with heteroaryl-$NR_{M-13}$—CO—(CH₂)$_i$—, where i is 1 thru 4 and where heteroaryl and $R_{M-13}$ are as defined above; (F-35)
(10) 1-piperazinyl substituted in the 4-position with —(CH₂)$_j$—C*=C(2-pyridinyl)—N=N—C(2-pyridinyl)=C*H, where * and j are as defined above, (F-36)
(11) 1-piperazinyl substituted in the 4-position with —(CH₂)$_j$—[4-[2,6-bis(1-pyrrolidinyl)-4-pyrimidinyl]-1-piperazine] (F-37) or M is
(II') —C*=C(2-pyridinyl)—N=N—C(2-pyridinyl)=C*H where * is as defined above and pharmaceutically acceptable salts thereof, and hydrates and solvates thereof.

2. An aromatic amine according to claim 1 where $X_1$ is —O—.

3. An aromatic amine according to claim 1 where $X_1$ is —CH₂—.

4. An aromatic amine according to claim 1 where $X_1$ is —CO—.

5. An aromatic amine according to claim 1 where $n_1$ is 0-6.

6. An aromatic amine according to claim 1 where $n_1$ is 1-6.

7. An aromatic amine according to claim 1 where $R_1$ and $R_2$ are the same and are —H, $C_1$ alkyl or $C_4$ alkyl.

8. An aromatic amine according to claim 1 where $R_3$ is —OH or $C_1$-$C_3$ alkoxy.

9. An aromatic amine according to claim 1 where $R_8$ and $R_9$ are both —H.

10. An aromatic amine according to claim 1 which is 2,6-bis(1,1-dimethylethyl)-4[[4-[2-[4-(2,6-bis(1-pyrrolidinyl)-4-pyrimidinyl)-1-piperazinyl]ethyl]-1-piperazinyl]methyl]phenol, 4-[4-[6-(4-methoxyphenoxy)hexyl]-1-piperazinyl]-2,6-bis(1-pyrrolidinyl]pyrimidine,
N-ethyl-2-[4-[6-(4-methoxyphenoxy)hexyl]-1-piperazinyl]-3-pyridinamine,
4-[4-[4-(2,6-bis(1-pyrrolidinyl)-4-pyrimidinyl)-1-piperazinyl]butoxy]phenol,
4-[5-[4-(2,6-bis(1-pyrrolidinyl)-4-pyrimidinyl)-1-piperazinyl]pentoxy]phenol,
4-[4-[4-(2,6-bis(2-pyridinyl)-4-pyrimidinyl)-1-piperazinyl]butoxy]phenol,
4-[6-[4-(2,6-bis(1-pyrrolidinyl)-4-pyrimidinyl)-1-piperazinyl]hexyloxy]phenol,
4-[6-[4-[3-(ethylamino)-2-pyridinyl]-1-piperazinyl]hexyloxy]phenol,
4-[6-[4-(3,6-bis(2-pyridinyl)-4-pyridazinyl)methyl-1-piperazinyl]hexyloxy]phenol,
4-[6-[4-(2,6-bis(2-pyridinyl)-4-pyrimidinyl)-1-piperazinyl]hexyloxy]phenol,
4-[6-[4-(2,6-bis(2-pyridinyl)-4-pyrimidinyl)-1-piperazinyl]hexyloxy]anisole,
5-[3-(4-(2,6-bis(1-pyrrolidinyl)pyrimidin-4-yl)piperazin-1-yl)propylbenzodioxole,
5-[3-((N-ethylaminopyridin-2-yl)piperazin-1-yl)propylbenzodioxole,
1,2-methylenedioxy-4-[(3-[1-piperazinyl(4-(2-morpholino-6-methoxypyrimidinyl))]propyl]benzene,
2-[4-2,6-bis(1-pyrrolidinyl)-4-pyrimidinyl-1-piperazinyl]-4-methoxyphenylethane,
1-phenyl-3-[4-(2,6-bis(1-pyrrolidinyl)-4-pyrimidinyl)-1-piperazinyl]-propane,
4-[2-[4-(2,6-bis(1-pyrrolidinyl)-4-pyrimidinyl)-1-piperazinyl]ethoxy]phenol,
1-[2-(4-Methoxy-3,5-dimethylphenyl)-2-hydroxypropyl]-4-[2,6-bis(1-pyrrolidinyl-4-pyrimidinyl)piperazine,
1-[4-(4-methoxy-3,5-dimethylphenyl)butyl)]-4-(bis(1-pyrrolidinyl))pyrimidin-4-yl)piperazine,
2-[4-(4-(3,5-dimethyl-4-methoxyphenyl)butyl)piperazin-1-yl]-N-ethyl-3-pyridineamine,
2-[4-(4-(3,5-dimethyl-4-hydroxyphenyl)butyl)piperazin-1-yl]-N-ethyl-3-pyridineamine,
1-[4-(4-hydroxy-3,5-dimethylphenyl)butyl)]-4-(di(1-pyrrolidinyl))pyrimidin-4-yl)piperazine,
1-(4-methoxyphenoxy)-6-[3,6-bis(2-pyridinyl)-4-pyridazinyl]hexane,
2,6-dimethyl-4-[3-(2,4-bis(1-pyrrolidinyl)-6-pyrimidinyl)piperazinyl)propyl phenol,
4-[3-(4-(3-(N-ethylamino)pyridin-2-yl)piperazin-1-yl)propyl]-2,6-dimethylphenol,
2,6-bis(1-pyrrolidinyl)-4-[4-(3-(3,5-dimethyl-4-methoxyphenyl)propyl)piperazinyl]pyrimidine,
N-ethyl-2-[4-[3-(4-methoxy-3,5-dimethylphenyl)propyl]-1-piperazinyl]-3-pyridinamine,
4-[2-[4-(2,6-bis(1-pyrrolidinyl)-4-pyrimidinyl-1-piperazinyl]ethyl]-2,6-dimethylphenol,
4-[2-[4-[3-(ethylamino)-2-pyridinyl]-1-piperazinyl]ethyl]-2,6-dimethylphenol,
4-[4-[2-(4-methoxy-3,5-dimethylphenyl)ethyl]-1-piperazinyl]-2,6-bis(1-pyrrolidinyl)pyrimidine,
N-ethyl-2-[4-[2-(4-methoxy-3,5-dimethylphenyl)ethyl]-1-piperazinyl]-3-pyridinamine,
2,6-bis(1-pyrrolidinyl)-4-[4-[6-(3,5-dimethyl-4-methoxyphenyl)hexyl]-1-piperazinyl]pyrimidine,
2-[4-[6-(3,5-dimethyl-4-methoxyphenyl)hexyl]-1-piperazinyl]-N-ethyl-3-pyridinamine,
1-phenoxy-4-[4-(2,6-bis(1-pyrrolidinyl)-4-pyrimidinyl)-1-piperazinyl]-butane,
2,6-bis(1,1-dimethylethyl)-4-[[4-(2,6-bis-1-pyrrolidinyl-4-pyrimidinyl)-1-piperazinyl]methyl]phenol,
2,6-bis(1,1-dimethylethyl)-4-[[4-(2-pyridinyl)-1-piperazinyl]methyl]phenol,
2,6-bis(1,1-dimethylethyl)-4-[[4-(3-(ethylamino)-2-pyridinyl]-1-piperazinyl]methyl]phenol,
4-(2,6-bis(1-pyrrolidinyl)-4-pyrimidinyl)-N-(4-hydroxy-3,5-dimethylphenyl)-1-piperazineacetamide,
4-[4-(6-(4-Methoxyl-1-thio)hexylphenyl)-1-piperazinyl]-2,6-bis(1-pyrrolidinyl)pyrimidine,
2,6-bis(1-pyrrolidinyl)-4-[4-((2-(3,5-dimethyl-4-methoxyphenyl)-2-(4-methoxyphenyl)-2-hydroxyethyl)-piperazinylpyrimidine and
4-[4-[2-(ethylamino)-4-(2-pyridinyl)-1-piperazinyl]-butyl]-2,6-dimethylphenol methanesulfonate.

* * * * *